(12) United States Patent
Shelton, IV et al.

(10) Patent No.: US 7,568,603 B2
(45) Date of Patent: Aug. 4, 2009

(54) MOTOR-DRIVEN SURGICAL CUTTING AND FASTENING INSTRUMENT WITH ARTICULATABLE END EFFECTOR

(75) Inventors: Frederick E. Shelton, IV, New Vienna, OH (US); Christoph L. Gillum, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 81 days.

(21) Appl. No.: 11/343,562

(22) Filed: Jan. 31, 2006

(65) Prior Publication Data

US 2007/0175959 A1    Aug. 2, 2007

(51) Int. Cl.
*A61B 17/072* (2006.01)
*A61B 17/068* (2006.01)

(52) U.S. Cl. ............... 227/178.1; 227/180.1; 227/19

(58) Field of Classification Search ... 227/175.1–182.1, 227/19
See application file for complete search history.

(56) References Cited

U.S. PATENT DOCUMENTS

| | | | |
|---|---|---|---|
| 2,037,727 A | 4/1936 | Chapelle |
| 3,269,630 A | 8/1966 | Fleischer |
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,819,100 A | 6/1974 | Noiles et al. |
| 3,892,228 A | 7/1975 | Mitsui |
| 3,894,174 A | 7/1975 | Cartun |
| 3,940,844 A | 3/1976 | Colby et al. |
| 4,213,562 A | 7/1980 | Garrett et al. |
| 4,331,277 A | 5/1982 | Green |
| 4,349,028 A * | 9/1982 | Green ........................ 606/143 |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,442,964 A | 4/1984 | Becht |

(Continued)

FOREIGN PATENT DOCUMENTS

CA    2458946 A1    3/2003

(Continued)

OTHER PUBLICATIONS

Office Action issued on Apr. 10, 2007 in U.S. Appl. No. 11/343,439.

(Continued)

*Primary Examiner*—Rinaldi I. Rada
*Assistant Examiner*—Lindsay Low

(57) ABSTRACT

A surgical cutting and fastening instrument is disclosed. According to various embodiments, the instrument includes an end effector comprising a moveable cutting instrument. The instrument also includes a main drive shaft assembly for actuating the cutting instrument in the end effector. The instrument also includes a handle comprising a gear drive train connected to the main drive shaft assembly, a motor for actuating the gear drive train, a closure trigger for causing the end effector to clamp an object positioned in the end effector when the closure trigger is retracted, and a firing trigger separate from the closure trigger for actuating the motor when the firing trigger is retracted. The instrument further comprises means for articulating the end effector.

32 Claims, 39 Drawing Sheets

U.S. PATENT DOCUMENTS

| | | | |
|---|---|---|---|
| 4,475,679 A | 10/1984 | Fleury, Jr. | |
| 4,500,024 A | 2/1985 | DiGiovanni et al. | |
| 4,520,817 A | 6/1985 | Green | |
| 4,522,327 A | 6/1985 | Korthoff et al. | |
| 4,526,174 A | 7/1985 | Froehlich | |
| 4,527,724 A | 7/1985 | Chow et al. | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,605,001 A | 8/1986 | Rothfuss et al. | |
| 4,606,343 A | 8/1986 | Conta et al. | |
| 4,608,981 A | 9/1986 | Rothfuss et al. | |
| 4,610,383 A | 9/1986 | Rothfuss et al. | |
| 4,629,107 A | 12/1986 | Fedotov et al. | |
| 4,671,445 A | 6/1987 | Barker et al. | |
| 4,709,120 A | 11/1987 | Pearson | |
| 4,715,520 A | 12/1987 | Roehr, Jr. et al. | |
| 4,728,020 A | 3/1988 | Green et al. | |
| 4,728,876 A | 3/1988 | Mongeon et al. | |
| 4,729,260 A | 3/1988 | Dudden | |
| 4,754,909 A | 7/1988 | Barker et al. | |
| 4,767,044 A | 8/1988 | Green | |
| 4,790,225 A | 12/1988 | Moody et al. | |
| 4,821,939 A | 4/1989 | Green | |
| 4,869,414 A | 9/1989 | Green et al. | |
| 4,869,415 A | 9/1989 | Fox | |
| 4,880,015 A | 11/1989 | Nierman | |
| 4,892,244 A | 1/1990 | Fox et al. | |
| 4,938,408 A | 7/1990 | Bedi et al. | |
| 4,941,623 A | 7/1990 | Pruitt | |
| 4,944,443 A | 7/1990 | Oddsen et al. | |
| 4,955,959 A | 9/1990 | Tompkins et al. | |
| 4,978,049 A | 12/1990 | Green | |
| 5,027,834 A | 7/1991 | Pruitt | |
| 5,031,814 A | 7/1991 | Tompkins et al. | |
| 5,040,715 A | 8/1991 | Green et al. | |
| 5,061,269 A * | 10/1991 | Muller | 606/83 |
| 5,065,929 A | 11/1991 | Schulze et al. | |
| 5,071,430 A | 12/1991 | de Salis et al. | |
| 5,080,556 A | 1/1992 | Carreno | |
| 5,084,057 A | 1/1992 | Green et al. | |
| 5,100,420 A | 3/1992 | Green et al. | |
| 5,104,025 A | 4/1992 | Main et al. | |
| 5,106,008 A | 4/1992 | Tompkins et al. | |
| 5,111,987 A | 5/1992 | Moeinzadeh et al. | |
| 5,116,349 A | 5/1992 | Aranyi | |
| 5,129,570 A | 7/1992 | Schulze et al. | |
| 5,137,198 A | 8/1992 | Nobis et al. | |
| 5,156,315 A | 10/1992 | Green et al. | |
| 5,158,567 A | 10/1992 | Green | |
| 5,171,247 A | 12/1992 | Hughett et al. | |
| 5,171,249 A | 12/1992 | Stefanchik et al. | |
| 5,200,280 A | 4/1993 | Karasa | |
| 5,207,697 A | 5/1993 | Carusillo et al. | |
| 5,211,649 A | 5/1993 | Kohler et al. | |
| 5,221,036 A | 6/1993 | Takase | |
| 5,240,163 A | 8/1993 | Stein et al. | |
| 5,246,156 A | 9/1993 | Rothfuss et al. | |
| 5,253,793 A | 10/1993 | Green et al. | |
| 5,258,009 A | 11/1993 | Conners | |
| RE34,519 E | 1/1994 | Fox et al. | |
| 5,275,323 A | 1/1994 | Schulze et al. | |
| 5,282,806 A | 2/1994 | Haber et al. | |
| 5,282,829 A | 2/1994 | Hermes | |
| 5,304,204 A | 4/1994 | Bregen | |
| 5,307,976 A | 5/1994 | Olson et al. | |
| 5,309,927 A | 5/1994 | Welch | |
| 5,318,221 A | 6/1994 | Green et al. | |
| 5,330,502 A | 7/1994 | Hassler et al. | |
| 5,332,142 A | 7/1994 | Robinson et al. | |
| 5,339,799 A | 8/1994 | Kami et al. | |
| 5,342,395 A | 8/1994 | Jarrett et al. | |
| 5,342,396 A | 8/1994 | Cook | |
| 5,350,400 A | 9/1994 | Esposito et al. | |
| 5,366,479 A | 11/1994 | McGarry et al. | |
| 5,379,933 A | 1/1995 | Green et al. | |
| 5,383,880 A | 1/1995 | Hooven | |
| 5,383,881 A | 1/1995 | Green et al. | |
| 5,389,098 A | 2/1995 | Tsuruta et al. | |
| 5,391,180 A | 2/1995 | Tovey et al. | |
| 5,395,033 A | 3/1995 | Byrne et al. | |
| 5,395,312 A | 3/1995 | Desai | |
| 5,397,046 A | 3/1995 | Savage et al. | |
| 5,397,324 A | 3/1995 | Carroll et al. | |
| 5,403,312 A | 4/1995 | Yates et al. | |
| 5,405,344 A | 4/1995 | Williamson et al. | |
| 5,409,498 A | 4/1995 | Braddock et al. | |
| 5,413,267 A | 5/1995 | Solyntjes et al. | |
| 5,413,268 A | 5/1995 | Green et al. | |
| 5,415,335 A | 5/1995 | Knodell, Jr. | |
| 5,425,745 A | 6/1995 | Green et al. | |
| 5,431,322 A | 7/1995 | Green et al. | |
| 5,431,668 A | 7/1995 | Burbank, III et al. | |
| 5,433,721 A | 7/1995 | Hooven et al. | |
| 5,445,304 A | 8/1995 | Plyley et al. | |
| 5,447,513 A | 9/1995 | Davison et al. | |
| 5,449,365 A | 9/1995 | Green et al. | |
| 5,456,401 A | 10/1995 | Green et al. | |
| 5,458,579 A * | 10/1995 | Chodorow et al. | 604/164.11 |
| 5,462,215 A | 10/1995 | Viola et al. | |
| 5,465,895 A | 11/1995 | Knodel et al. | |
| 5,465,896 A | 11/1995 | Allen et al. | |
| 5,467,911 A | 11/1995 | Tsuruta et al. | |
| 5,470,006 A | 11/1995 | Rodak | |
| 5,472,132 A | 12/1995 | Savage et al. | |
| 5,474,566 A | 12/1995 | Alesi et al. | |
| 5,476,206 A * | 12/1995 | Green et al. | 227/176.1 |
| 5,476,479 A | 12/1995 | Green et al. | |
| 5,478,003 A | 12/1995 | Green et al. | |
| 5,480,089 A | 1/1996 | Blewett | |
| 5,480,409 A | 1/1996 | Riza | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,503,638 A | 4/1996 | Cooper et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,527,320 A | 6/1996 | Carruthers et al. | |
| 5,529,235 A | 6/1996 | Boiarski et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,547,117 A | 8/1996 | Hamblin et al. | |
| 5,549,628 A | 8/1996 | Cooper et al. | |
| 5,553,675 A | 9/1996 | Pitzen et al. | |
| 5,554,169 A | 9/1996 | Green et al. | |
| 5,558,665 A | 9/1996 | Kieturakis | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,574,431 A | 11/1996 | McKeown et al. | |

| | | | | | | |
|---|---|---|---|---|---|---|
| 5,575,799 A * | 11/1996 | Bolanos et al. ............ 606/139 | 5,732,871 A | 3/1998 | Clark et al. | |
| 5,575,803 A | 11/1996 | Cooper et al. | 5,735,445 A | 4/1998 | Vidal et al. | |
| 5,577,654 A | 11/1996 | Bishop | 5,743,456 A | 4/1998 | Jones et al. | |
| 5,579,978 A | 12/1996 | Green et al. | 5,747,953 A | 5/1998 | Philipp | |
| 5,580,067 A | 12/1996 | Hamblin et al. | 5,749,893 A | 5/1998 | Vidal et al. | |
| 5,582,611 A | 12/1996 | Tsuruta et al. | 5,752,644 A | 5/1998 | Bolanos et al. | |
| 5,582,617 A | 12/1996 | Klieman et al. | 5,758,814 A | 6/1998 | Gallagher et al. | |
| 5,584,425 A | 12/1996 | Savage et al. | 5,762,255 A | 6/1998 | Chrisman et al. | |
| 5,586,711 A | 12/1996 | Plyley et al. | 5,762,256 A | 6/1998 | Mastri et al. | |
| 5,588,579 A | 12/1996 | Schnut et al. | 5,779,130 A | 7/1998 | Alesi et al. | |
| 5,588,580 A | 12/1996 | Paul et al. | 5,779,132 A | 7/1998 | Knodel et al. | |
| 5,588,581 A | 12/1996 | Conlon et al. | 5,782,396 A | 7/1998 | Mastri et al. | |
| 5,591,170 A | 1/1997 | Spievack et al. | 5,782,397 A | 7/1998 | Koukline | |
| 5,597,107 A | 1/1997 | Knodel et al. | 5,782,749 A | 7/1998 | Riza | |
| 5,601,224 A | 2/1997 | Bishop et al. | 5,782,859 A | 7/1998 | Nicholas et al. | |
| 5,603,443 A | 2/1997 | Clark et al. | 5,785,232 A | 7/1998 | Vidal et al. | |
| 5,605,272 A | 2/1997 | Witt et al. | 5,792,165 A | 8/1998 | Klieman et al. | |
| 5,605,273 A | 2/1997 | Hamblin et al. | 5,794,834 A | 8/1998 | Hamblin et al. | |
| 5,607,094 A | 3/1997 | Clark et al. | 5,796,188 A | 8/1998 | Bays | |
| 5,607,095 A | 3/1997 | Smith et al. | 5,797,536 A | 8/1998 | Smith et al. | |
| 5,609,285 A | 3/1997 | Grant et al. | 5,797,537 A | 8/1998 | Oberlin et al. | |
| 5,624,452 A | 4/1997 | Yates | 5,797,538 A | 8/1998 | Heaton et al. | |
| 5,626,587 A | 5/1997 | Bishop et al. | 5,799,857 A | 9/1998 | Robertson et al. | |
| 5,628,446 A | 5/1997 | Geiste et al. | 5,807,393 A | 9/1998 | Williamson, IV et al. | |
| 5,630,539 A | 5/1997 | Plyley et al. | 5,810,811 A | 9/1998 | Yates et al. | |
| 5,630,540 A | 5/1997 | Blewett | 5,817,093 A | 10/1998 | Williamson, IV et al. | |
| 5,632,432 A | 5/1997 | Schulze et al. | 5,817,109 A | 10/1998 | McGarry et al. | |
| 5,634,584 A | 6/1997 | Okorocha et al. | 5,817,119 A * | 10/1998 | Klieman et al. ............ 606/174 | |
| 5,636,779 A | 6/1997 | Palmer | 5,820,009 A | 10/1998 | Melling et al. | |
| 5,636,780 A | 6/1997 | Green et al. | 5,823,066 A | 10/1998 | Huitema et al. | |
| 5,639,008 A | 6/1997 | Gallagher et al. | 5,826,776 A | 10/1998 | Schulze et al. | |
| 5,643,291 A | 7/1997 | Pier et al. | 5,829,662 A | 11/1998 | Allen et al. | |
| 5,645,209 A | 7/1997 | Green et al. | 5,833,690 A | 11/1998 | Yates et al. | |
| 5,647,526 A | 7/1997 | Green et al. | 5,836,503 A | 11/1998 | Ehrenfels et al. | |
| 5,649,937 A | 7/1997 | Bito et al. | 5,836,960 A * | 11/1998 | Kolesa et al. ............... 606/170 | |
| 5,651,491 A | 7/1997 | Heaton et al. | 5,839,639 A | 11/1998 | Sauer et al. | |
| 5,653,373 A | 8/1997 | Green et al. | 5,843,132 A | 12/1998 | Ilvento | |
| 5,653,374 A | 8/1997 | Young et al. | 5,855,311 A | 1/1999 | Hamblin et al. | |
| 5,655,698 A | 8/1997 | Yoon | 5,865,361 A | 2/1999 | Milliman et al. | |
| 5,657,921 A | 8/1997 | Young et al. | 5,871,135 A | 2/1999 | Williamson, IV et al. | |
| 5,658,300 A | 8/1997 | Bito et al. | 5,873,885 A * | 2/1999 | Weidenbenner ............ 606/171 | |
| 5,662,258 A | 9/1997 | Knodel et al. | 5,878,937 A | 3/1999 | Green et al. | |
| 5,662,260 A | 9/1997 | Yoon | 5,878,938 A | 3/1999 | Bittner et al. | |
| 5,662,662 A | 9/1997 | Bishop et al. | 5,893,506 A | 4/1999 | Powell | |
| 5,667,517 A | 9/1997 | Hooven | 5,894,979 A | 4/1999 | Powell | |
| 5,667,527 A | 9/1997 | Cook | 5,897,562 A | 4/1999 | Bolanos et al. | |
| 5,669,544 A | 9/1997 | Schulze et al. | 5,901,895 A | 5/1999 | Heaton et al. | |
| 5,673,840 A | 10/1997 | Schulze et al. | 5,906,625 A | 5/1999 | Bito et al. | |
| 5,673,841 A | 10/1997 | Schulze et al. | 5,911,353 A | 6/1999 | Bolanos et al. | |
| 5,673,842 A | 10/1997 | Bittner et al. | 5,915,616 A | 6/1999 | Viola et al. | |
| 5,678,748 A | 10/1997 | Plyley et al. | 5,918,791 A | 7/1999 | Sorrentino et al. | |
| 5,680,981 A | 10/1997 | Mililli et al. | 5,931,853 A | 8/1999 | McEwen et al. | |
| 5,680,982 A | 10/1997 | Schulze et al. | 5,938,667 A | 8/1999 | Peyser et al. | |
| 5,680,983 A | 10/1997 | Plyley et al. | 5,941,442 A | 8/1999 | Geiste et al. | |
| 5,685,474 A | 11/1997 | Seeber | 5,948,030 A * | 9/1999 | Miller et al. ................... 701/41 | |
| 5,688,270 A | 11/1997 | Yates et al. | 5,951,552 A | 9/1999 | Long et al. | |
| 5,690,269 A | 11/1997 | Bolanos et al. | 5,951,574 A | 9/1999 | Stefanchik et al. | |
| 5,692,668 A | 12/1997 | Schulze et al. | 5,954,259 A | 9/1999 | Viola et al. | |
| 5,693,042 A | 12/1997 | Boiarski et al. | 5,988,479 A | 11/1999 | Palmer | |
| 5,697,543 A | 12/1997 | Burdorff | 6,010,054 A | 1/2000 | Johnson et al. | |
| 5,700,270 A | 12/1997 | Peyser et al. | 6,017,356 A | 1/2000 | Frederick et al. | |
| 5,702,408 A | 12/1997 | Wales et al. | 6,022,352 A | 2/2000 | Vandewalle | |
| 5,704,534 A | 1/1998 | Huitema et al. | 6,024,741 A | 2/2000 | Williamson, IV et al. | |
| 5,706,997 A | 1/1998 | Green et al. | 6,024,748 A | 2/2000 | Manzo et al. | |
| 5,706,998 A | 1/1998 | Plyley et al. | 6,032,849 A | 3/2000 | Mastri et al. | |
| 5,709,334 A | 1/1998 | Sorrentino et al. | 6,079,606 A | 6/2000 | Milliman et al. | |
| 5,709,680 A | 1/1998 | Yates et al. | 6,082,577 A | 7/2000 | Coates et al. | |
| 5,711,472 A | 1/1998 | Bryan | 6,083,234 A | 7/2000 | Nicholas et al. | |
| 5,713,505 A | 2/1998 | Huitema | 6,083,242 A | 7/2000 | Cook | |
| 5,715,988 A | 2/1998 | Palmer | 6,086,600 A | 7/2000 | Kortenbach | |
| 5,716,366 A | 2/1998 | Yates | 6,099,537 A | 8/2000 | Sugai et al. | |
| 5,718,359 A | 2/1998 | Palmer et al. | 6,102,271 A | 8/2000 | Longo et al. | |
| 5,725,536 A | 3/1998 | Oberlin et al. | 6,109,500 A | 8/2000 | Alli et al. | |

| | | | | | | |
|---|---|---|---|---|---|---|
| H1904 | H | 10/2000 | Yates et al. | 6,964,363 B2 | 11/2005 | Wales et al. |
| 6,126,670 | A | 10/2000 | Walker et al. | 6,978,921 B2 | 12/2005 | Shelton, IV et al. |
| 6,131,789 | A | 10/2000 | Schulze et al. | 6,978,922 B2 | 12/2005 | Bilotti et al. |
| 6,155,473 | A | 12/2000 | Tompkins et al. | 6,981,628 B2 | 1/2006 | Wales |
| 6,156,056 | A | 12/2000 | Kearns et al. | 6,981,941 B2 | 1/2006 | Whitman et al. |
| 6,162,208 | A | 12/2000 | Hipps | 6,986,451 B1 | 1/2006 | Mastri et al. |
| 6,171,330 | B1 | 1/2001 | Benchetrit | 6,988,649 B2 | 1/2006 | Shelton, IV et al. |
| 6,202,914 | B1 | 3/2001 | Geiste et al. | 6,988,650 B2 | 1/2006 | Schwemberger et al. |
| 6,223,835 | B1 | 5/2001 | Habedank et al. | 7,000,818 B2 | 2/2006 | Shelton, IV et al. |
| 6,241,139 | B1 | 6/2001 | Milliman et al. | 7,000,819 B2 | 2/2006 | Swayze et al. |
| 6,250,532 | B1 | 6/2001 | Green et al. | 7,008,435 B2 | 3/2006 | Cummins |
| 6,264,086 | B1 | 7/2001 | McGuckin, Jr. | 7,032,798 B2 | 4/2006 | Whitman et al. |
| 6,264,087 | B1 | 7/2001 | Whitman | 7,032,799 B2 | 4/2006 | Viola et al. |
| 6,273,897 | B1 | 8/2001 | Dalessandro et al. | 7,036,680 B1 | 5/2006 | Flannery |
| 6,309,403 | B1 | 10/2001 | Minor et al. | 7,044,352 B2 | 5/2006 | Shelton, IV et al. |
| 6,315,184 | B1 | 11/2001 | Whitman | 7,044,353 B2 | 5/2006 | Mastri et al. |
| 6,320,123 | B1 | 11/2001 | Reimers | 7,048,687 B1 | 5/2006 | Reuss et al. |
| 6,325,810 | B1 | 12/2001 | Hamilton et al. | 7,055,730 B2 | 6/2006 | Ehrenfels et al. |
| 6,330,965 | B1 | 12/2001 | Milliman et al. | 7,055,731 B2 | 6/2006 | Shelton, IV et al. |
| 6,358,224 | B1 | 3/2002 | Tims et al. | 7,056,330 B2 | 6/2006 | Gayton |
| 6,387,113 | B1 | 5/2002 | Hawkins et al. | 7,059,508 B2 | 6/2006 | Shelton, IV et al. |
| 6,416,486 | B1 | 7/2002 | Wampler | 7,066,944 B2 | 6/2006 | Laufer et al. |
| RE37,814 | E | 8/2002 | Allgeyer | 7,070,083 B2 | 7/2006 | Jankowski |
| 6,443,973 | B1 * | 9/2002 | Whitman .................... 606/219 | 7,077,856 B2 | 7/2006 | Whitman |
| 6,488,197 | B1 | 12/2002 | Whitman | 7,083,075 B2 | 8/2006 | Swayze et al. |
| 6,491,201 | B1 | 12/2002 | Whitman | 7,090,673 B2 | 8/2006 | Dycus et al. |
| 6,503,257 | B2 | 1/2003 | Grant et al. | 7,090,684 B2 | 8/2006 | McGuckin, Jr. et al. |
| 6,505,768 | B2 | 1/2003 | Whitman | 7,097,089 B2 | 8/2006 | Marczyk |
| 6,511,468 | B1 | 1/2003 | Cragg et al. | 7,098,794 B2 | 8/2006 | Lindsay et al. |
| 6,522,101 | B2 | 2/2003 | Malackowski | 7,108,709 B2 | 9/2006 | Cummins |
| 6,550,546 | B2 | 4/2003 | Thurler et al. | 7,114,642 B2 | 10/2006 | Whitman |
| 6,592,597 | B2 | 7/2003 | Grant et al. | 7,118,582 B1 | 10/2006 | Wang et al. |
| 6,602,252 | B2 | 8/2003 | Mollenauer | 7,128,253 B2 | 10/2006 | Mastri et al. |
| 6,616,686 | B2 | 9/2003 | Coleman et al. | 7,128,254 B2 | 10/2006 | Shelton, IV et al. |
| 6,619,529 | B2 | 9/2003 | Green et al. | 7,140,527 B2 | 11/2006 | Ehrenfels et al. |
| 6,620,166 | B1 | 9/2003 | Wenstrom, Jr. et al. | 7,143,924 B2 | 12/2006 | Scirica et al. |
| 6,629,988 | B2 | 10/2003 | Weadock | 7,143,925 B2 | 12/2006 | Shelton, IV et al. |
| 6,644,532 | B2 | 11/2003 | Green et al. | 7,143,926 B2 | 12/2006 | Shelton, IV et al. |
| 6,656,193 | B2 | 12/2003 | Grant et al. | 7,159,750 B2 | 1/2007 | Racenet et al. |
| 6,669,073 | B2 | 12/2003 | Milliman et al. | 7,168,604 B2 | 1/2007 | Milliman et al. |
| 6,681,978 | B2 | 1/2004 | Geiste et al. | 7,188,758 B2 | 3/2007 | Viola et al. |
| 6,681,979 | B2 | 1/2004 | Whitman | 7,207,471 B2 | 4/2007 | Heinrich et al. |
| 6,695,199 | B2 | 2/2004 | Whitman | 7,207,472 B2 | 4/2007 | Wukusick et al. |
| 6,698,643 | B2 | 3/2004 | Whitman | 7,210,609 B2 | 5/2007 | Leiboff et al. |
| 6,705,503 | B1 | 3/2004 | Pedicini et al. | 7,220,272 B2 | 5/2007 | Weadock |
| 6,716,232 | B1 | 4/2004 | Vidal et al. | 7,225,964 B2 | 6/2007 | Mastri et al. |
| 6,716,233 | B1 | 4/2004 | Whitman | 7,246,734 B2 | 7/2007 | Shelton, IV |
| 6,752,816 | B2 | 6/2004 | Culp et al. | 7,258,262 B2 | 8/2007 | Mastri et al. |
| 6,755,338 | B2 | 6/2004 | Hahnen et al. | 7,300,450 B2 | 11/2007 | Vleugels et al. |
| 6,773,438 | B1 | 8/2004 | Knodel et al. | 7,303,108 B2 | 12/2007 | Shelton, IV |
| 6,786,382 | B1 | 9/2004 | Hoffman | 7,398,908 B2 | 7/2008 | Holsten et al. |
| 6,793,652 | B1 | 9/2004 | Whitman et al. | 2002/0117534 A1 | 8/2002 | Green et al. |
| 6,805,273 | B2 | 10/2004 | Bilotti et al. | 2002/0165541 A1 | 11/2002 | Whitman |
| 6,806,808 | B1 | 10/2004 | Watters et al. | 2003/0105478 A1 | 6/2003 | Whitman et al. |
| 6,814,741 | B2 | 11/2004 | Bowman et al. | 2003/0130677 A1 | 7/2003 | Whitman et al. |
| 6,817,508 | B1 | 11/2004 | Racenet et al. | 2003/0216778 A1 | 11/2003 | Weadock |
| 6,817,509 | B2 | 11/2004 | Geiste et al. | 2004/0028502 A1 | 2/2004 | Cummins |
| 6,821,273 | B2 | 11/2004 | Mollenauer | 2004/0094597 A1 | 5/2004 | Whitman et al. |
| 6,828,902 | B2 | 12/2004 | Casden | 2004/0097987 A1 | 5/2004 | Pugsley et al. |
| 6,830,174 | B2 | 12/2004 | Hillstead et al. | 2004/0108357 A1 | 6/2004 | Milliman et al. |
| 6,835,199 | B2 | 12/2004 | McGuckin, Jr. et al. | 2004/0111081 A1 | 6/2004 | Whitman et al. |
| 6,843,403 | B2 * | 1/2005 | Whitman ................ 227/176.1 | 2004/0116952 A1 | 6/2004 | Sakurai et al. |
| 6,846,307 | B2 | 1/2005 | Whitman et al. | 2004/0122471 A1 | 6/2004 | Toby et al. |
| 6,846,308 | B2 | 1/2005 | Whitman et al. | 2004/0164123 A1 | 8/2004 | Racenet et al. |
| 6,846,309 | B2 | 1/2005 | Whitman et al. | 2004/0167572 A1 | 8/2004 | Roth et al. |
| 6,849,071 | B2 | 2/2005 | Whitman et al. | 2004/0173659 A1 | 9/2004 | Green et al. |
| RE38,708 | E | 3/2005 | Bolanos et al. | 2004/0222268 A1 | 11/2004 | Bilotti et al. |
| 6,877,647 | B2 | 4/2005 | Green et al. | 2004/0230214 A1 * | 11/2004 | Donofrio et al. ............ 606/169 |
| 6,905,057 | B2 | 6/2005 | Swayze et al. | 2004/0232199 A1 | 11/2004 | Shelton, IV et al. |
| 6,945,444 | B2 | 9/2005 | Gresham et al. | 2004/0232201 A1 | 11/2004 | Wenchell et al. |
| 6,953,138 | B1 | 10/2005 | Dworak et al. | 2004/0243151 A1 | 12/2004 | Demmy et al. |
| 6,953,139 | B2 | 10/2005 | Milliman et al. | 2004/0243176 A1 | 12/2004 | Hahnen et al. |
| 6,959,852 | B2 | 11/2005 | Shelton, IV et al. | 2004/0254608 A1 | 12/2004 | Huitema et al. |

| | | |
|---|---|---|
| 2005/0006430 A1* | 1/2005 | Wales ..................... 227/175.1 |
| 2005/0006434 A1 | 1/2005 | Wales et al. |
| 2005/0021026 A1 | 1/2005 | Baily |
| 2005/0023324 A1 | 2/2005 | Doll et al. |
| 2005/0033357 A1 | 2/2005 | Braun |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0143759 A1 | 6/2005 | Kelly |
| 2005/0145671 A1 | 7/2005 | Viola |
| 2005/0165415 A1 | 7/2005 | Wales |
| 2005/0171522 A1 | 8/2005 | Christopherson |
| 2005/0173490 A1 | 8/2005 | Shelton, IV |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0203550 A1 | 9/2005 | Laufer et al. |
| 2005/0216055 A1 | 9/2005 | Scirica et al. |
| 2005/0230453 A1 | 10/2005 | Viola |
| 2005/0263562 A1 | 12/2005 | Shelton, IV et al. |
| 2005/0263563 A1 | 12/2005 | Racenet et al. |
| 2005/0274768 A1 | 12/2005 | Cummins et al. |
| 2006/0008787 A1 | 1/2006 | Hayman et al. |
| 2006/0011699 A1 | 1/2006 | Olson et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton |
| 2006/0047303 A1 | 3/2006 | Ortiz et al. |
| 2006/0047307 A1 | 3/2006 | Ortiz et al. |
| 2006/0047308 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0087442 A1 | 4/2006 | Smith et al. |
| 2006/0097026 A1 | 5/2006 | Shelton, IV |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0142772 A1 | 6/2006 | Ralph et al. |
| 2006/0151567 A1 | 7/2006 | Roy |
| 2006/0190028 A1 | 8/2006 | Wales et al. |
| 2006/0190029 A1 | 8/2006 | Wales |
| 2006/0190031 A1 | 8/2006 | Wales et al. |
| 2006/0226196 A1 | 10/2006 | Hueil et al. |
| 2006/0229665 A1 | 10/2006 | Wales et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0293818 A1* | 12/2006 | Lu et al. ..................... 701/41 |
| 2007/0027469 A1 | 2/2007 | Smith et al. |
| 2007/0034666 A1 | 2/2007 | Holsten et al. |
| 2007/0034668 A1 | 2/2007 | Holsten et al. |
| 2007/0045379 A1 | 3/2007 | Shelton |
| 2007/0073340 A1 | 3/2007 | Shelton, IV et al. |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0102476 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 9412228 U | 9/1994 |
| DE | 69328576 T2 | 1/2001 |
| DE | 20112837 U1 | 10/2001 |
| DE | 20121753 U1 | 4/2003 |

| | | | | | | |
|---|---|---|---|---|---|---|
| DE | 10314072 | A1 | 10/2004 | JP | 2001286477 A | 10/2001 |
| EP | 0122046 | A1 | 10/1984 | JP | 2002369820 A | 12/2002 |
| EP | 0033548 | B1 | 5/1986 | JP | 2005505322 T | 2/2005 |
| EP | 0639349 | A2 | 2/1994 | JP | 2005103293 A | 4/2005 |
| EP | 0593920 | A1 | 4/1994 | RU | 2187249 C2 | 8/2002 |
| EP | 0600182 | A2 | 6/1994 | RU | 2225170 C2 | 3/2004 |
| EP | 0630612 | A1 | 12/1994 | SU | 1377053 A1 | 2/1988 |
| EP | 0634144 | A1 | 1/1995 | SU | 1561964 A1 | 5/1990 |
| EP | 0646356 | A2 | 4/1995 | SU | 1722476 A1 | 3/1992 |
| EP | 0646357 | A1 | 4/1995 | WO | WO 93/08755 A1 | 5/1993 |
| EP | 0669104 | A1 | 8/1995 | WO | WO 95/18572 A1 | 7/1995 |
| EP | 0679367 | A2 | 11/1995 | WO | WO 95/29639 A1 | 11/1995 |
| EP | 0392547 | B1 | 12/1995 | WO | WO 96/35464 A1 | 11/1996 |
| EP | 0685204 | A1 | 12/1995 | WO | WO 98/30153 A1 | 7/1998 |
| EP | 0699418 | A1 | 3/1996 | WO | WO 99/12483 A1 | 3/1999 |
| EP | 0702937 | A1 | 3/1996 | WO | WO 99/15086 A1 | 4/1999 |
| EP | 0705571 | A1 | 4/1996 | WO | WO 99/34744 A1 | 7/1999 |
| EP | 0484677 | B2 | 6/1996 | WO | WO 00/57796 A1 | 10/2000 |
| EP | 0541987 | B1 | 7/1996 | WO | WO 00/64365 A1 | 11/2000 |
| EP | 0667119 | B1 | 7/1996 | WO | WO 00/72762 A1 | 12/2000 |
| EP | 0770355 | A1 | 5/1997 | WO | WO 00/72765 A1 | 12/2000 |
| EP | 0503662 | B1 | 6/1997 | WO | WO 01/05702 A1 | 1/2001 |
| EP | 0625335 | B1 | 11/1997 | WO | WO 01/10482 A1 | 2/2001 |
| EP | 0552423 | B1 | 1/1998 | WO | WO 01/62158 A2 | 8/2001 |
| EP | 0592244 | B1 | 1/1998 | WO | WO 01/62162 A1 | 8/2001 |
| EP | 0648476 | B1 | 1/1998 | WO | WO 01/62164 A2 | 8/2001 |
| EP | 0603472 | B1 | 11/1998 | WO | WO 01/91646 A1 | 12/2001 |
| EP | 0878169 | A1 | 11/1998 | WO | WO 02/17799 A1 | 3/2002 |
| EP | 0760230 | B1 | 2/1999 | WO | WO 02/19920 A1 | 3/2002 |
| EP | 0537572 | B1 | 6/1999 | WO | WO 02/30297 A2 | 4/2002 |
| EP | 0552050 | B1 | 5/2000 | WO | WO 02/32322 A2 | 4/2002 |
| EP | 1090592 | A1 | 4/2001 | WO | WO 02/043571 A2 | 6/2002 |
| EP | 1256318 | B1 | 5/2001 | WO | WO 02/067785 A2 | 9/2002 |
| EP | 0908152 | B1 | 1/2002 | WO | WO 02/098302 A1 | 12/2002 |
| EP | 0872213 | B1 | 5/2002 | WO | WO 03/000138 A2 | 1/2003 |
| EP | 1238634 | A2 | 9/2002 | WO | WO 03/001329 A2 | 1/2003 |
| EP | 0656188 | B1 | 1/2003 | WO | WO 03/013363 A1 | 2/2003 |
| EP | 0829235 | B1 | 6/2003 | WO | WO 03/020106 A2 | 3/2003 |
| EP | 0813843 | B1 | 10/2003 | WO | WO 03/079909 A3 | 3/2003 |
| EP | 0705570 | B1 | 4/2004 | WO | WO 03/030743 A2 | 4/2003 |
| EP | 1086713 | B1 | 5/2004 | WO | WO 03/037193 A1 | 5/2003 |
| EP | 1426012 | A1 | 6/2004 | WO | WO 03/047436 A3 | 6/2003 |
| EP | 0888749 | B1 | 9/2004 | WO | WO 03/057048 A1 | 7/2003 |
| EP | 1477119 | A1 | 11/2004 | WO | WO 03/057058 A1 | 7/2003 |
| EP | 1479345 | A1 | 11/2004 | WO | WO 03/063694 A1 | 8/2003 |
| EP | 1479347 | A1 | 11/2004 | WO | WO 03/077769 A1 | 9/2003 |
| EP | 1479348 | A1 | 11/2004 | WO | WO 03/082126 A1 | 10/2003 |
| EP | 1520523 | A1 | 4/2005 | WO | WO 03/088845 A2 | 10/2003 |
| EP | 1520525 | A1 | 4/2005 | WO | WO 03/090630 A2 | 11/2003 |
| EP | 1522264 | A1 | 4/2005 | WO | WO 03/094743 A1 | 11/2003 |
| EP | 1550408 | A1 | 7/2005 | WO | WO 03/094745 A1 | 11/2003 |
| EP | 1557129 | A1 | 7/2005 | WO | WO 03/094746 A1 | 11/2003 |
| EP | 1064883 | B1 | 8/2005 | WO | WO 03/094747 A1 | 11/2003 |
| EP | 1621141 | A2 | 2/2006 | WO | WO 03/101313 A1 | 12/2003 |
| EP | 1652481 | A2 | 5/2006 | WO | WO 03/105702 A2 | 12/2003 |
| EP | 1382303 | B1 | 6/2006 | WO | WO 2004/006980 A2 | 1/2004 |
| EP | 1045672 | B1 | 8/2006 | WO | WO 2004/032754 A2 | 4/2004 |
| EP | 1617768 | B1 | 8/2006 | WO | WO 2004/032760 A2 | 4/2004 |
| EP | 1702567 | A2 | 9/2006 | WO | WO 2004/032762 A1 | 4/2004 |
| EP | 1129665 | B1 | 11/2006 | WO | WO 2004/032763 A2 | 4/2004 |
| EP | 1256317 | B1 | 12/2006 | WO | WO 2004/047653 A2 | 6/2004 |
| EP | 1728473 | A1 | 12/2006 | WO | WO 2004/049956 A2 | 6/2004 |
| EP | 1728475 | A2 | 12/2006 | WO | WO 2004086987 A1 * | 10/2004 |
| EP | 1479346 | B1 | 1/2007 | WO | WO 2004/096057 A2 | 11/2004 |
| EP | 1484024 | B1 | 1/2007 | WO | WO 2004/112618 A2 | 12/2004 |
| EP | 1300117 | B1 | 8/2007 | WO | WO 2004/112652 A2 | 12/2004 |
| FR | 1112936 | A | 3/1956 | WO | WO 2005/027983 A2 | 3/2005 |
| GB | 939929 | A | 10/1963 | WO | WO 2005/096954 A2 | 10/2005 |
| GB | 2336214 | A | 10/1999 | WO | WO 2005/115251 A2 | 12/2005 |
| JP | 6007357 | A | 1/1994 | WO | WO 2006/044490 A2 | 4/2006 |
| JP | 7051273 | A | 2/1995 | WO | WO 2006/044581 A2 | 4/2006 |
| JP | 8033641 | A | 2/1996 | WO | WO 2006/044810 A2 | 4/2006 |
| JP | 8229050 | A | 9/1996 | WO | WO 2006/083748 A1 | 8/2006 |

| WO | WO 2006/132992 A1 | 12/2006 |
| WO | WO 2007/016290 A2 | 2/2007 |

OTHER PUBLICATIONS

Office Action issued on Jun. 13, 2007 in U.S. Appl. No. 11/343,447.
Office Action issued on Mar. 7, 2007 in U.S. Appl. No. 11/343,573.
Office Action issued on Jul. 5, 2007 in U.S. Appl. No. 11/343,498.
Office Action issued on Jun. 28, 2007 in U.S. Appl. No. 11/344,024.
Office Action issued on Apr. 5, 2007 in U.S. Appl. No. 11/343,321.
Office Action issued on May 16, 2007 in U.S. Appl. No. 11/343,563.
Office Action issued on Feb. 2, 2007 in U.S. Appl. No. 11/344,020.
Office Action issued on Feb. 13, 2007 in U.S. Appl. No. 11/344,021.
Office Action issued on Jun. 18, 2007 in U.S. Appl. No. 11/343,545.
Office Action issued on Jun. 25, 2007 in U.S. Appl. No. 11/343,546.
Office Action issued on Jul. 19, 2007 in U.S. Appl. No. 11/344,021.
Office Action issued on Jul. 20, 2007 in U.S. Appl. No. 11/344,035.
Office Action issued on Jul. 25, 2007 in U.S. Appl. No. 11/344,020.
Office Action issued on Aug. 8, 2007 in U.S. Appl. No. 11/343,573.
European Search Report Application No. 07250392.3, dated Jul. 2, 2007 (9 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

* cited by examiner

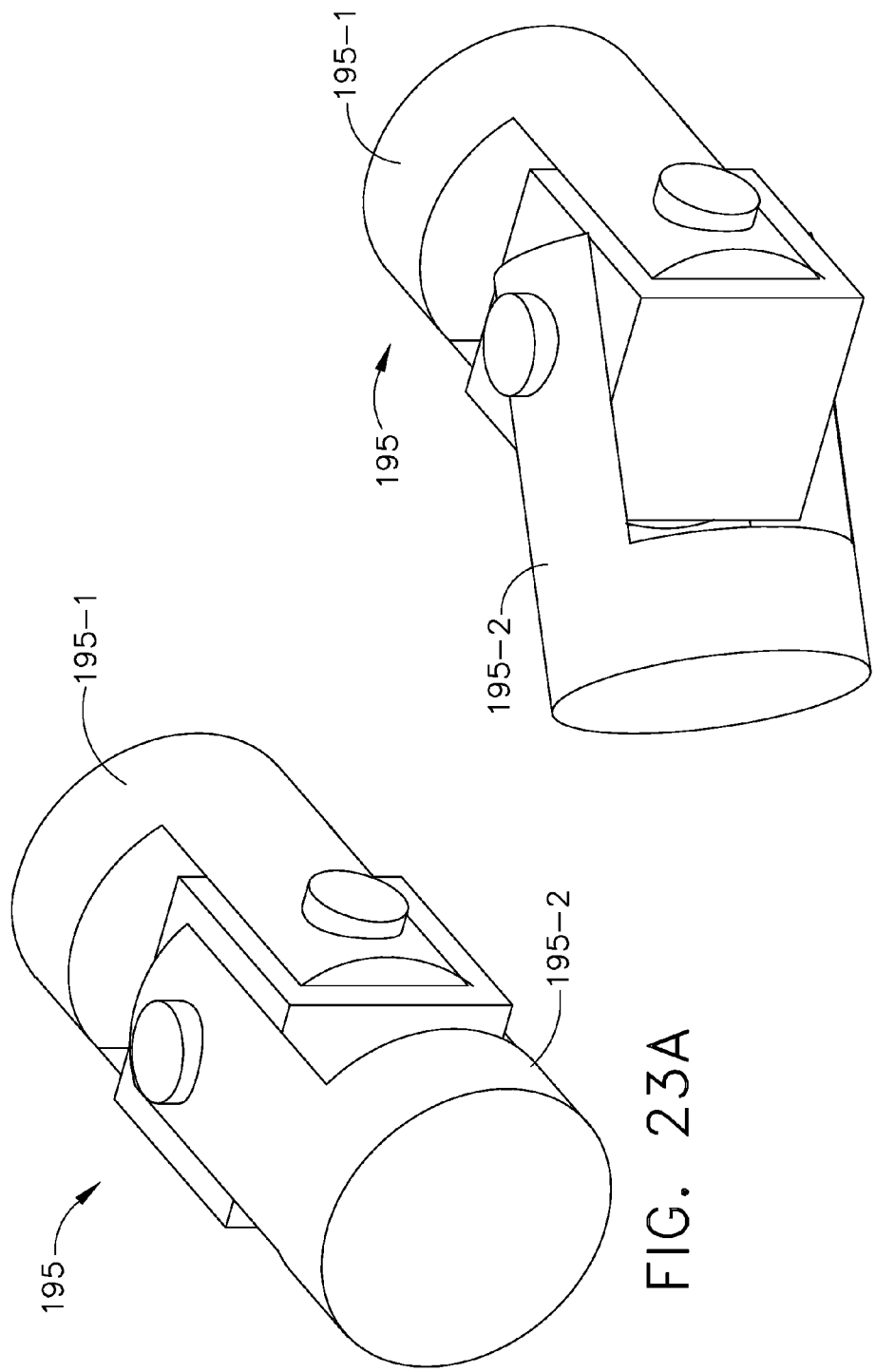

MOTOR-DRIVEN SURGICAL CUTTING AND FASTENING INSTRUMENT WITH ARTICULATABLE END EFFECTOR

CROSS-REFERENCE TO RELATED APPLICATIONS

The present application is related to the following concurrently-filed U.S. patent applications, which are incorporated herein by reference:

MOTOR-DRIVEN SURGICAL CUTTING AND FASTENING INSTRUMENT WITH USER FEEDBACK SYSTEM; Inventors: Frederick E. Shelton, IV, John Ouwerkerk and Jerome R. Morgan, Ser. No. 11/343,498

MOTOR-DRIVEN SURGICAL CUTTING AND FASTENING INSTRUMENT WITH LOADING FORCE FEEDBACK; Inventors: Frederick E. Shelton, IV, John N. Ouwerkerk, Jerome R. Morgan, and Jeffrey S. Swayze, Ser. No. 11/343,573.

MOTOR-DRIVEN SURGICAL CUTTING AND FASTENING INSTRUMENT WITH TACTILE POSITION FEEDBACK; Inventors: Frederick E. Shelton, IV, John N. Ouwerkerk, Jerome R. Morgan, and Jeffrey S. Swayze, Ser. No. 11/344,035.

MOTOR-DRIVEN SURGICAL CUTTING AND FASTENING INSTRUMENT WITH ADAPTIVE USER FEEDBACK; Inventors: Frederick E. Shelton, IV, John N. Ouwerkerk, and Jerome R. Morgan, Ser. No. 11/343,447.

MOTOR-DRIVEN SURGICAL CUTTING AND FASTENING INSTRUMENT WITH MECHANICAL CLOSURE SYSTEM; Inventors: Frederick E. Shelton, IV and Christoph L. Gillum, Ser. No. 11/344,024.

SURGICAL CUTTING AND FASTENING INSTRUMENT WITH CLOSURE TRIGGER LOCKING MECHANISM; Inventors: Frederick E. Shelton, IV and Kevin R. Doll, Ser. No. 11/343,321.

GEARING SELECTOR FOR A POWERED SURGICAL CUTTING AND FASTENING STAPLING INSTRUMENT; Inventors: Frederick E. Shelton, IV, Jeffrey S. Swayze, Eugene L. Timperman, Ser. No. 11/343,563.

SURGICAL INSTRUMENT HAVING RECORDING CAPABILITIES; Inventors: Frederick E. Shelton, IV, John N. Ouwerkerk, and Eugene L. Timperman, Ser. No. 11/343,803.

SURGICAL INSTRUMENT HAVING A REMOVABLE BATTERY; Inventors: Frederick E. Shelton, IV, Kevin R. Doll, Jeffrey S. Swayze and Eugene Timperman, Ser. No. 11/344,020.

ELECTRONIC LOCKOUTS AND SURGICAL INSTRUMENT INCLUDING SAME; Inventors: Jeffrey S. Swayze, Frederick E. Shelton, IV, Kevin R. Doll, Ser. No. 11/343,439.

ENDOSCOPIC SURGICAL INSTRUMENT WITH A HANDLE THAT CAN ARTICULATE WITH RESPECT TO THE SHAFT; Inventors: Frederick E. Shelton, IV, Jeffrey S. Swayze, Mark S. Ortiz, and Leslie M. Fugikawa, Ser. No. 11/343,547.

ELECTRO-MECHANICAL SURGICAL CUTTING AND FASTENING INSTRUMENT HAVING A ROTARY FIRING AND CLOSURE SYSTEM WITH PARALLEL CLOSURE AND ANVIL ALIGNMENT COMPONENTS; Inventors: Frederick E. Shelton, IV, Stephen J. Balek and Eugene L. Timperman, Ser. No. 11/344,021

DISPOSABLE STAPLE CARTRIDGE HAVING AN ANVIL WITH TISSUE LOCATOR FOR USE WITH A SURGICAL CUTTING AND FASTENING INSTRUMENT AND MODULAR END EFFECTOR SYSTEM THEREFOR; Inventors: Frederick E. Shelton, IV, Michael S. Cropper, Joshua M. Broehl, Ryan S. Crisp, Jamison J. Float, Eugene L. Timperman, Ser. No. 11/343,546

SURGICAL INSTRUMENT HAVING A FEEDBACK SYSTEM; Inventors: Frederick E. Shelton, IV, Jerome R. Morgan, Kevin R. Doll, Jeffrey S. Swayze and Eugene Timperman, Ser. No. 11/343,545

BACKGROUND

The present invention generally concerns surgical cutting and fastening instruments and, more particularly, motor-driven surgical cutting and fastening instruments.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, or multiple firing strokes, depending on the device. Firing the surgical stapler causes severing and stapling the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest for lower force-to-fire (FTF) to a level that all or a great majority of surgeons can handle. One known solution to lower FTF it use $CO_2$ or electrical motors. These devices have not faired much better than traditional hand-powered devices, but for a different reason. Surgeons typically prefer to experience proportionate force distribution to that being experienced by the end-effector in the forming the staple to assure them that the cutting/stapling cycle is complete, with the upper limit within the capabilities of most surgeons (usually around 15-30 lbs). They also typically want to maintain control of deploying the staple and being able to stop at anytime if the forces felt in the handle of the device feel too great or for some other clinical reason. These user-feedback effects are not suitably realizable in present motor-driven endocutters. As a result, there is a general lack of acceptance by physicians of motor-drive endocutters where the cutting/stapling operation is actuated by merely pressing a button.

SUMMARY

In one general aspect, the present invention is directed to a motorized surgical cutting and fastening instrument that provides feedback to the user regarding the position, force and/or deployment of the end effector. The instrument, in various embodiments, also allows the operator to control the end effector, including being able to stop deployment if so desired. The instrument may include two triggers in its handle—a closure trigger and a firing trigger—with separate actuation motions. When an operator of the instrument retracts the closure trigger, tissue positioned in the end effector may be clamped by the end effector. Then, when the operator retracts the firing trigger, a motor may power, via a gear drive train, a rotational main drive shaft assembly, which causes a cutting instrument in the end effector to sever the clamped tissue.

In various embodiments, the instrument may comprise a power assist system with loading force feedback and control to reduce the firing force required to be exerted by the operator in order to complete the cutting operation. In such embodiments, the firing trigger may be geared into the gear drive train of the main drive shaft assembly. In that way, the operator may experience feedback regarding the force being applied to the cutting instrument. That is, the loading force on the firing trigger may be related to the loading force experienced by the cutting instrument. Also in such embodiments, because the firing trigger is geared into the gear drive train, force applied by the operator may be added to the force applied to the motor.

According to various embodiments, when the firing trigger is retracted an appropriate amount (e.g., five degrees), an on/off switch may be actuated, which sends a signal to the motor to rotate at a specified rate, thus commencing actuation of the drive shaft assembly and end effector. According to other embodiments, a proportional sensor may be used. The proportional sensor may send a signal to the motor to rotate at a rate proportional to the force applied to the firing trigger by the operator. In that way, the rotational position of the firing trigger is generally proportional to where the cutting instrument is in the end effector (e.g., fully deployed or fully retracted). Further, the operator could stop retracting the firing trigger at some point in the stroke to stop the motor, and thereby stop the cutting motion. In addition, sensors may be used to detect the beginning of the stroke of the end effector (e.g., fully retracted position) and the end of the stroke (e.g., fully deployed position), respectively. Consequently, the sensors may provide an adaptive control system for controlling end effector deployment that is outside of the closed loop system of the motor, gear drive train, and end effector.

In other embodiments, the firing trigger may not be directly geared into the gear drive train used to actuate the end effector. In such embodiments, a second motor may be used to apply forces to the firing trigger to simulate the deployment of the cutting instrument in the end effector. The second motor may be controlled based on incremental rotations of the main drive shaft assembly, which may be measured by a rotary encoder. In such embodiment, the position of the rotational position of the firing trigger may be related to the position of the cutting instrument in the end effector. Additionally, an on/off switch or a proportional switch may be used to control the main motor (i.e., the motor that powers the main drive shaft).

In various implementations, the end effector may use a helical drive screw in the base of the end effector to drive the cutting instrument (e.g., knife). Also, the end effector may include a staple cartridge for stapling the severed tissue. According to other embodiments, other means for fastening (or sealing) the severed tissue may be used, including RF energy and adhesives.

Also, the instrument may include a mechanical closure system. The mechanical closure system may include an elongate channel having a clamping member, such as an anvil, pivotably connected to the channel to clamp tissue positioned in the end effector. The user may activate the clamping action of the end effector by retracting the closer trigger, which, through a mechanical closure system, causes the clamping action of the end effector. Once the clamping member is locked in place, the operator may activate the cutting operation by retracting the separate firing trigger. This may cause the cutting instrument to travel longitudinally along the channel in order to cut tissue clamped by the end effector.

In various implementations, the instrument may include a rotational main drive shaft assembly for actuating the end effector. Further, the main drive shaft may comprise an articulating joint such that the end effector may be articulated. The articulation joint may comprise, for example, a bevel gear assembly, a universal joint, or a flexible torsion cable capable of transmitting torsion force to the end effector.

Other aspects of the present invention are directed to various mechanisms for locking the closure trigger to a lower, pistol-grip portion of the handle. Such embodiments free up space in the handle directly above and behind the triggers for other components of the instrument, including components of the gear drive train and the mechanical closure system.

DRAWINGS

Various embodiments of the present invention are described herein by way of example in conjunction with the following figures, wherein FIGS. 1 and 2 are perspective views of a surgical cutting and fastening instrument according to various embodiments of the present invention;

Figures 24A, 24B:
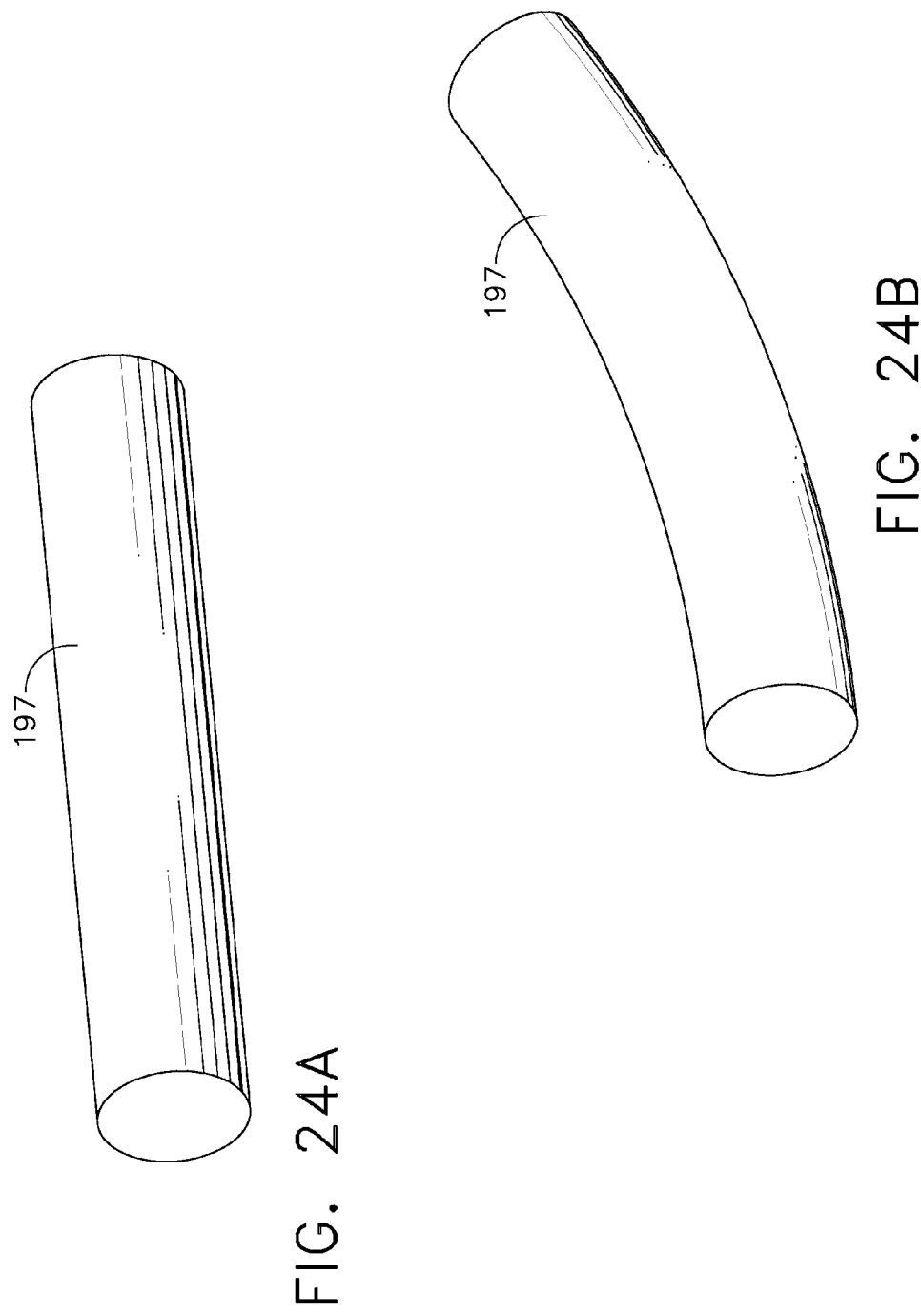
Figure 25:
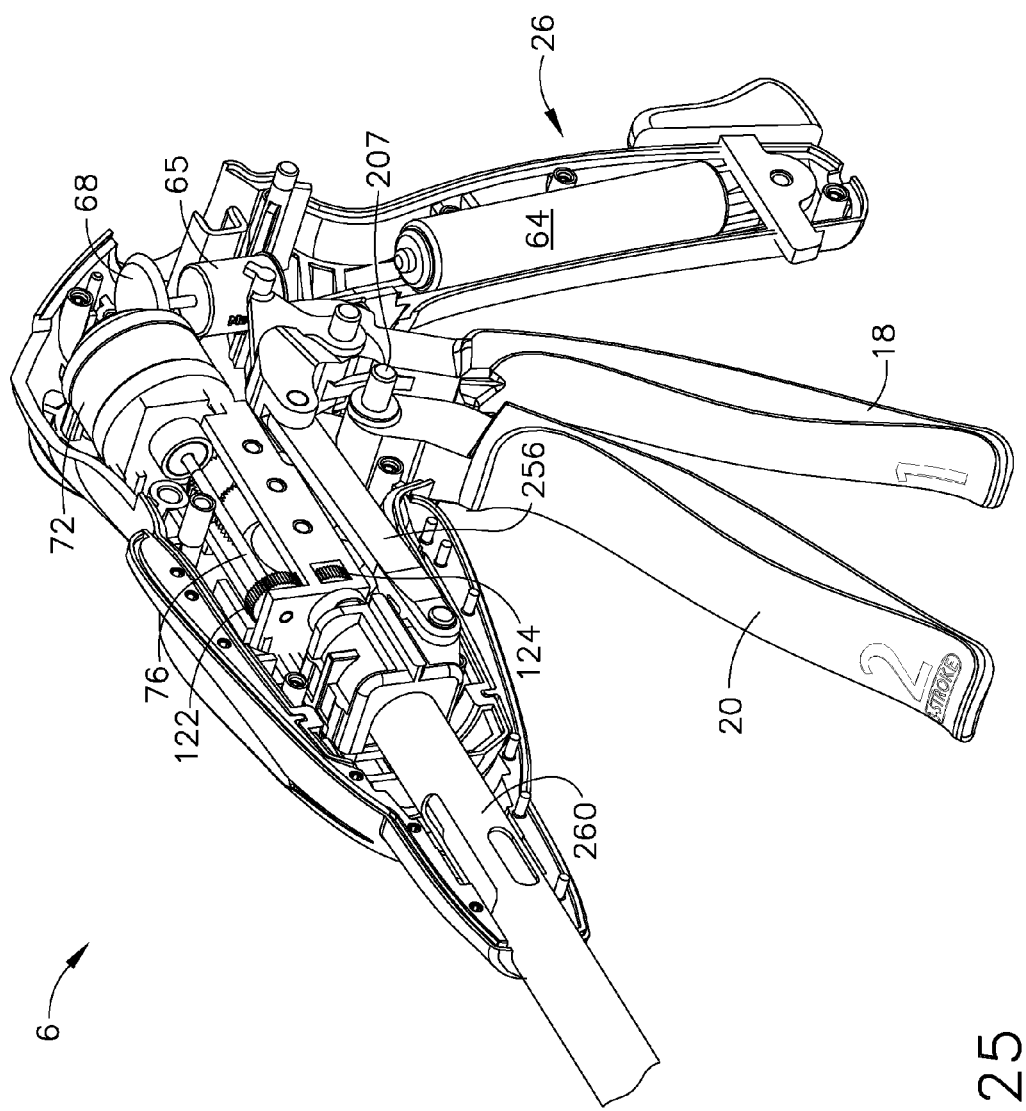
Figure 26:
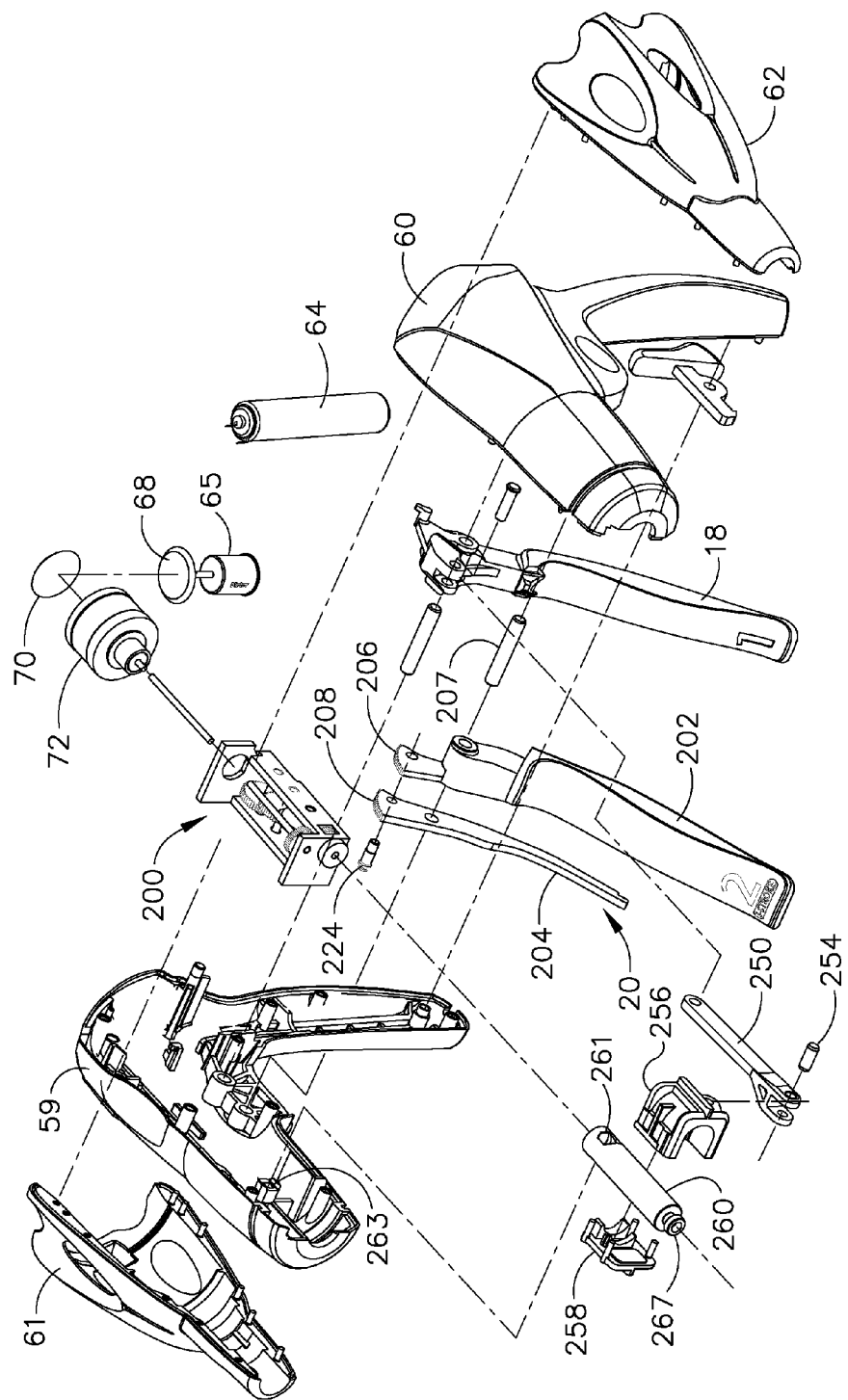
Figure 27:
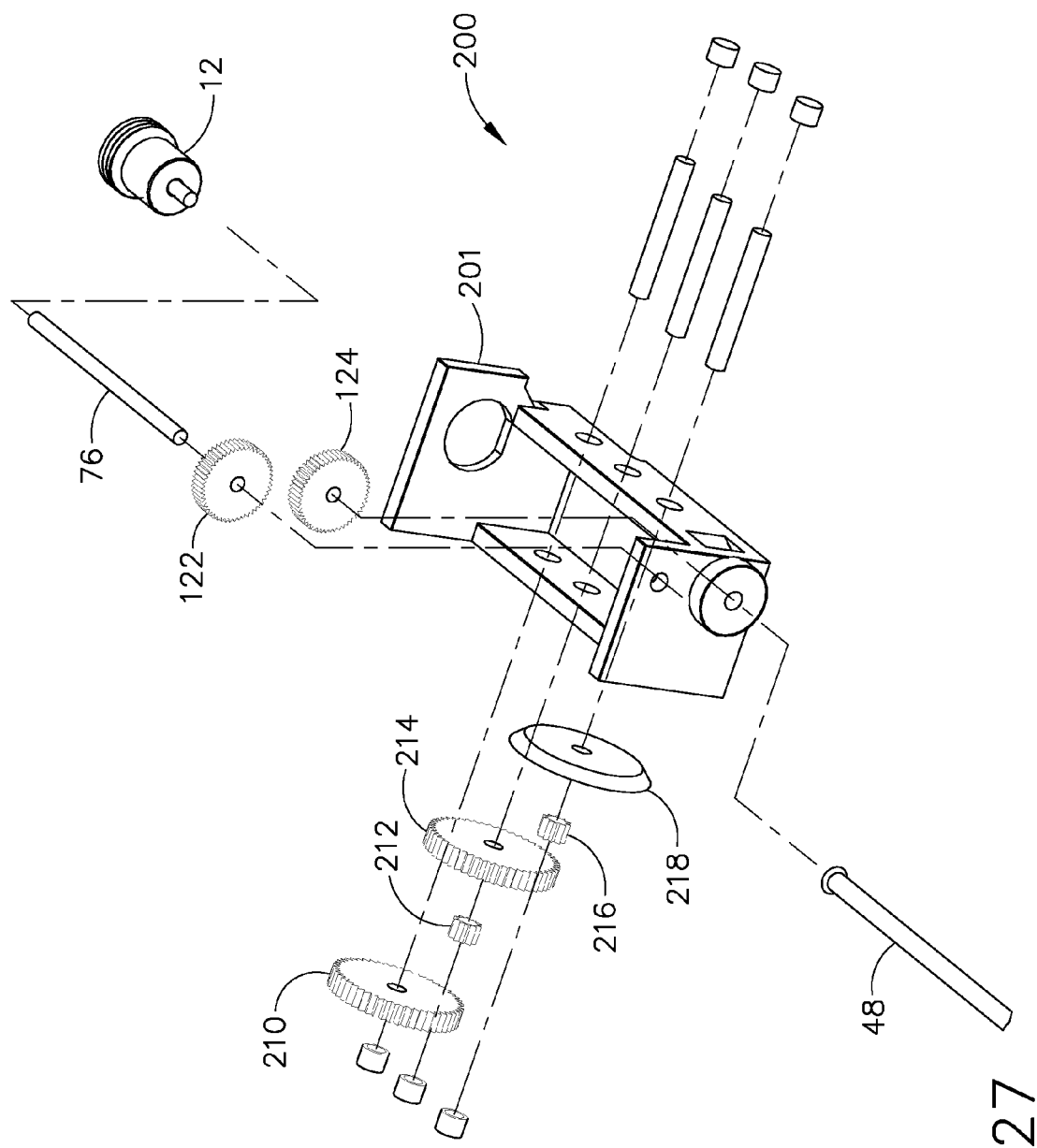
Figure 28:
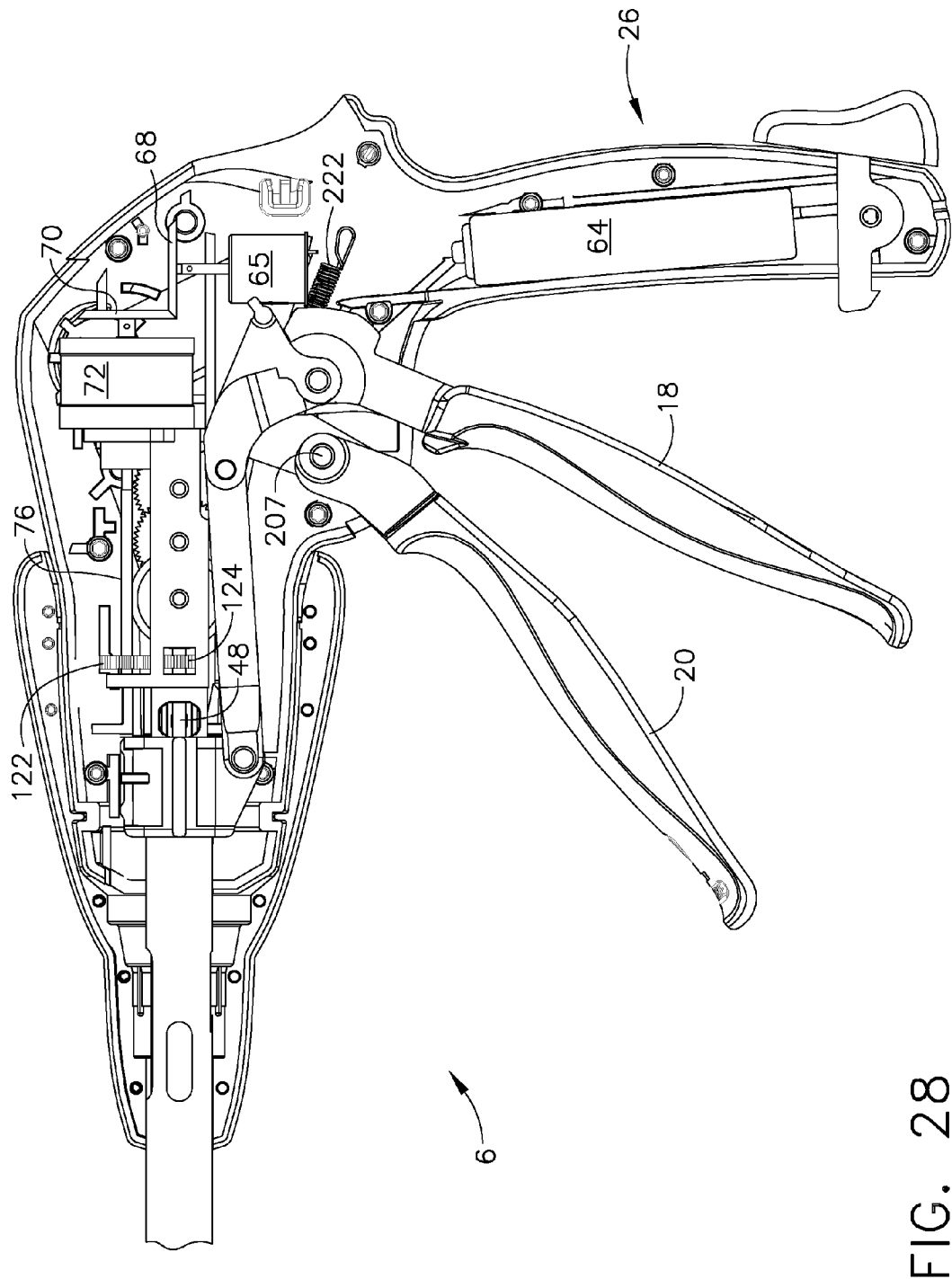
Figure 29:
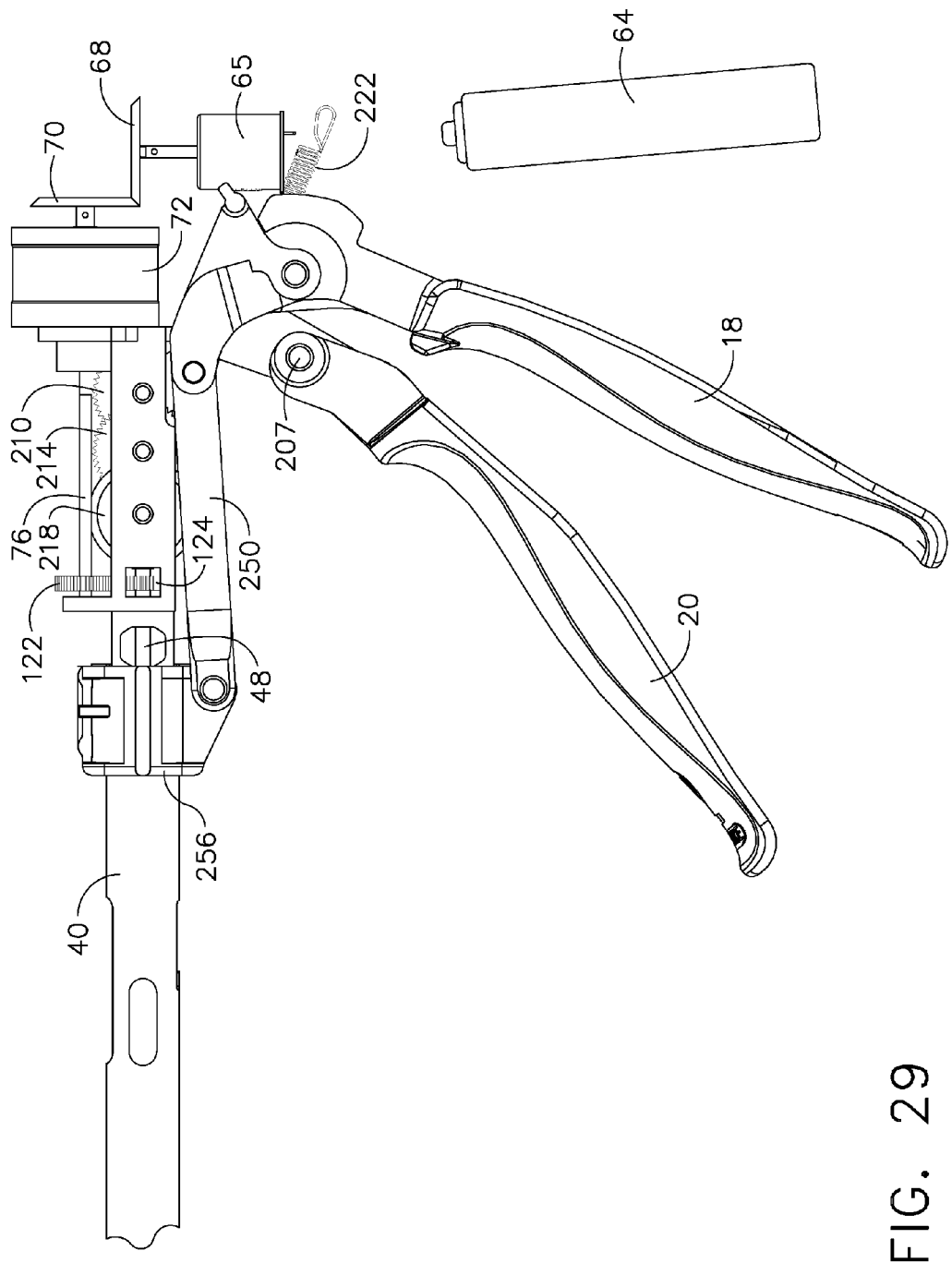
Figure 30:
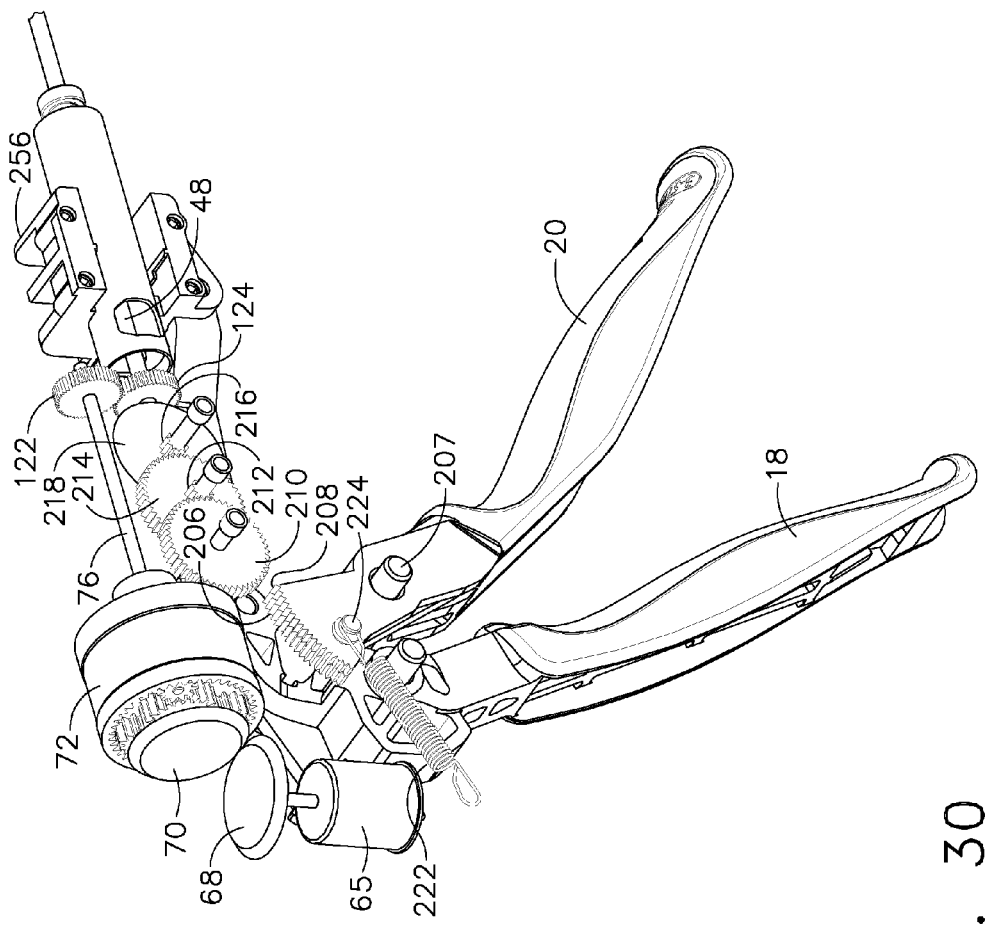
Figure 31:
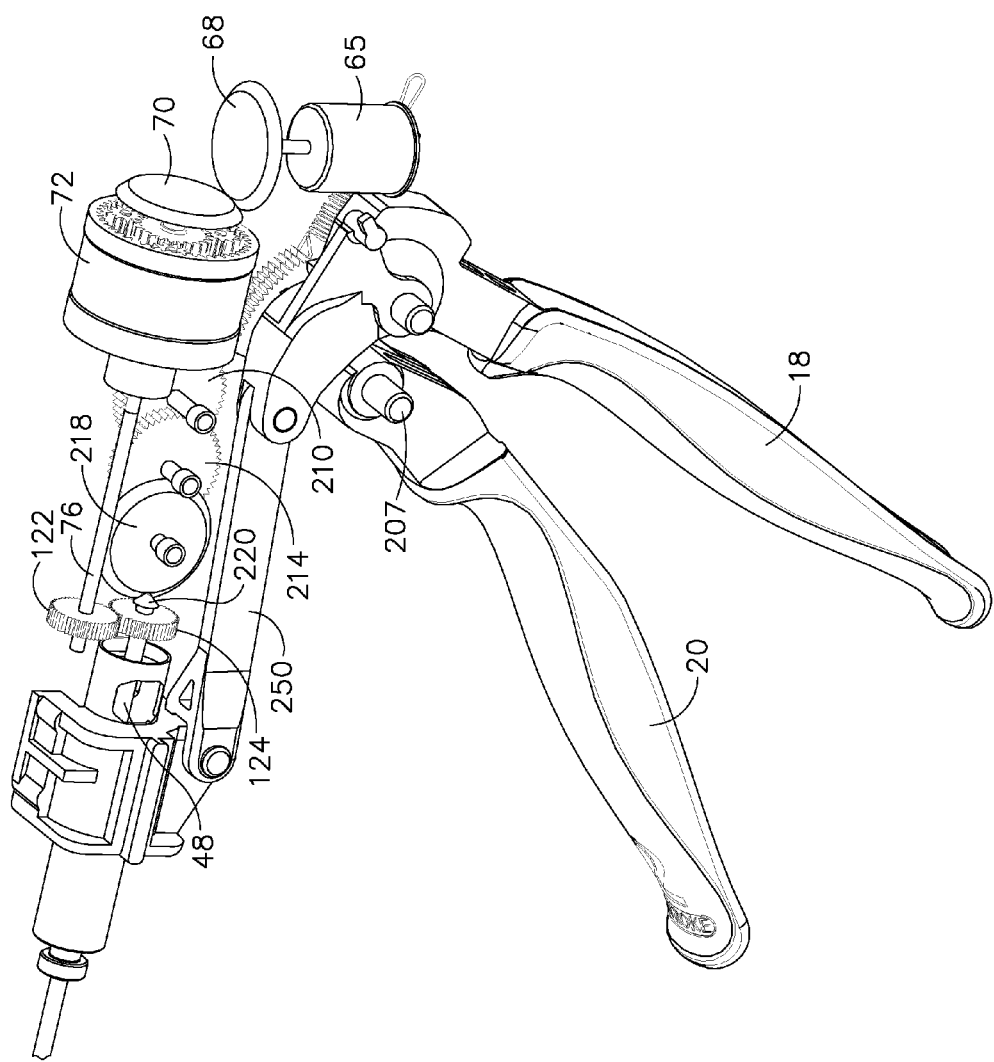
Figure 41:
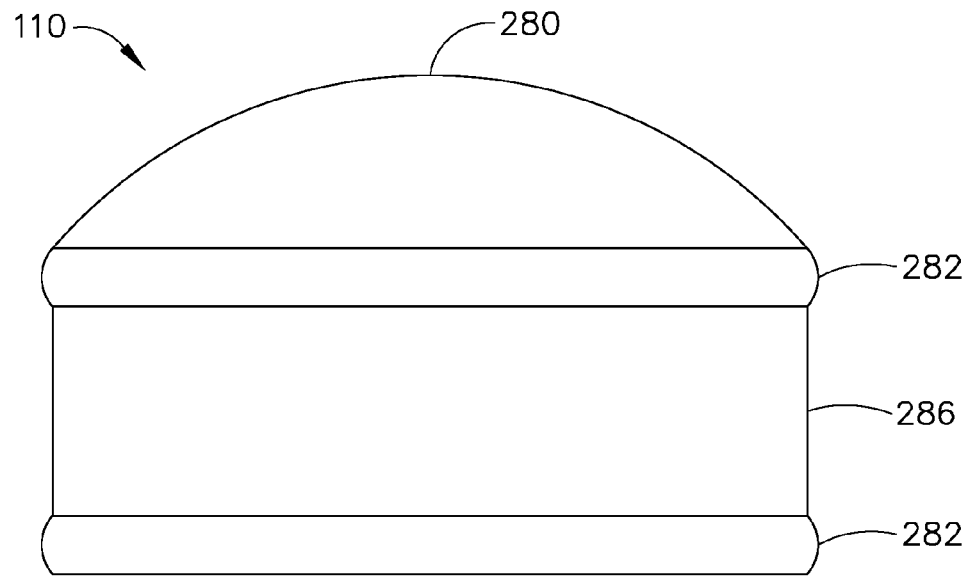
Figure 42:
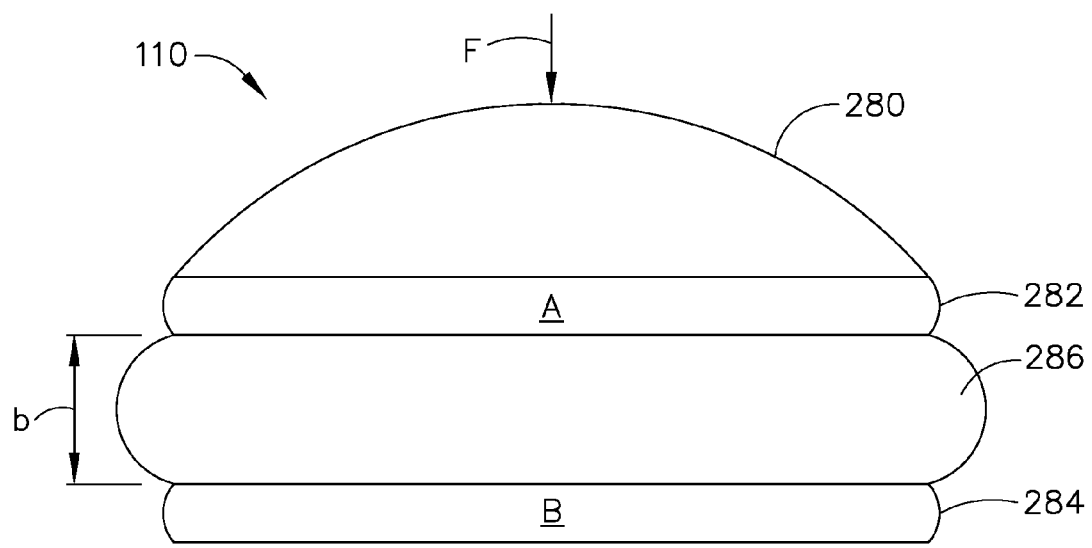

FIGS. 23A-B show a universal joint ("u-joint") that may be employed at the articulation point of the instrument according to various embodiments of the present invention;

FIGS. 24A-B shows a torsion cable that may be employed at the articulation point of the instrument according to various embodiments of the present invention;

FIGS. 25-31 illustrate a surgical cutting and fastening instrument with power assist according to another embodiment of the present invention;

FIGS. 32-36 illustrate a surgical cutting and fastening instrument with power assist according to yet another embodiment of the present invention;

FIGS. 37-40 illustrate a surgical cutting and fastening instrument with tactile feedback to embodiments of the present invention; and FIGS. 41-42 illustrate a proportional sensor that may be used according to various embodiments of the present invention.

DETAILED DESCRIPTION

Figure 1:
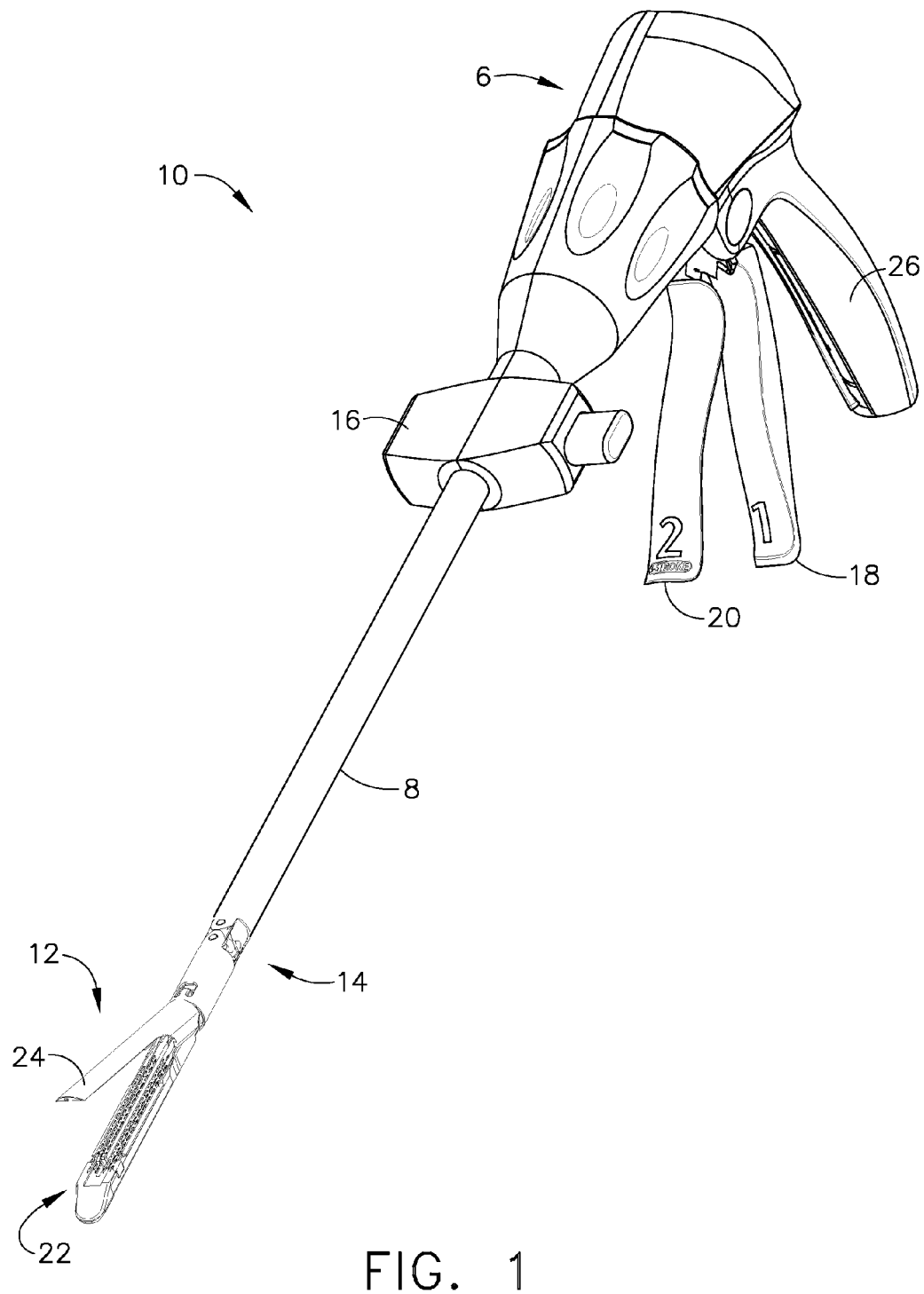
Figure 2:
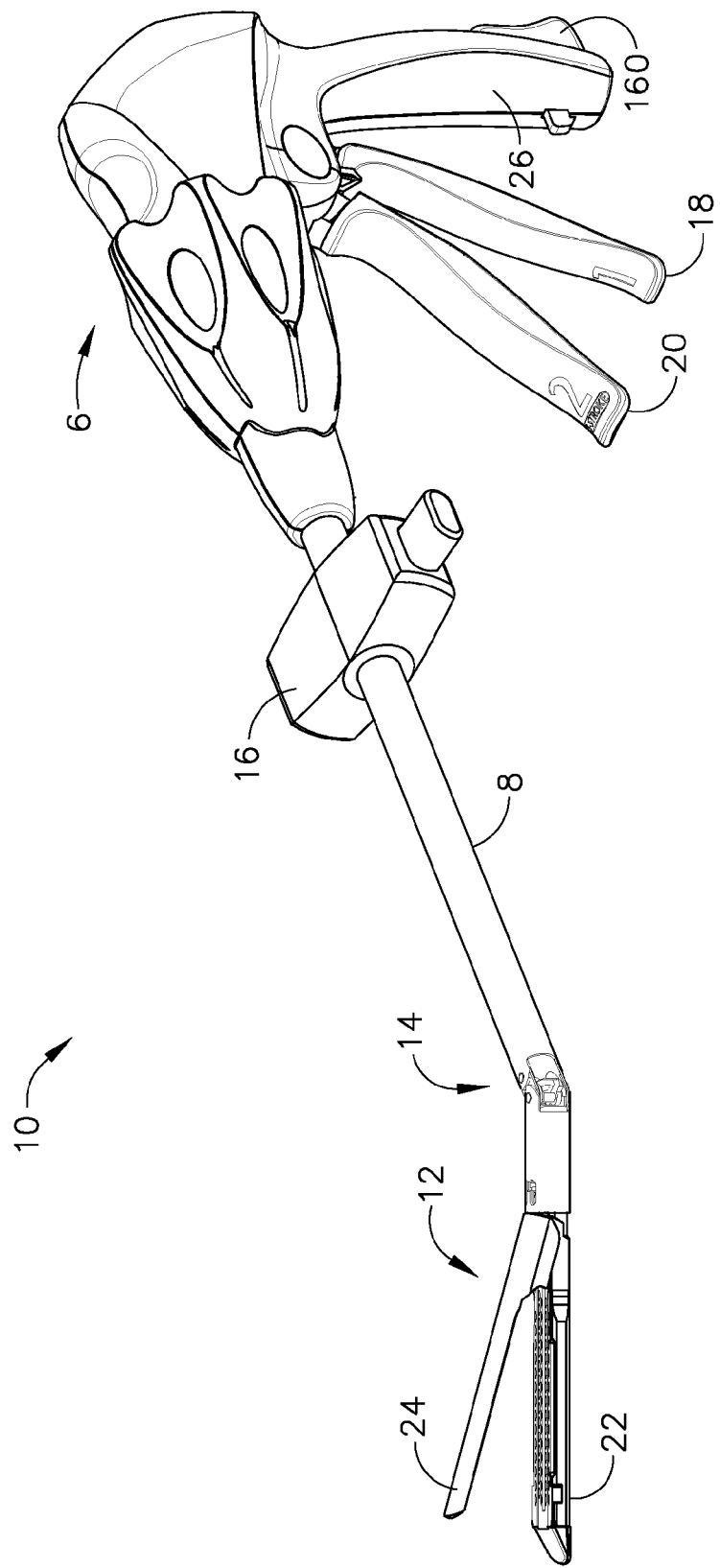

FIGS. 1 and 2 depict a surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, as a slide release button 160 shown in FIG. 14, and/or button 172 shown in FIG. 16.

Figure 3:
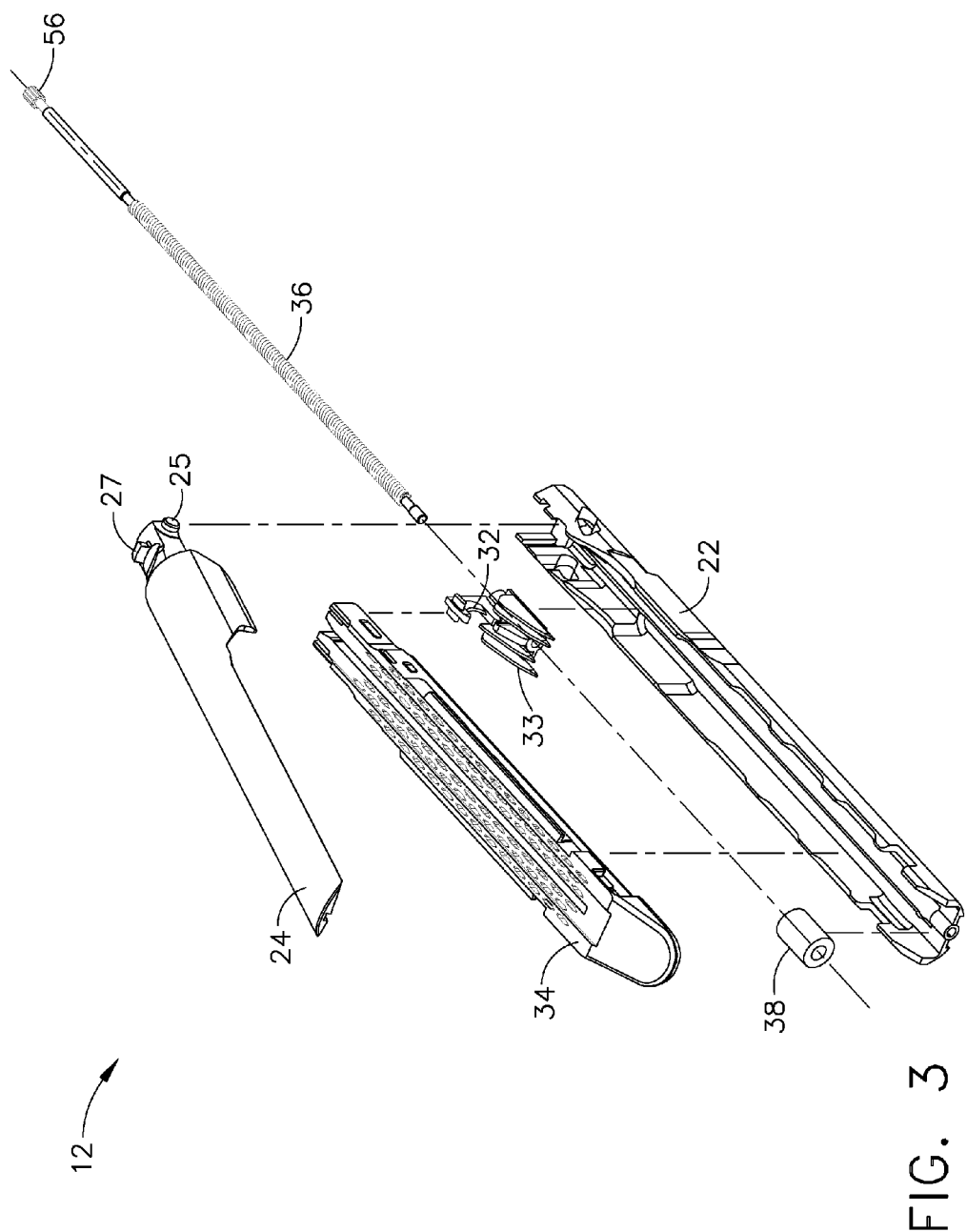
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. In various embodiments, the sled 33 maybe an integral component of the cartridge 34. U.S. Pat. No. 6,978,921, entitled "Surgical stapling instrument incorporating an E-beam firing mechanism," which is incorporated herein by reference, provides more details about such two-stroke cutting and fastening instruments. The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE" to Yates et al., and U.S. Pat. No. 5,688,270 entitled "ELECTROSURGICAL HEMOSTATIC DEVICE WITH RECESSED AND/OR OFFSET ELECTRODES" to Yates et al., which are incorporated herein by reference, disclose an endoscopic cutting instrument that uses RF energy to seal the severed tissue. U.S. patent application Ser. No. 11/267,811 to Jerome R. Morgan, et. al, and U.S. patent application Ser. No. 11/267,383 to Frederick E. Shelton, IV, et. al., which are also incorporated herein by reference, disclose an endoscopic cutting instrument that uses adhesives to fasten the severed tissue. Accordingly, although the description herein refers to cutting/stapling operations and the like below, it should be recognized that this is an exemplary embodiment and is not meant to be limiting. Other tissue-fastening techniques may also be used.

Figure 4:
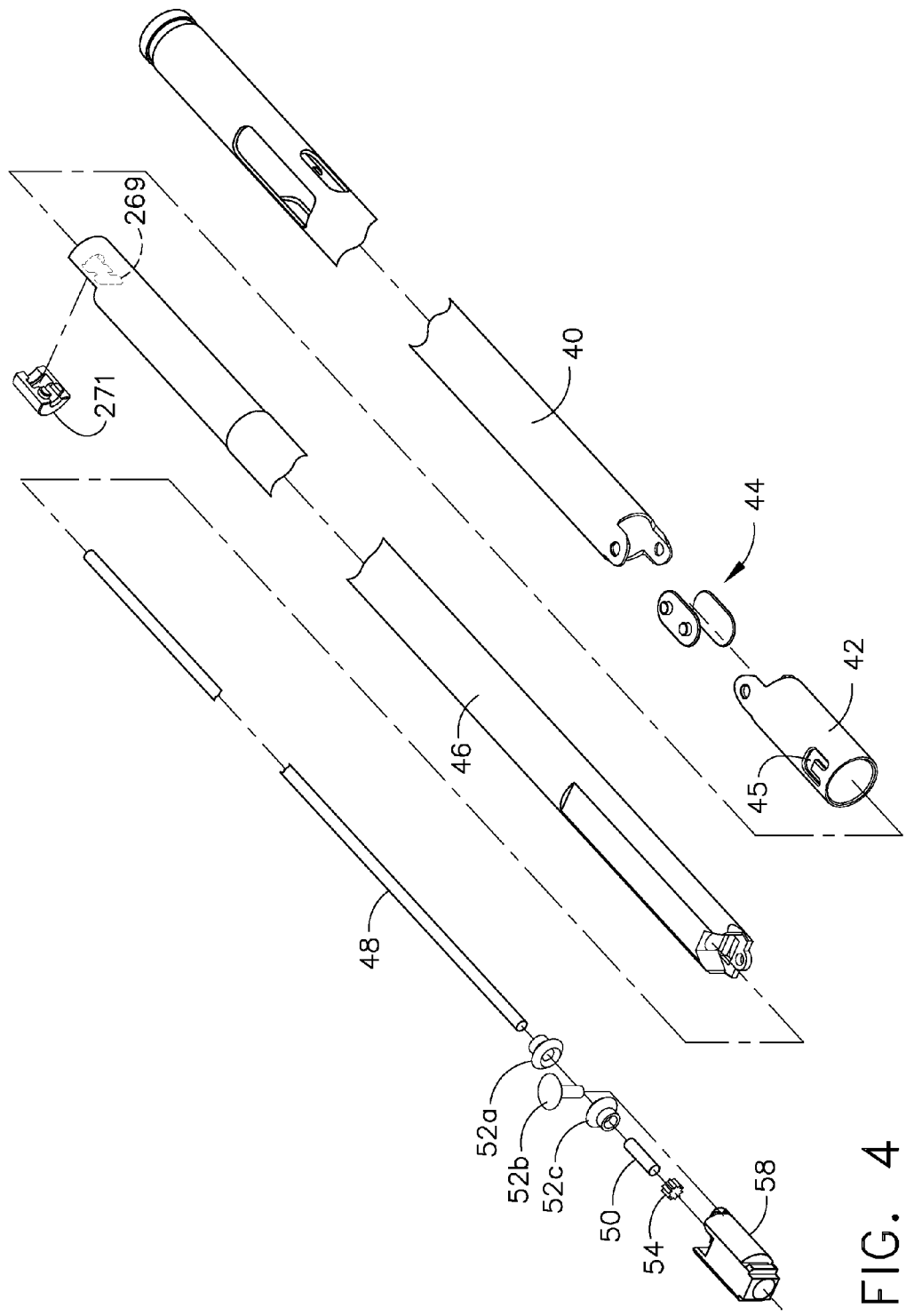
Figure 5:
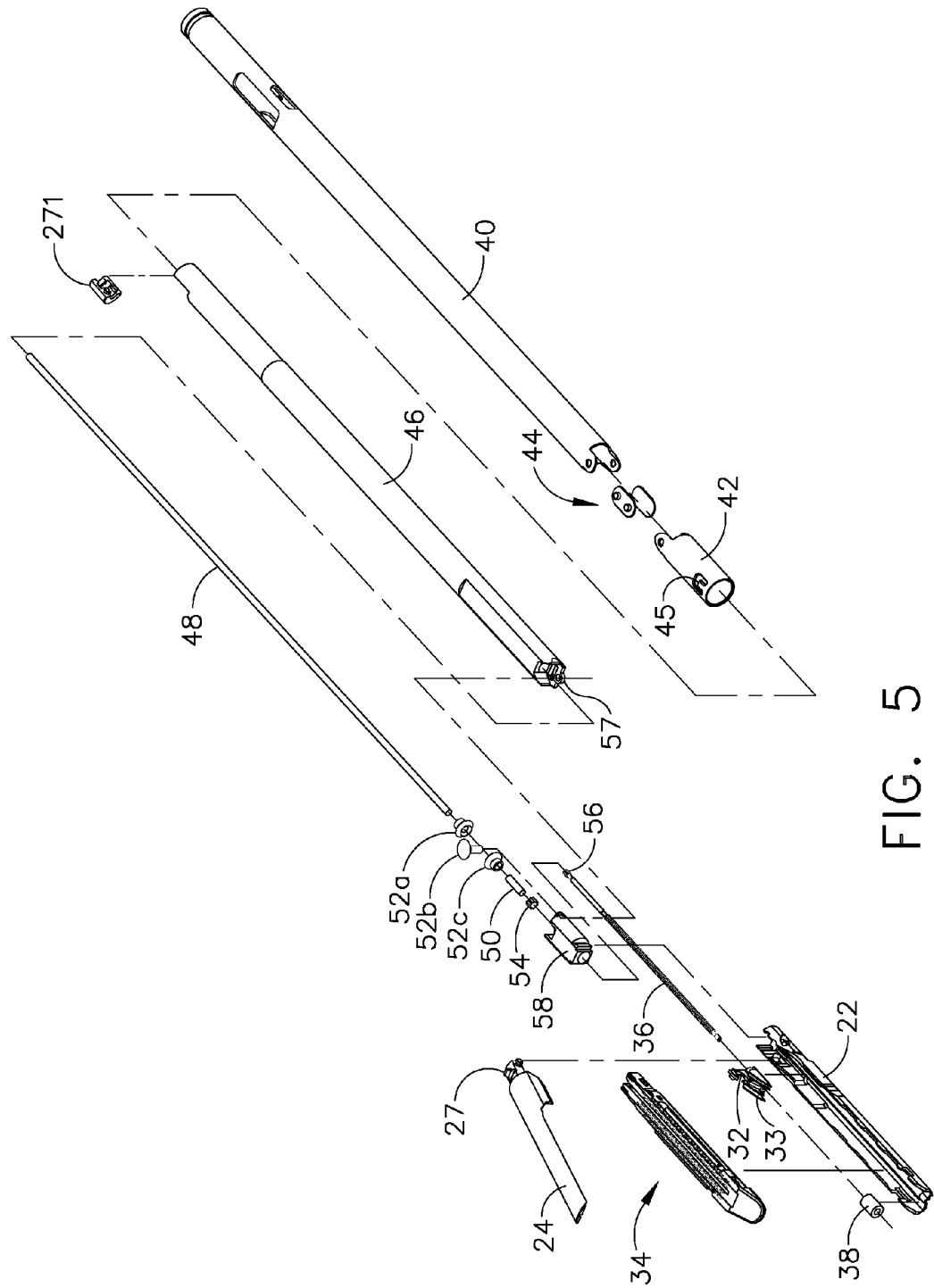
Figure 6:
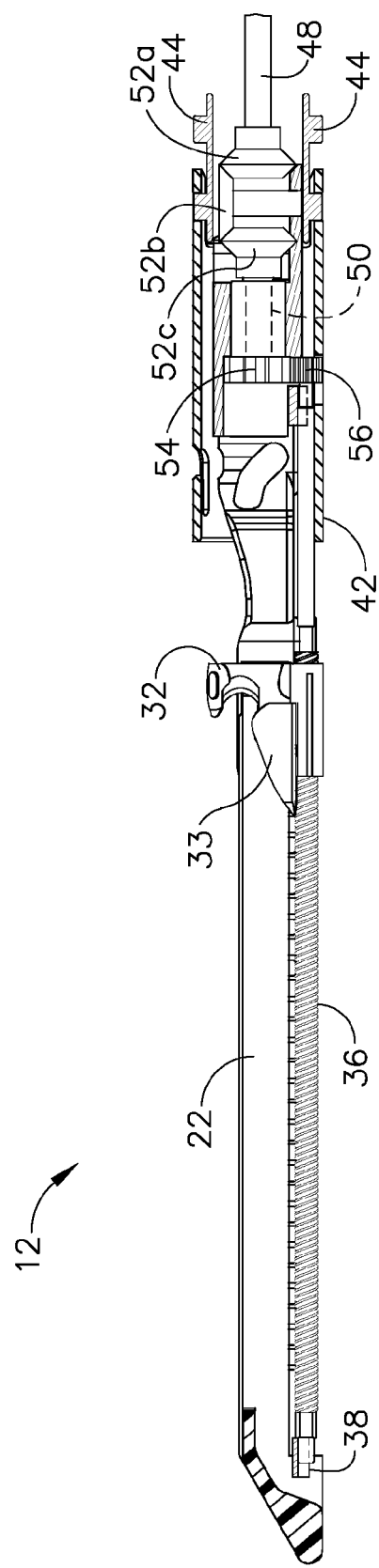
FIG. 6 is a side view of the end effector according to various embodiments of the present invention.
Figure 7:
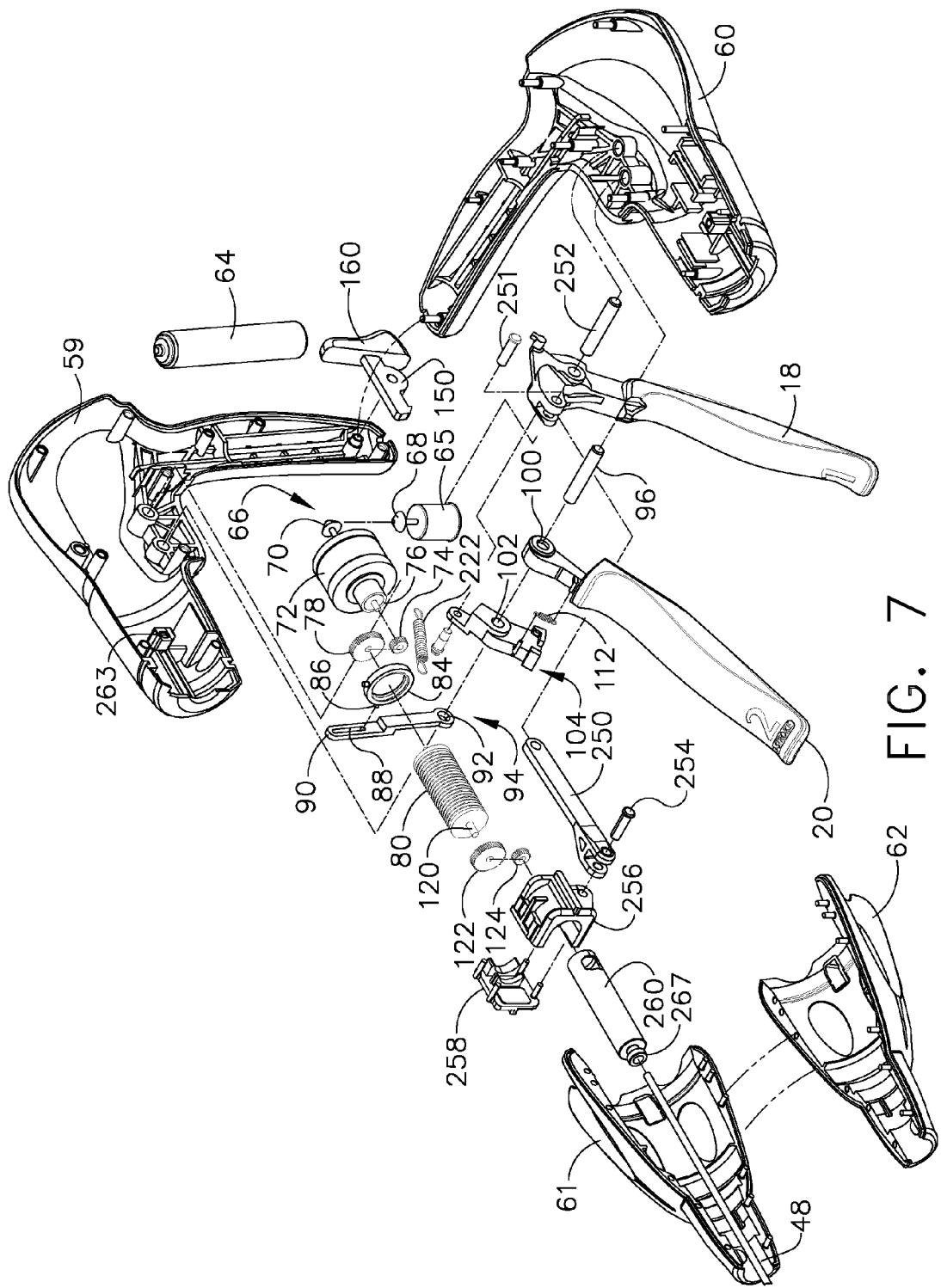
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector. The sled 33 may be made of, for example, plastic, and may have a sloped distal surface. As the sled 33 traverse the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

As described above, because of the lack of user feedback for the cutting/stapling operation, there is a general lack of acceptance among physicians of motor-driven endocutters where the cutting/stapling operation is actuated by merely pressing a button. In contrast, embodiments of the present invention provide a motor-driven endocutter with user-feedback of the deployment, force, and/or position of the cutting instrument in the end effector.

FIGS. 7-10 illustrate an exemplary embodiment of a motor-driven endocutter, and in particular the handle thereof, that provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, the motor 65 may be a DC brushed driving motor having a maximum rotation of, approximately, 5000 RPM. The motor 65 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 110, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
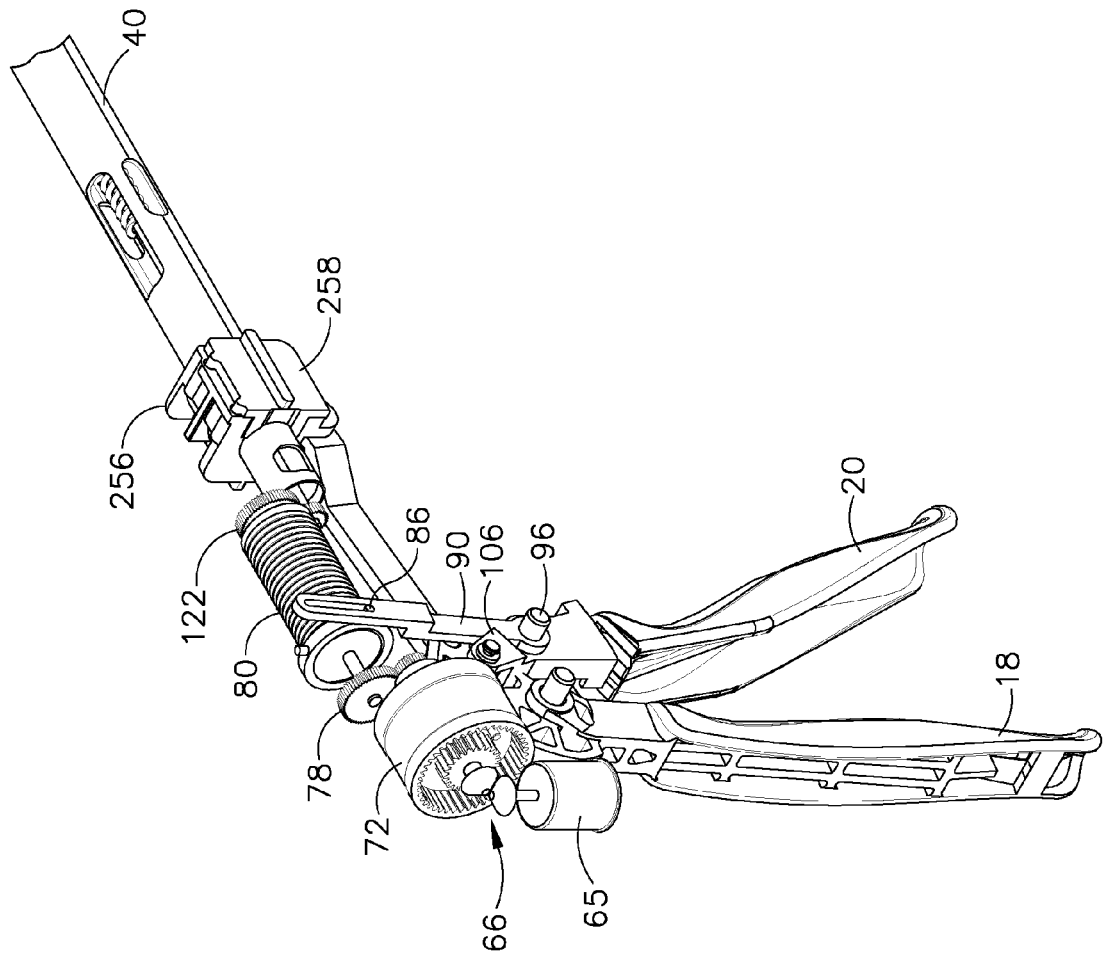
FIGS. 8 and 9 are partial perspective views of the handle according to various embodiments of the present invention.
Figure 9:
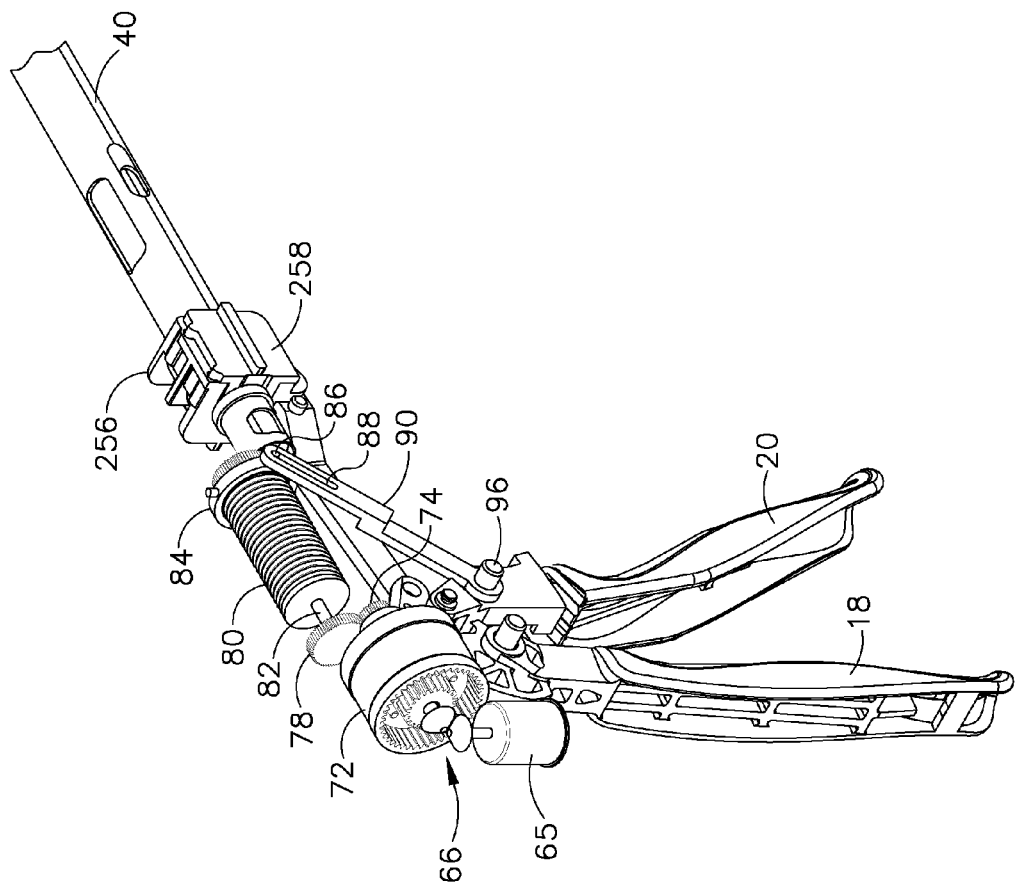
Figure 10:
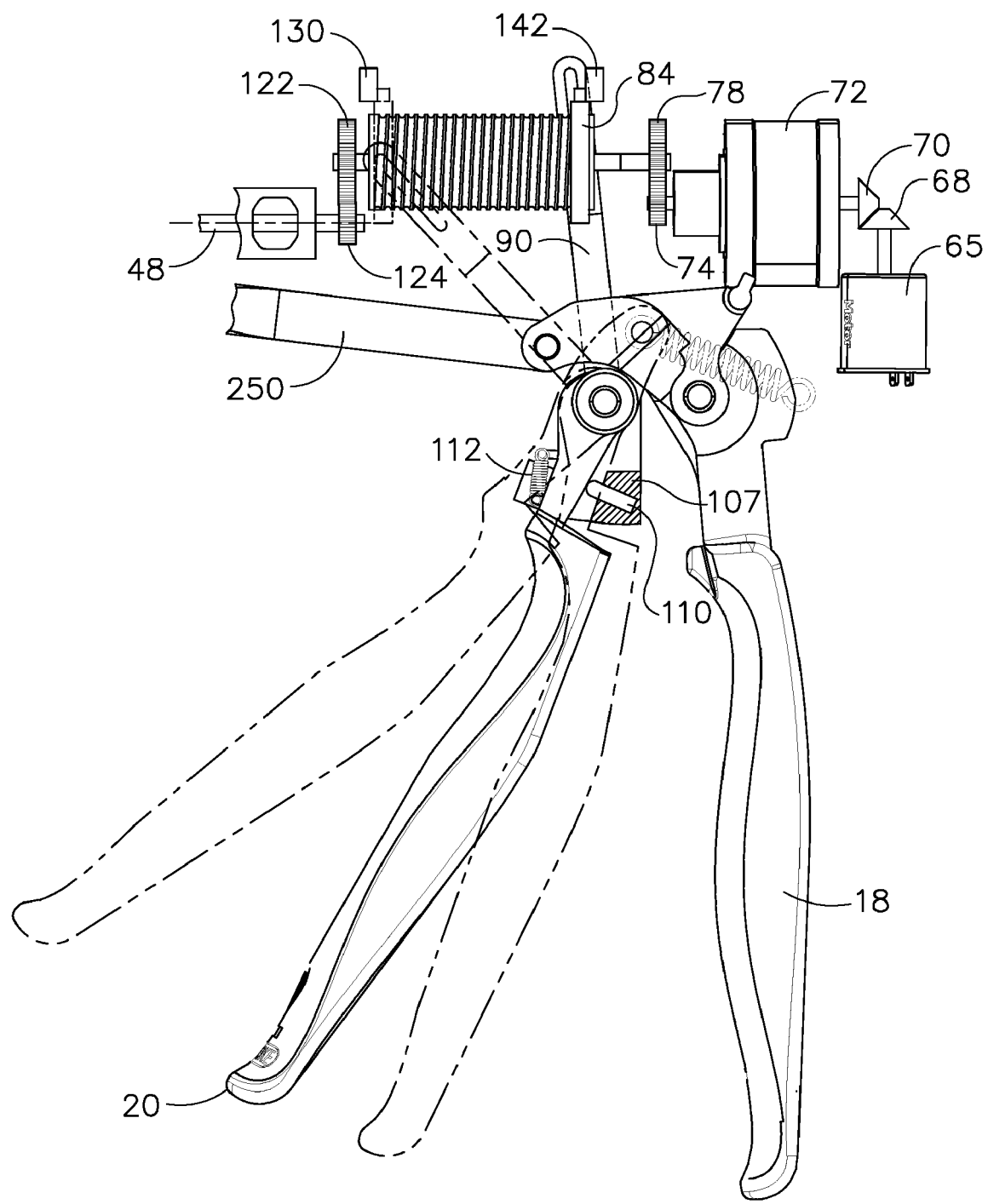
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

FIG. 41 and 42 illustrate two states of a variable sensor that may be used as the run motor sensor 110 according to various embodiments of the present invention. The sensor 110 may include a face portion 280, a first electrode (A) 282, a second electrode (B) 284, and a compressible dielectric material 286 (e.g., EAP) between the electrodes 282, 284. The sensor 110 may be positioned such that the face portion 280 contacts the firing trigger 20 when retracted. Accordingly, when the firing trigger 20 is retracted, the dielectric material 286 is compressed, as shown in FIG. 42, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric 286 is compressed due to retraction of the firing trigger 20 (denoted as force "F" in FIG. 42) is proportional to the impedance between the electrodes 282, 284, which can be used to proportionally control the motor 65.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
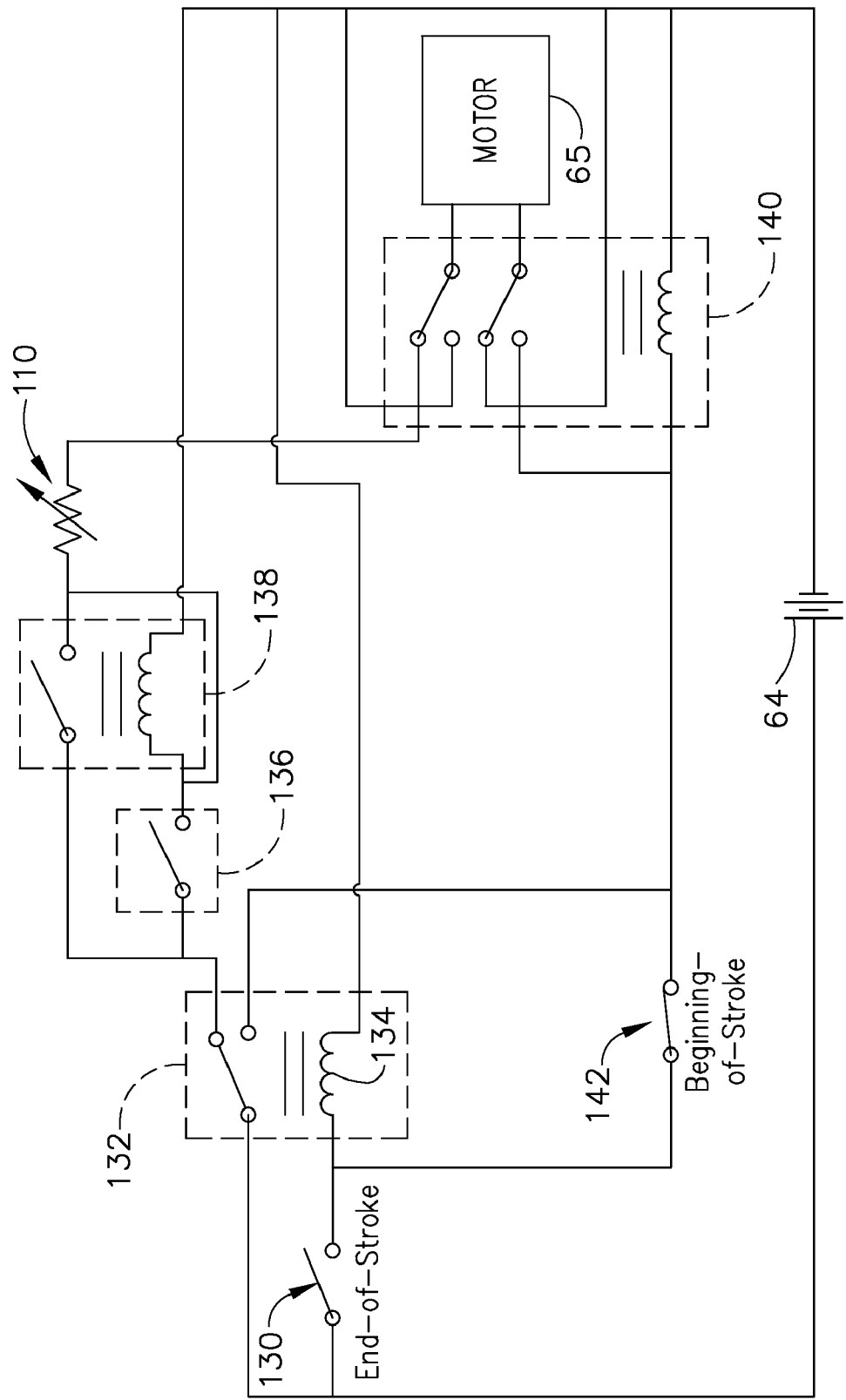
FIG. 11 is a schematic diagram of a circuit used in the instrument according to various embodiments of the present invention.

FIG. 11 is a schematic diagram of an electrical circuit of the instrument 10 according to various embodiments of the present invention. When an operator initially pulls in the firing trigger 20 after locking the closure trigger 18, the sensor 110 is activated, allowing current to flow there through. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 132. This causes the relay 132 to assume its energized state (not shown in FIG. 13), which causes current to bypass the cartridge lockout sensor 136 and variable resistor 110, and instead causes current to flow to both the normally-closed double pole, double throw relay 142 and back to the motor 65, but in a manner, via the relay 140, that causes the motor 65 to reverse its rotational direction.

Because the stop motor sensor switch 142 is normally-closed, current will flow back to the relay 132 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 12:
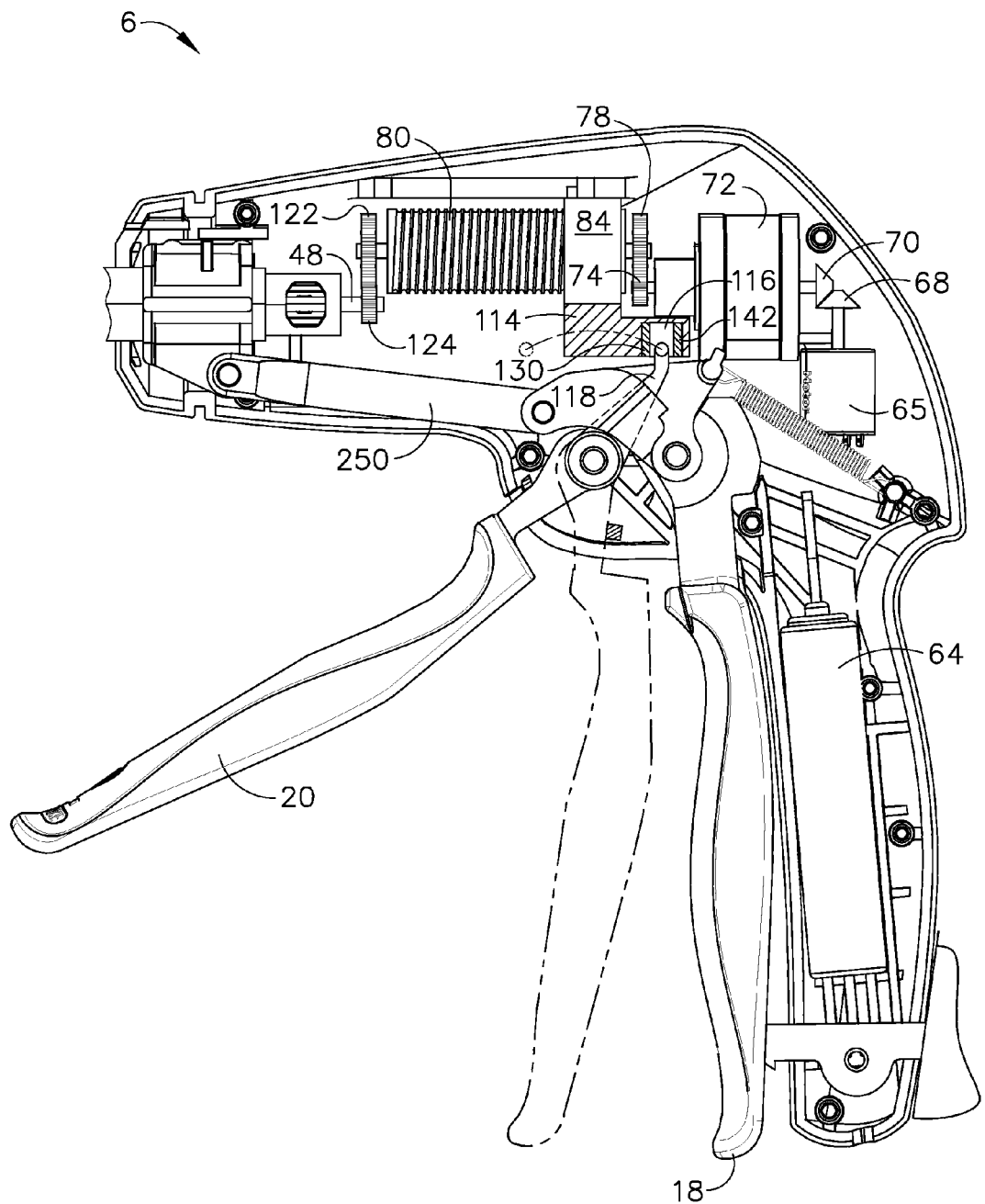
FIGS. 12-13 are side views of the handle according to other embodiments of the present invention.

FIG. 12 is a side-view of the handle 6 of a power-assist motorized endocutter according to another embodiment. The embodiment of FIG. 12 is similar to that of FIGS. 7-10 except that in the embodiment of FIG. 12, there is not slotted arm connected to the ring 84 threaded on the helical gear drum 80. Instead, in the embodiment of FIG. 12, the ring 84 includes a sensor portion 114 that moves with the ring 84 as the ring 84 advances down (and back) on the helical gear drum 80. The sensor portion 114 includes a notch 116. The reverse motor sensor 130 may be located at the distal end of the notch 116 and the stop motor sensor 142 may be located at the proximate end of the notch 116. As the ring 84 moves down the helical gear drum 80 (and back), the sensor portion 114 moves with it. Further, as shown in FIG. 12, the middle piece 104 may have an arm 118 that extends into the notch 12.

In operation, as an operator of the instrument 10 retracts in the firing trigger 20 toward the pistol grip 26, the run motor sensor 110 detects the motion and sends a signal to power the motor 65, which causes, among other things, the helical gear drum 80 to rotate. As the helical gear drum 80 rotates, the ring 84 threaded on the helical gear drum 80 advances (or retracts, depending on the rotation). Also, due to the pulling in of the firing trigger 20, the middle piece 104 is caused to rotate CCW with the firing trigger 20 due to the forward motion stop 107 that engages the firing trigger 20. The CCW rotation of the middle piece 104 cause the arm 118 to rotate CCW with the sensor portion 114 of the ring 84 such that the arm 118 stays disposed in the notch 116. When the ring 84 reaches the distal end of the helical gear drum 80, the arm 118 will contact and thereby trip the reverse motor sensor 130. Similarly, when the ring 84 reaches the proximate end of the helical gear drum 80, the arm will contact and thereby trip the stop motor sensor 142. Such actions may reverse and stop the motor 65, respectively, as described above.

Figure 13:
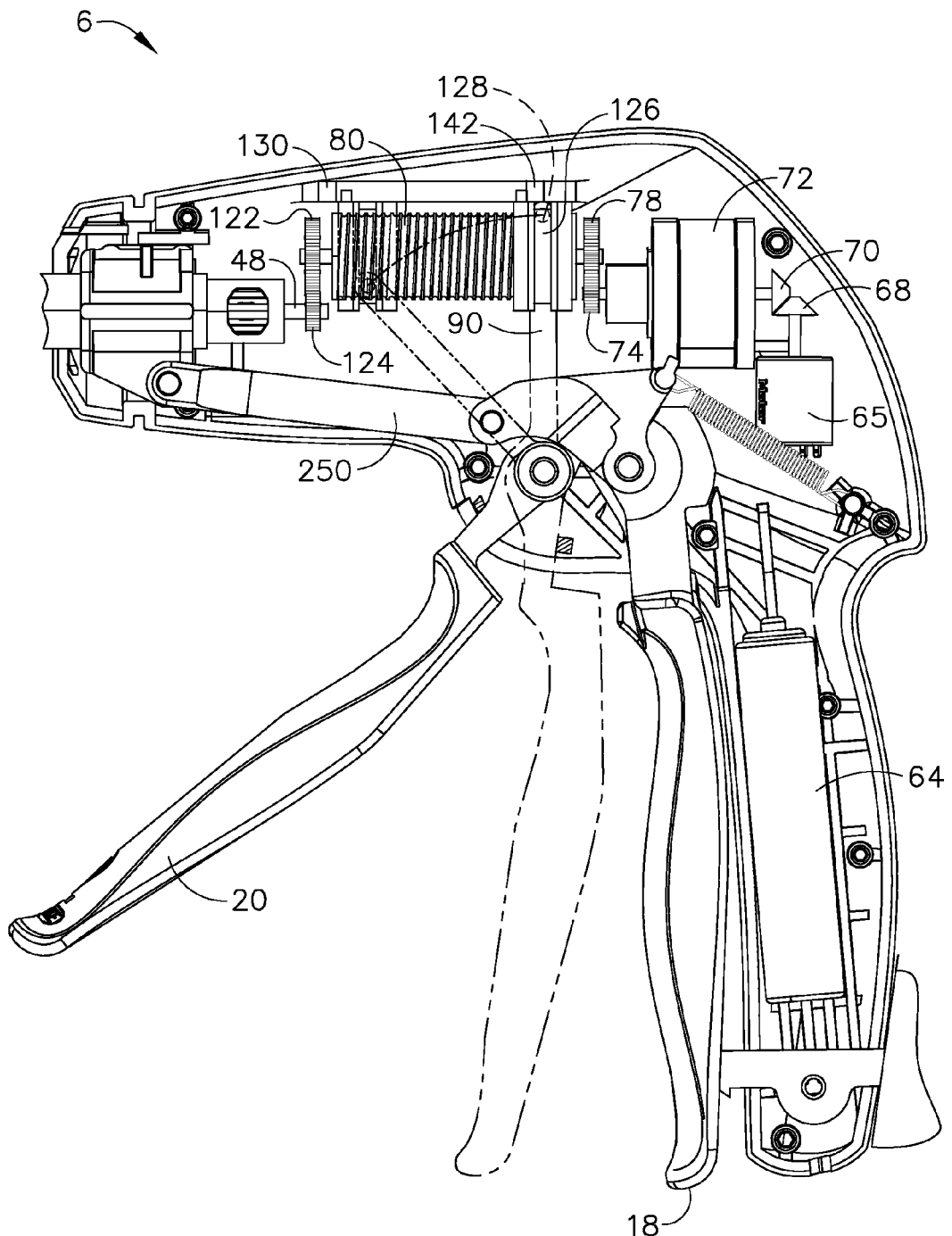

FIG. 13 is a side-view of the handle 6 of a power-assist motorized endocutter according to another embodiment. The embodiment of FIG. 13 is similar to that of FIGS. 7-10 except that in the embodiment of FIG. 13, there is no slot in the arm 90. Instead, the ring 84 threaded on the helical gear drum 80 includes a vertical channel 126. Instead of a slot, the arm 90 includes a post 128 that is disposed in the channel 126. As the helical gear drum 80 rotates, the ring 84 threaded on the helical gear drum 80 advances (or retracts, depending on the rotation). The arm 90 rotates CCW as the ring 84 advances due to the post 128 being disposed in the channel 126, as shown in FIG. 13.

Figure 14:
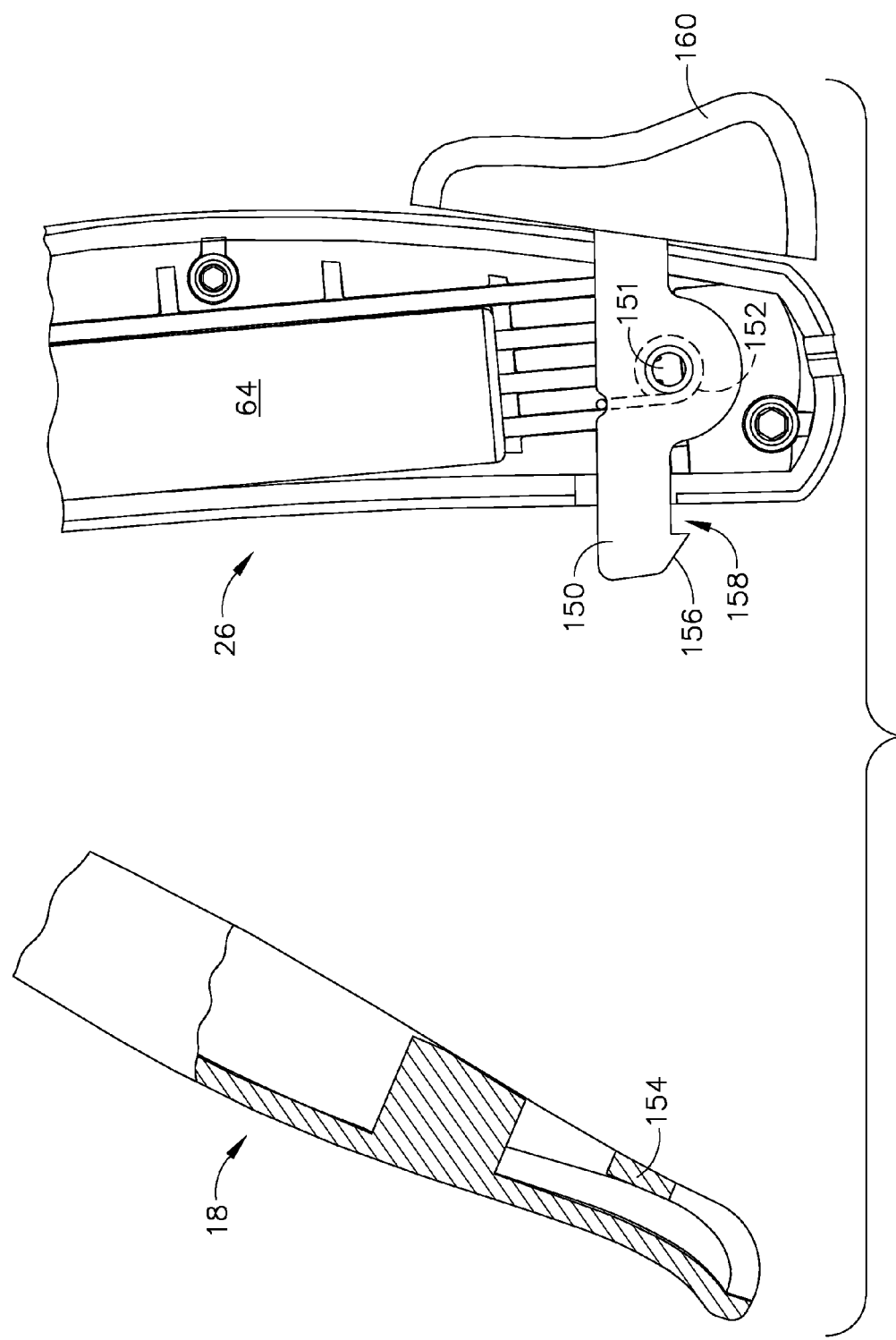
FIGS. 14-22 illustrate different mechanisms for locking the closure trigger according to various embodiments of the present invention.
Figure 15:
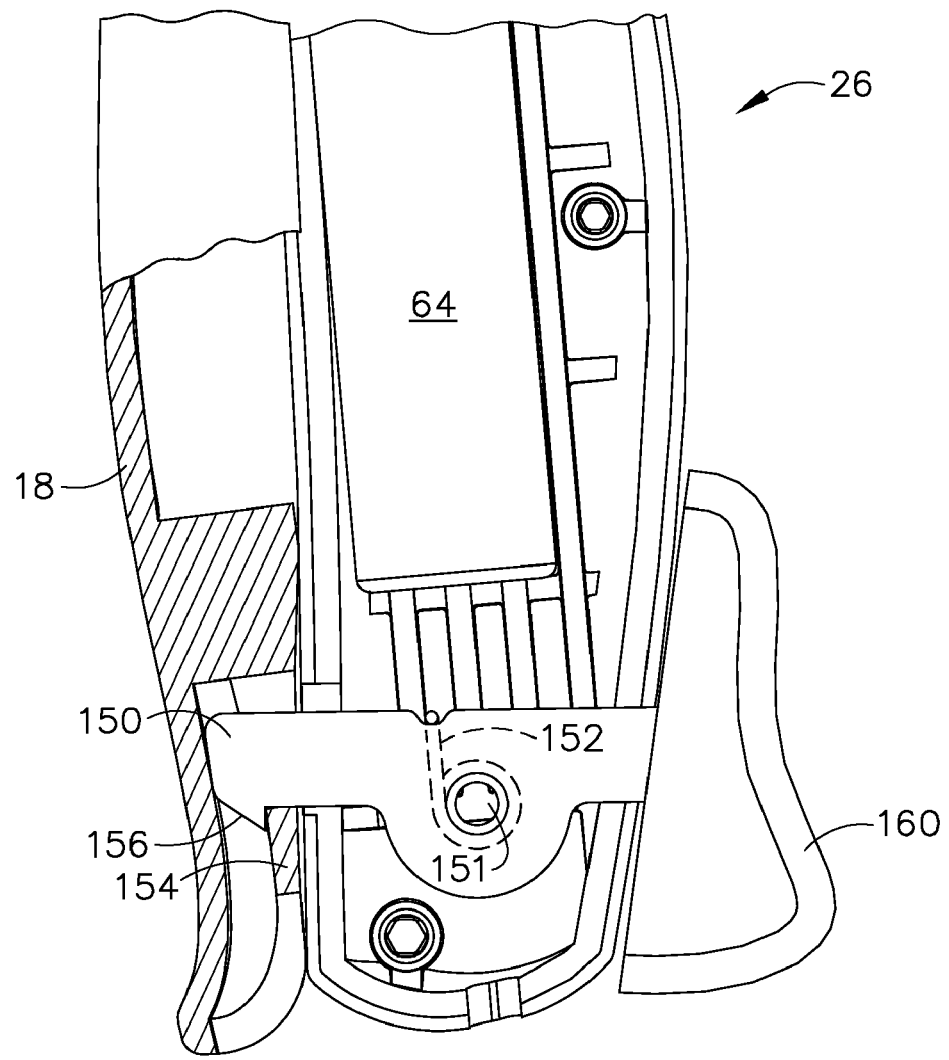

As mentioned above, in using a two-stroke motorized instrument, the operator first pulls back and locks the closure trigger 18. FIGS. 14 and 15 show one embodiment of a way to lock the closure trigger 18 to the pistol grip portion 26 of the handle 6. In the illustrated embodiment, the pistol grip portion 26 includes a hook 150 that is biased to rotate CCW about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or CW in FIGS. 12-13) until the closure bar 154 completely passes the sloped portion 156 passes into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 CW such that the closure bar 154 is released from the recessed notch 158.

Figure 16:
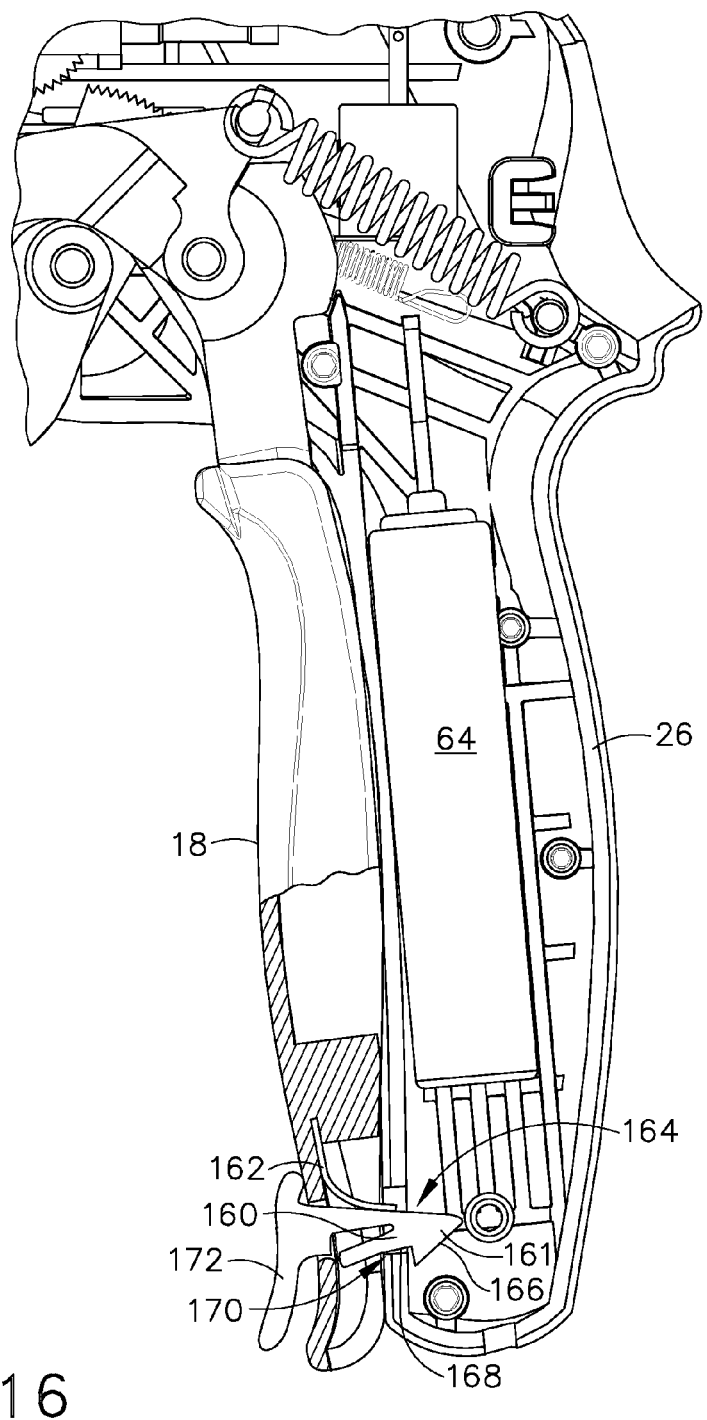

FIG. 16 shows another closure trigger locking mechanism according to various embodiments. In the embodiment of FIG. 16, the closure trigger 18 includes a wedge 160 having an arrow-head portion 161. The arrow-head portion 161 is biased downward (or CW) by a leaf spring 162. The wedge 160 and leaf spring 162 may be made from, for example, molded plastic. When the closure trigger 18 is retracted, the arrow-head portion 161 is inserted through an opening 164 in the pistol grip portion 26 of the handle 6. A lower chamfered surface 166 of the arrow-head portion 161 engages a lower sidewall 168 of the opening 164, forcing the arrow-head portion 161 to rotate CCW. Eventually the lower chamfered surface 166 fully passes the lower sidewall 168, removing the CCW force on the arrow-head portion 161, causing the lower sidewall 168 to slip into a locked position in a notch 170 behind the arrow-head portion 161.

To unlock the closure trigger 18, a user presses down on a button 172 on the opposite side of the closure trigger 18, causing the arrow-head portion 161 to rotate CCW and allowing the arrow-head portion 161 to slide out of the opening 164.

Figure 17:
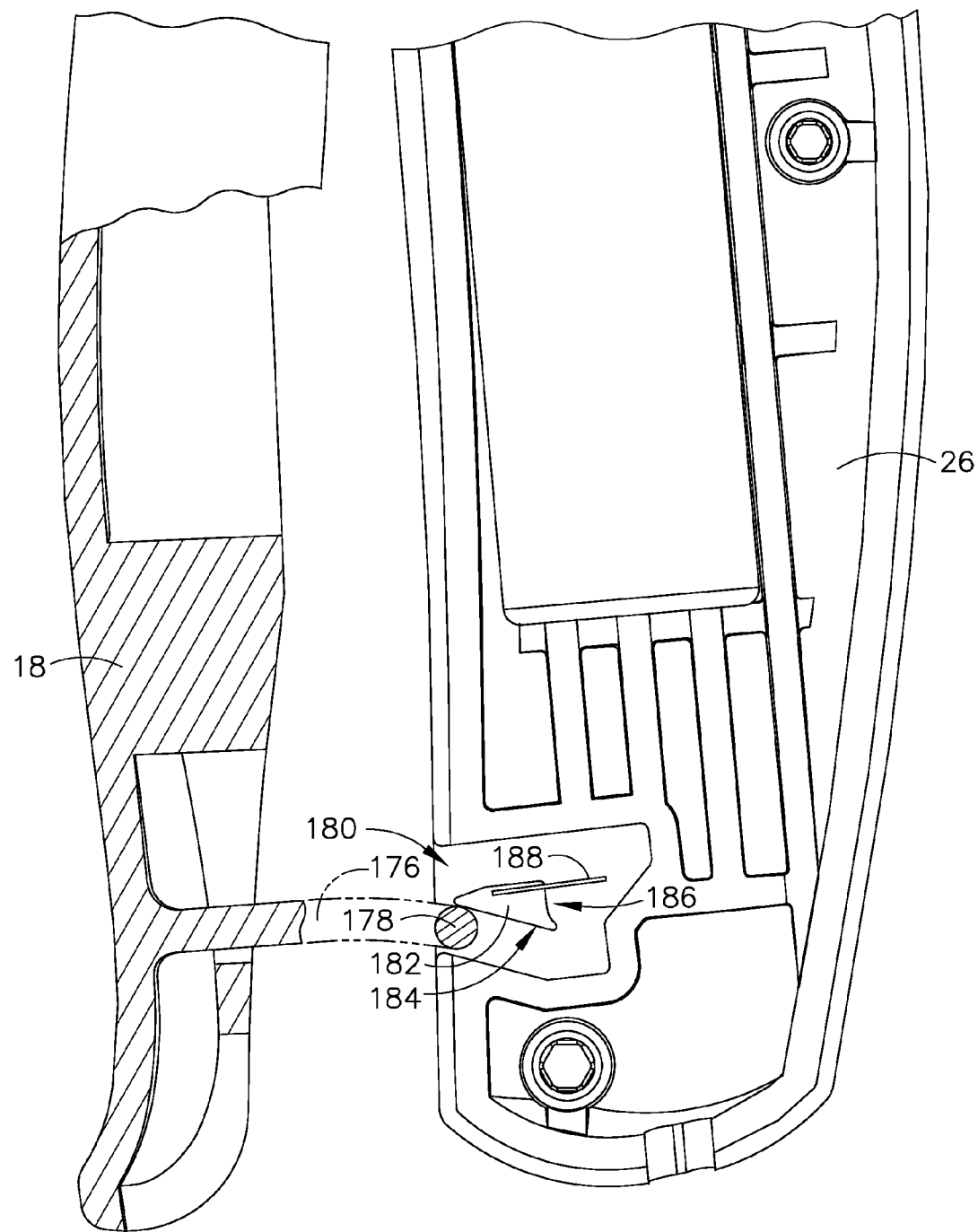
Figure 18:
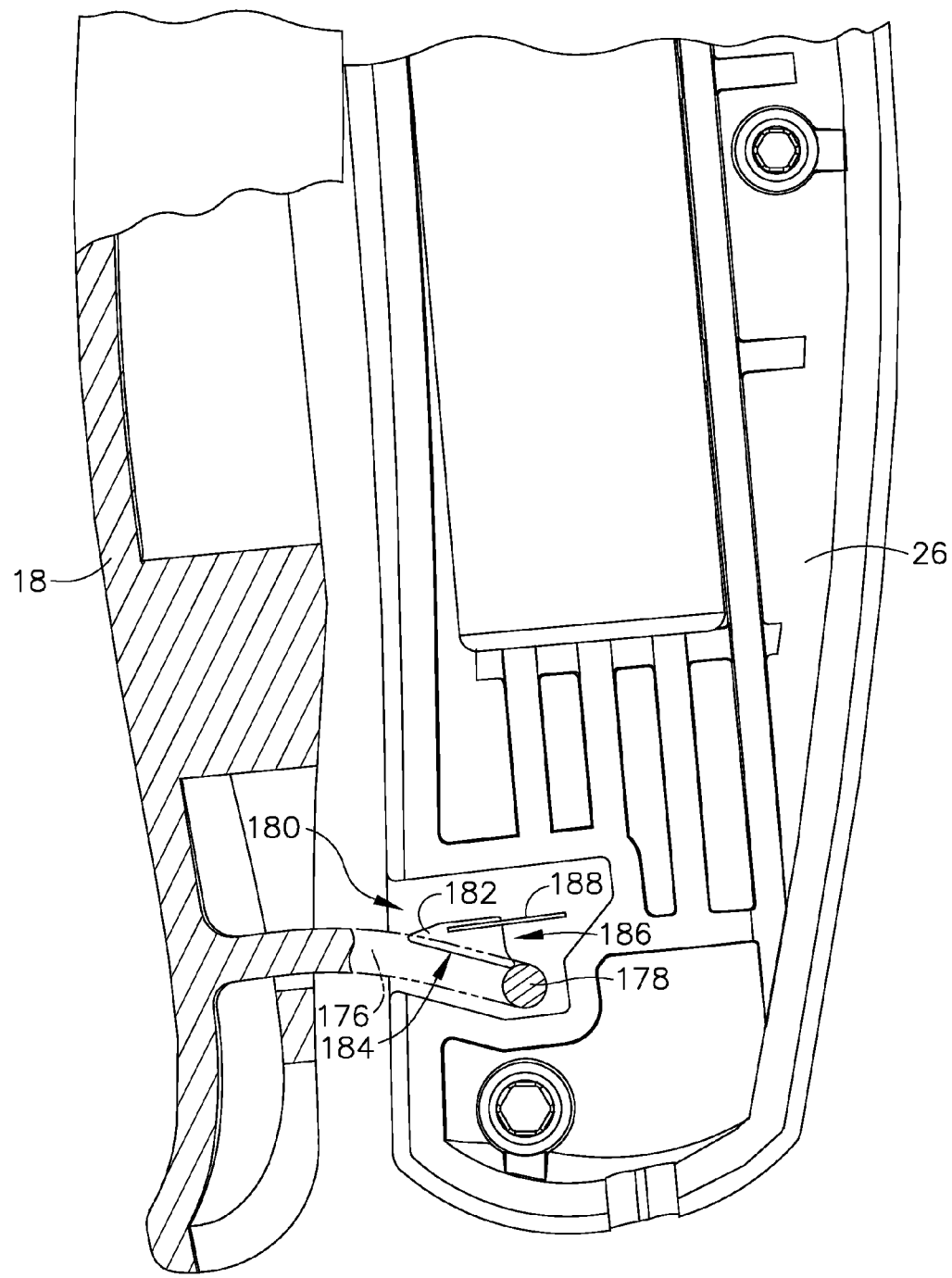
Figure 19:
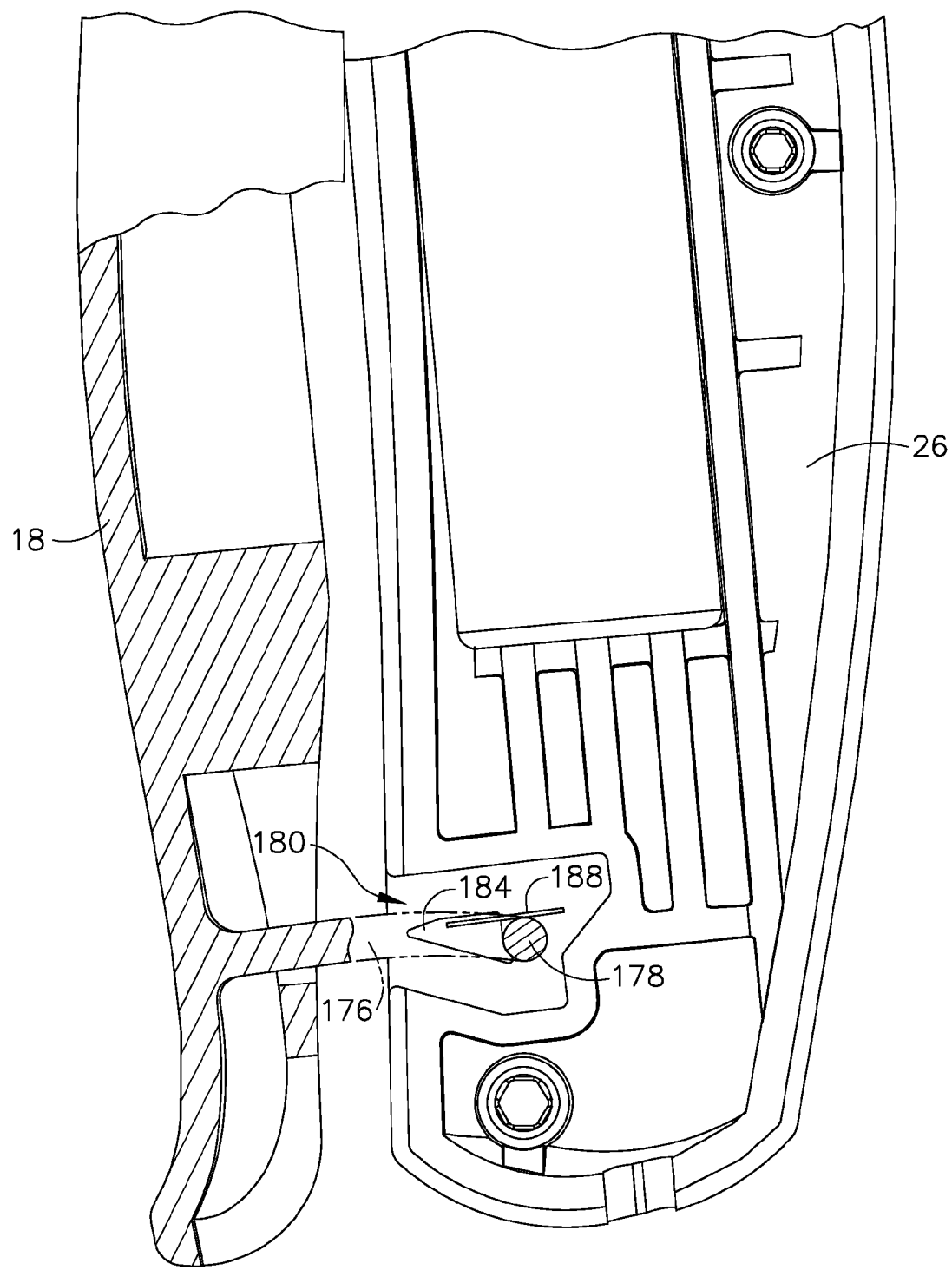

FIGS. 17-22 show a closure trigger locking mechanism according to another embodiment. As shown in this embodiment, the closure trigger 18 includes a flexible longitudinal arm 176 that includes a lateral pin 178 extending therefrom. The arm 176 and pin 178 may be made from molded plastic, for example. The pistol grip portion 26 of the handle 6 includes an opening 180 with a laterally extending wedge 182 disposed therein. When the closure trigger 18 is retracted, the pin 178 engages the wedge 182, and the pin 178 is forced downward (i.e., the arm 176 is rotated CW) by the lower surface 184 of the wedge 182, as shown in FIGS. 17 and 18. When the pin 178 fully passes the lower surface 184, the CW force on the arm 176 is removed, and the pin 178 is rotated CCW such that the pin 178 comes to rest in a notch 186 behind the wedge 182, as shown in FIG. 19, thereby locking the closure trigger 18. The pin 178 is further held in place in the locked position by a flexible stop 188 extending from the wedge 184.

Figure 20:
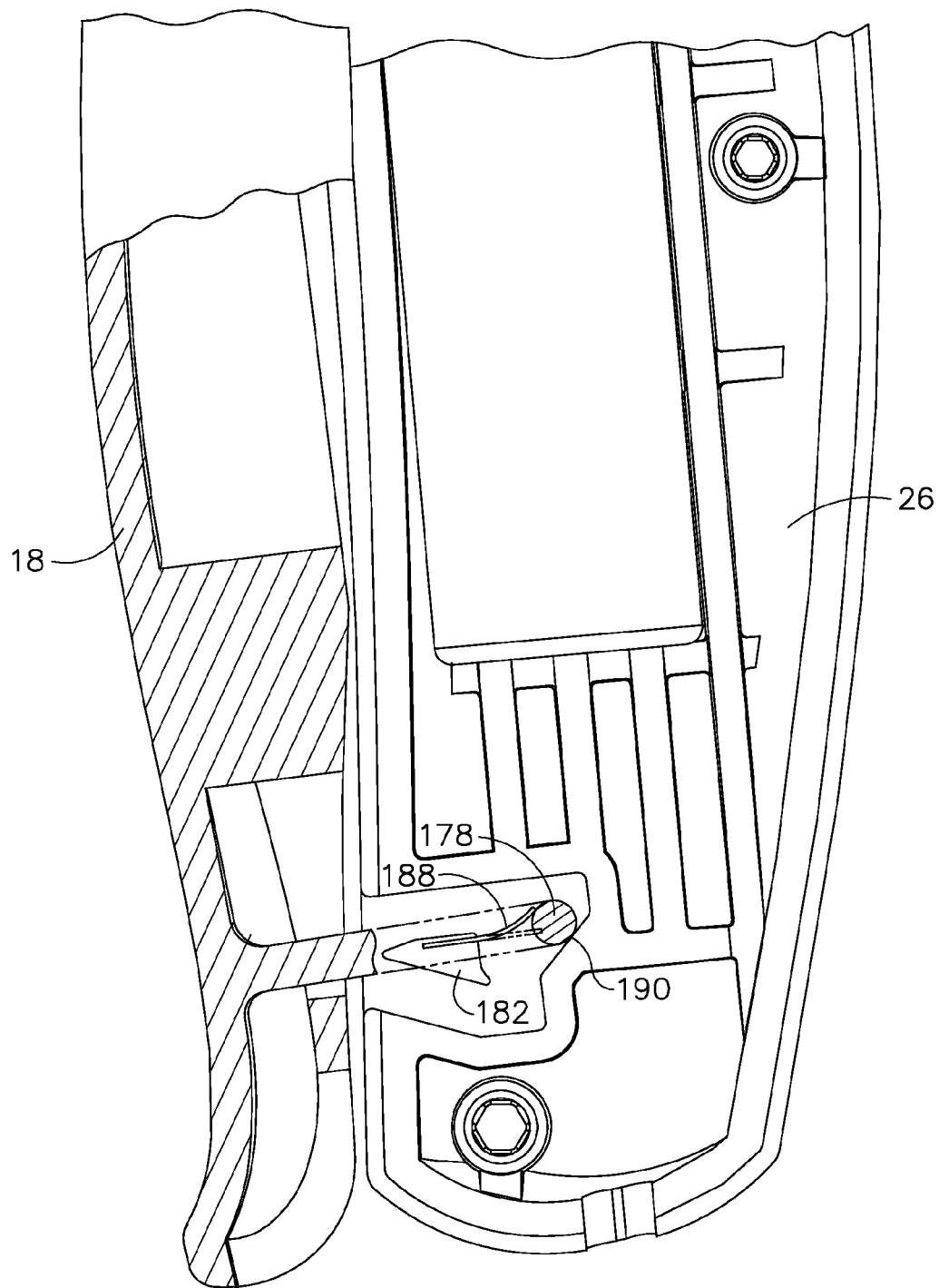
Figure 21:
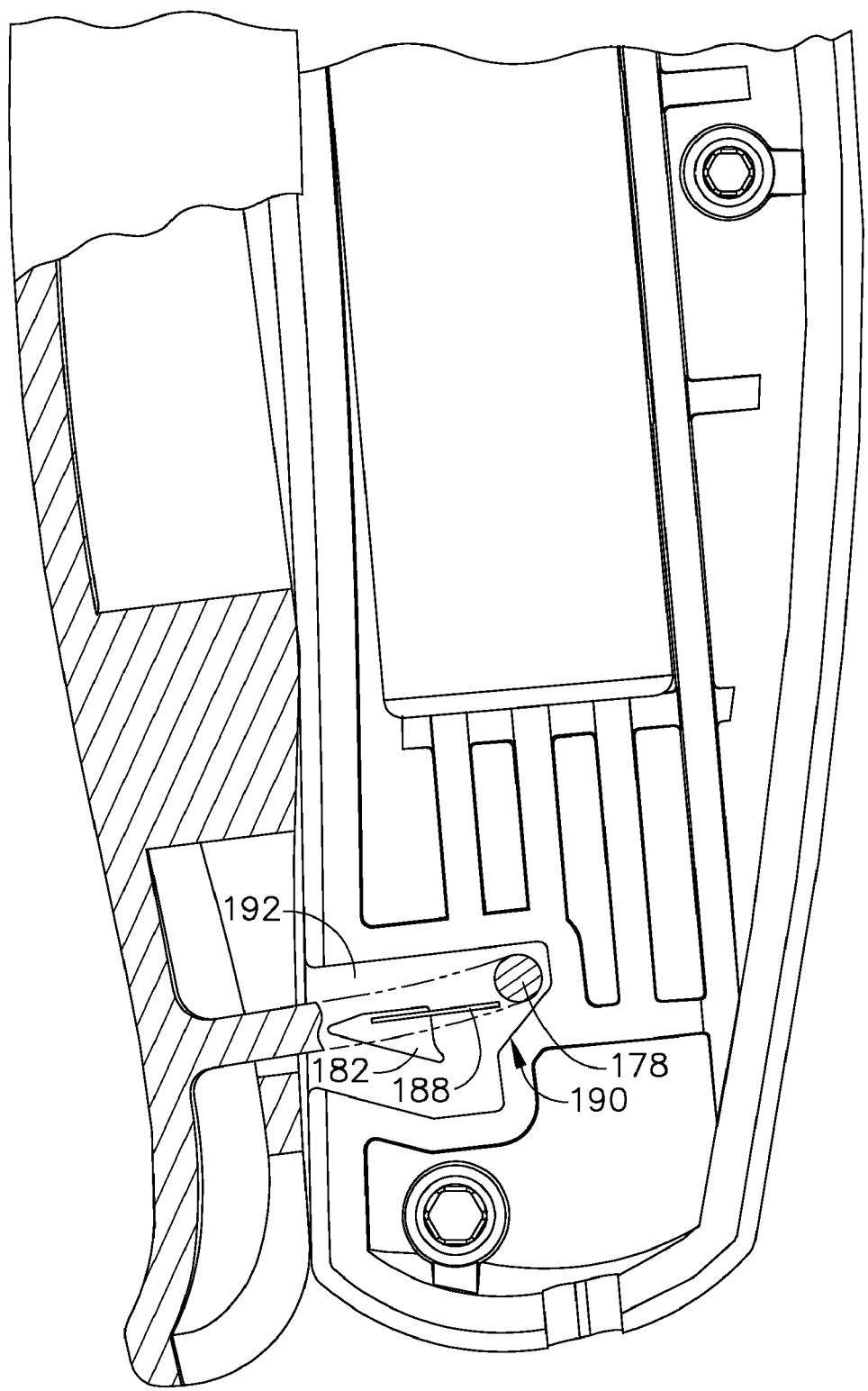
Figure 22:
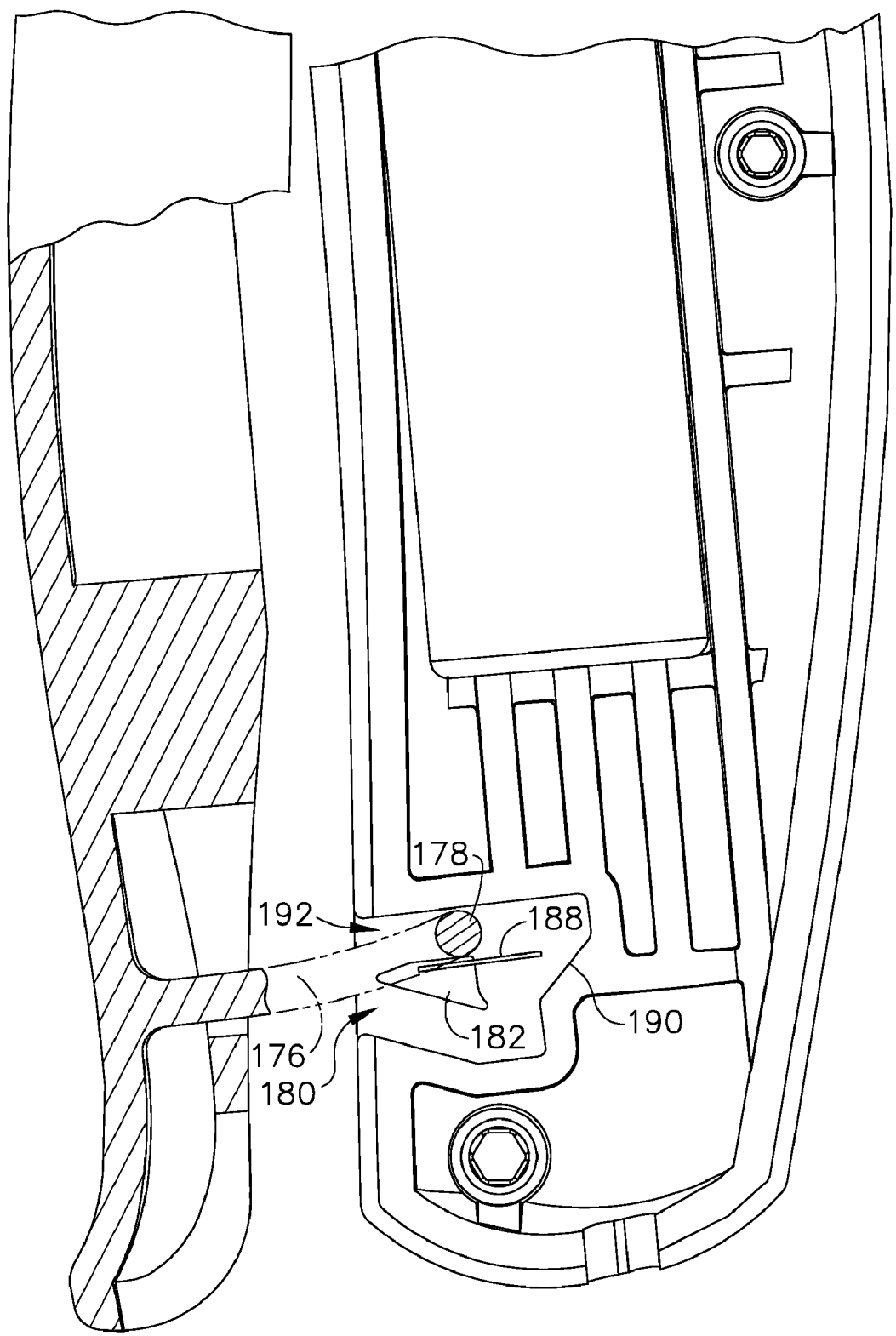

To unlock the closure trigger 18, the operator may further squeeze the closure trigger 18, causing the pin 178 to engage a sloped backwall 190 of the opening 180, forcing the pin 178 upward past the flexible stop 188, as shown in FIGS. 20 and 21. The pin 178 is then free to travel out an upper channel 192 in the opening 180 such that the closure trigger 18 is no longer locked to the pistol grip portion 26, as shown in FIG. 22.

FIGS. 23A-B show a universal joint ("u-joint") 195. The second piece 195-2 of the u-joint 195 rotates in a horizontal plane in which the first piece 195-1 lies. FIG. 23A shows the u-joint 195 in a linear (180°) orientation and FIG. 23B shows the u-joint 195 at approximately a 150° orientation. The u-joint 195 may be used instead of the bevel gears 52a-c (see FIG. 4, for example) at the articulation point 14 of the main drive shaft assembly to articulate the end effector 12. FIGS. 24A-B show a torsion cable 197 that may be used in lieu of both the bevel gears 52a-c and the u-joint 195 to realize articulation of the end effector 12.

FIGS. 25-31 illustrate another embodiment of a motorized, two-stroke surgical cutting and fastening instrument 10 with power assist according to another embodiment of the present invention. The embodiment of FIGS. 25-31 is similar to that of FIGS. 6-10 except that instead of the helical gear drum 80, the embodiment of FIGS. 23-28 includes an alternative gear drive assembly. The embodiment of FIGS. 25-31 includes a gear box assembly 200 including a number of gears disposed in a frame 201, wherein the gears are connected between the planetary gear 72 and the pinion gear 124 at the proximate end of the drive shaft 48. As explained further below, the gear box assembly 200 provides feedback to the user via the firing trigger 20 regarding the deployment and loading force of the end effector 12. Also, the user may provide power to the system via the gear box assembly 200 to assist the deployment of the end effector 12. In that sense, like the embodiments described above, the embodiment of FIGS. 23-32 is another power assist, motorized instrument 10 that provides feedback to the user regarding the loading force experienced by the cutting instrument.

In the illustrated embodiment, the firing trigger 20 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 207 may be inserted through openings in the firing trigger pieces 202, 204 and may be the point about which the firing trigger 20 rotates. In addition, a spring 222 may bias the firing trigger 20 to rotate in a COW direction. The spring 222 may have a distal end connected to a pin 224 that is connected to the pieces 202, 204 of the firing trigger 20. The proximate end of the spring 222 may be connected to one of the handle exterior lower side pieces 59, 60.

In the illustrated embodiment, both the main body portion 202 and the stiffening portion 204 includes gear portions 206, 208 (respectively) at their upper end portions. The gear portions 206, 208 engage a gear in the gear box assembly 200, as explained below, to drive the main drive shaft assembly and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 20. In addition, the first gear 210 engages a smaller second gear 212, the smaller second gear 212 being coaxial with a large third gear 214. The third gear 214 engages a smaller fourth gear 216, the smaller fourth gear being coaxial with a fifth gear 218. The fifth gear 218 is a 90° bevel gear that engages a mating 90° bevel gear 220 (best shown in FIG. 31) that is connected to the pinion gear 124 that drives the main drive shaft 48.

In operation, when the user retracts the firing trigger 20, a run motor sensor (not shown) is activated, which may provide a signal to the motor 65 to rotate at a rate proportional to the extent or force with which the operator is retracting the firing trigger 20. This causes the motor 65 to rotate at a speed proportional to the signal from the sensor. The sensor is not shown for this embodiment, but it could be similar to the run motor sensor 110 described above. The sensor could be located in the handle 6 such that it is depressed when the firing trigger 20 is retracted. Also, instead of a proportional-type sensor, an on/off type sensor may be used.

Rotation of the motor 65 causes the bevel gears 68, 70 to rotate, which causes the planetary gear 72 to rotate, which causes, via the drive shaft 76, the ring gear 122 to rotate. The ring gear 122 meshes with the pinion gear 124, which is connected to the main drive shaft 48. Thus, rotation of the pinion gear 124 drives the main drive shaft 48, which causes actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate CCW when the motor 65 provides forward drive for the end effector 12 (and to rotate CCW when the motor 65 rotates in reverse to retract the end effector 12). In that way, the user experiences feedback regarding loading force and deployment of the end effector 12 by way of the user's grip on the firing trigger 20. Thus, when the user retracts the firing trigger 20, the operator will experience a resistance related to the load force experienced by the end effector 12. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portions 206, 208 to rotate CCW, which causes the gears of the gear box assembly 200 to rotate, thereby causing the pinion gear 124 to rotate, which causes the main drive shaft 48 to rotate.

Although not shown in FIGS. 25-31, the instrument 10 may further include reverse motor and stop motor sensors. As described above, the reverse motor and stop motor sensors may detect, respectively, the end of the cutting stroke (full deployment of the knife/sled driving member 32) and the end of retraction operation (full retraction of the knife/sled driving member 32). A similar circuit to that described above in connection with FIG. 11 may be used to appropriately power the motor 65.

FIGS. 32-36 illustrate a two-stroke, motorized surgical cutting and fastening instrument 10 with power assist according to another embodiment. The embodiment of FIGS. 32-36 is similar to that of FIGS. 25-31 except that in the embodiment of FIGS. 32-36, the firing trigger 20 includes a lower portion 228 and an upper portion 230. Both portions 228, 230 are connected to and pivot about a pivot pin 207 that is disposed through each portion 228, 230. The upper portion 230 includes a gear portion 232 that engages the first gear 210 of the gear box assembly 200. The spring 222 is connected to the upper portion 230 such that the upper portion is biased to rotate in the CW direction. The upper portion 230 may also include a lower arm 234 that contacts an upper surface of the lower portion 228 of the firing trigger 20 such that when the upper portion 230 is caused to rotate CW the lower portion 228 also rotates CW, and when the lower portion 228 rotates CCW the upper portion 230 also rotates CCW. Similarly, the lower portion 228 includes a rotational stop 238 that engages a lower shoulder of the upper portion 230. In that way, when the upper portion 230 is caused to rotate CCW the lower portion 228 also rotates CCW, and when the lower portion 228 rotates CW the upper portion 230 also rotates CW.

The illustrated embodiment also includes the run motor sensor 110 that communicates a signal to the motor 65 that, in various embodiments, may cause the motor 65 to rotate at a speed proportional to the force applied by the operator when retracting the firing trigger 20. The sensor 110 may be, for example, a rheostat or some other variable resistance sensor, as explained herein. In addition, the instrument 10 may include a reverse motor sensor 130 that is tripped or switched when contacted by a front face 242 of the upper portion 230 of the firing trigger 20. When activated, the reverse motor sensor 130 sends a signal to the motor 65 to reverse direction. Also, the instrument 10 may include a stop motor sensor 142 that is tripped or actuated when contacted by the lower portion 228 of the firing trigger 20. When activated, the stop motor sensor 142 sends a signal to stop the reverse rotation of the motor 65.

Figure 32:
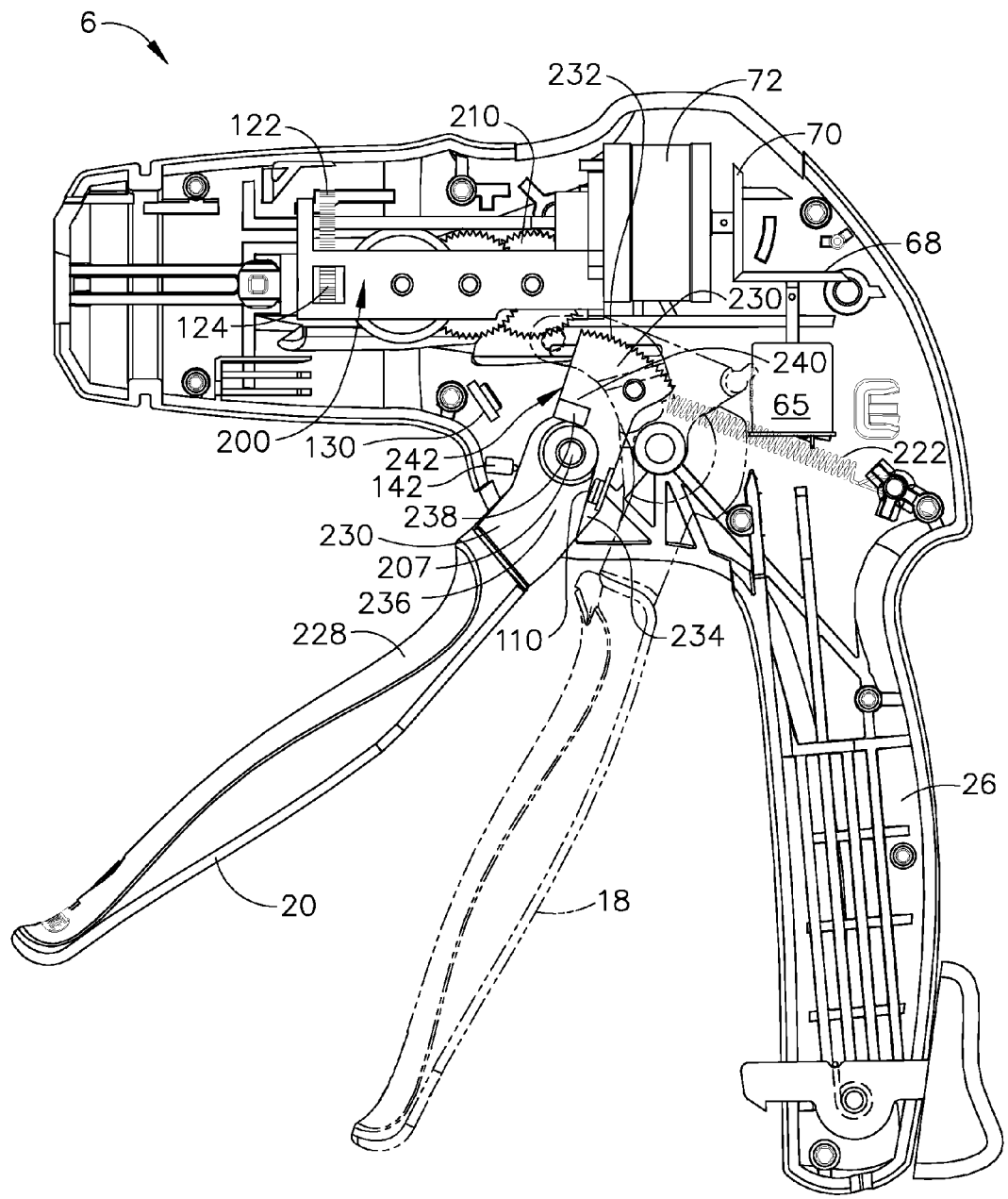
Figure 33:
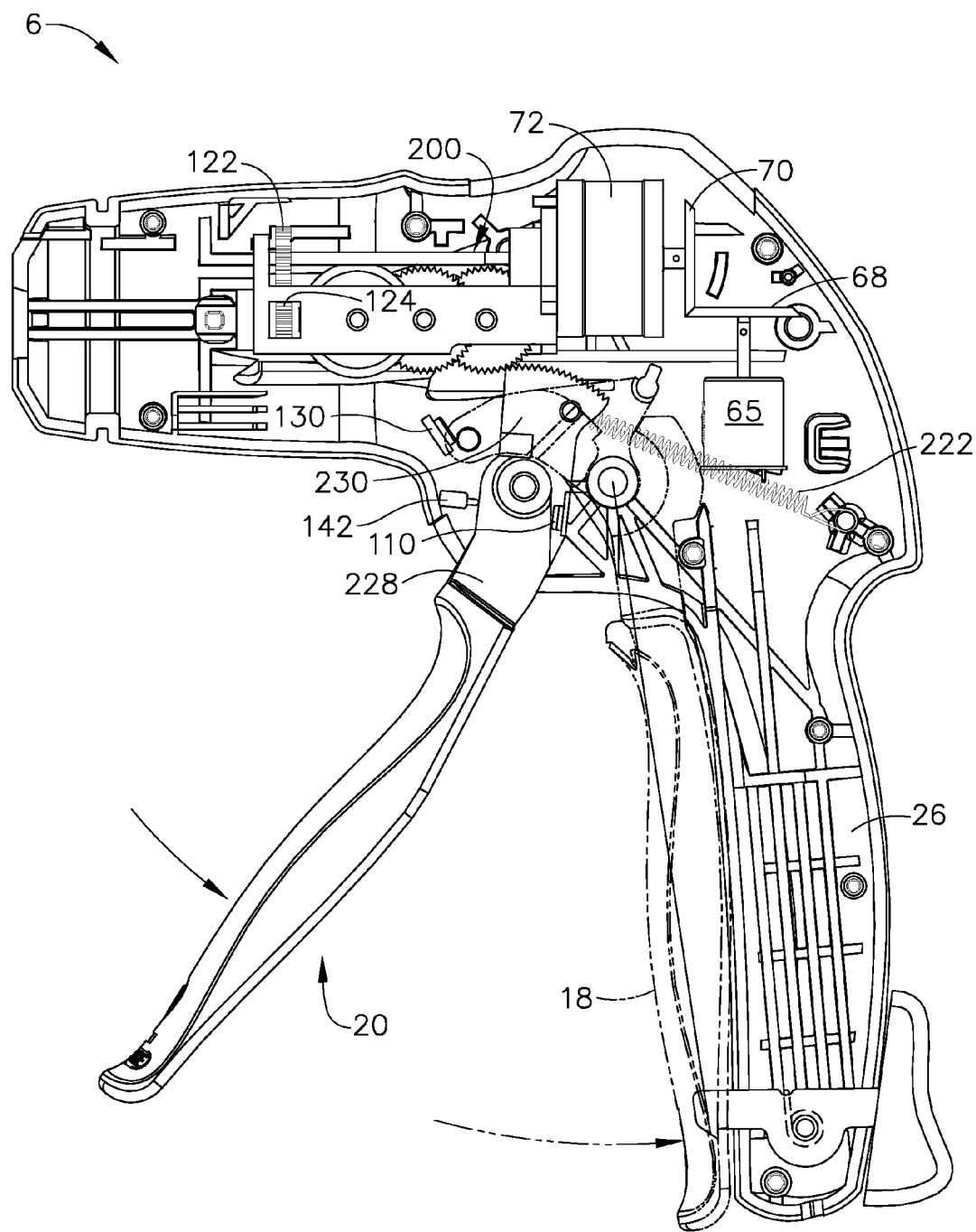
Figure 34:
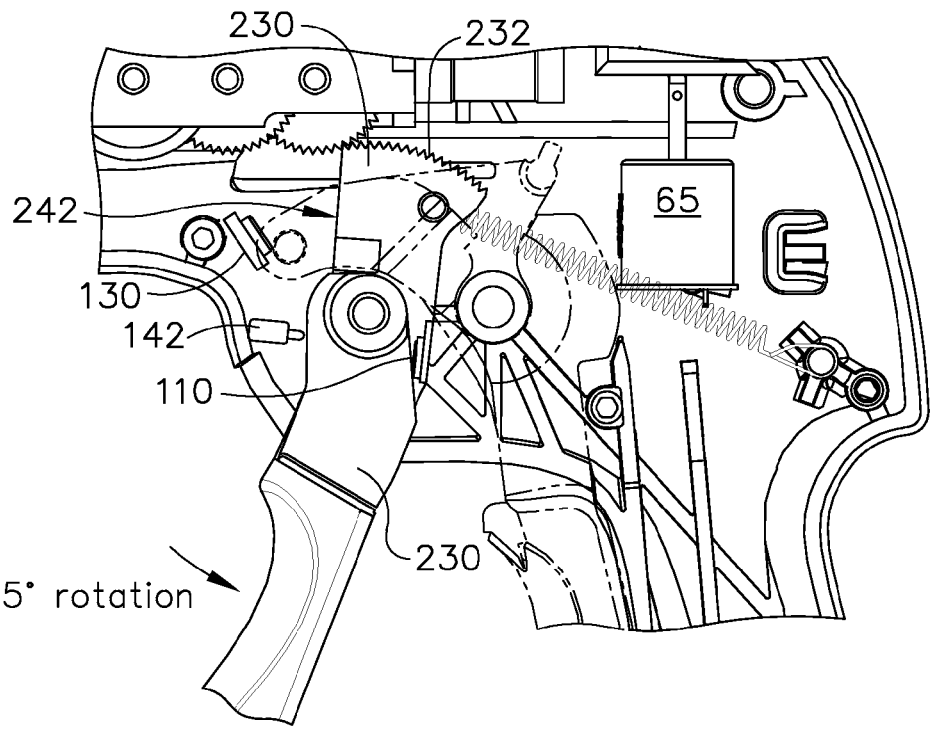
Figure 35:
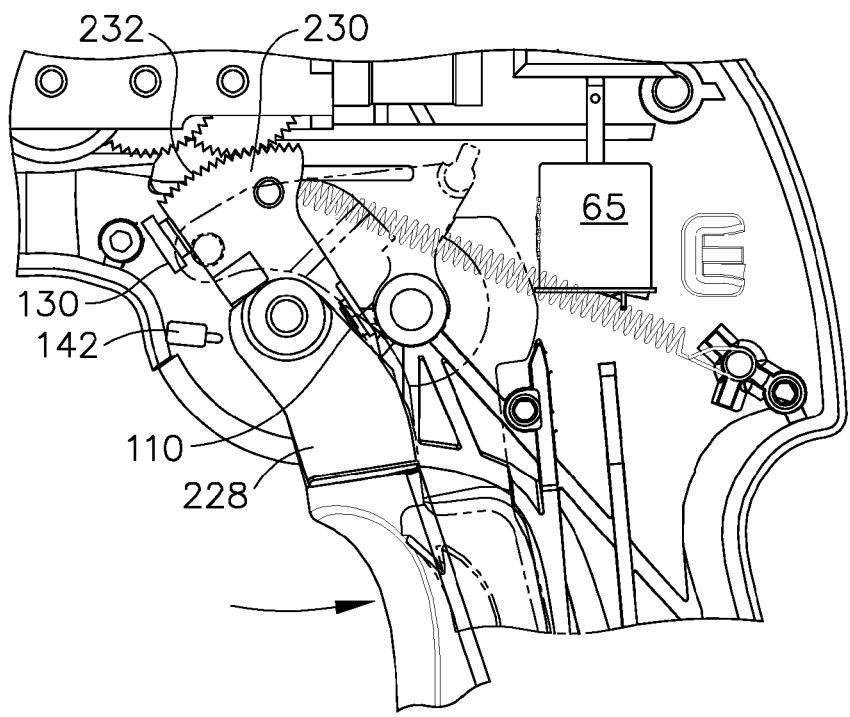
Figure 36:
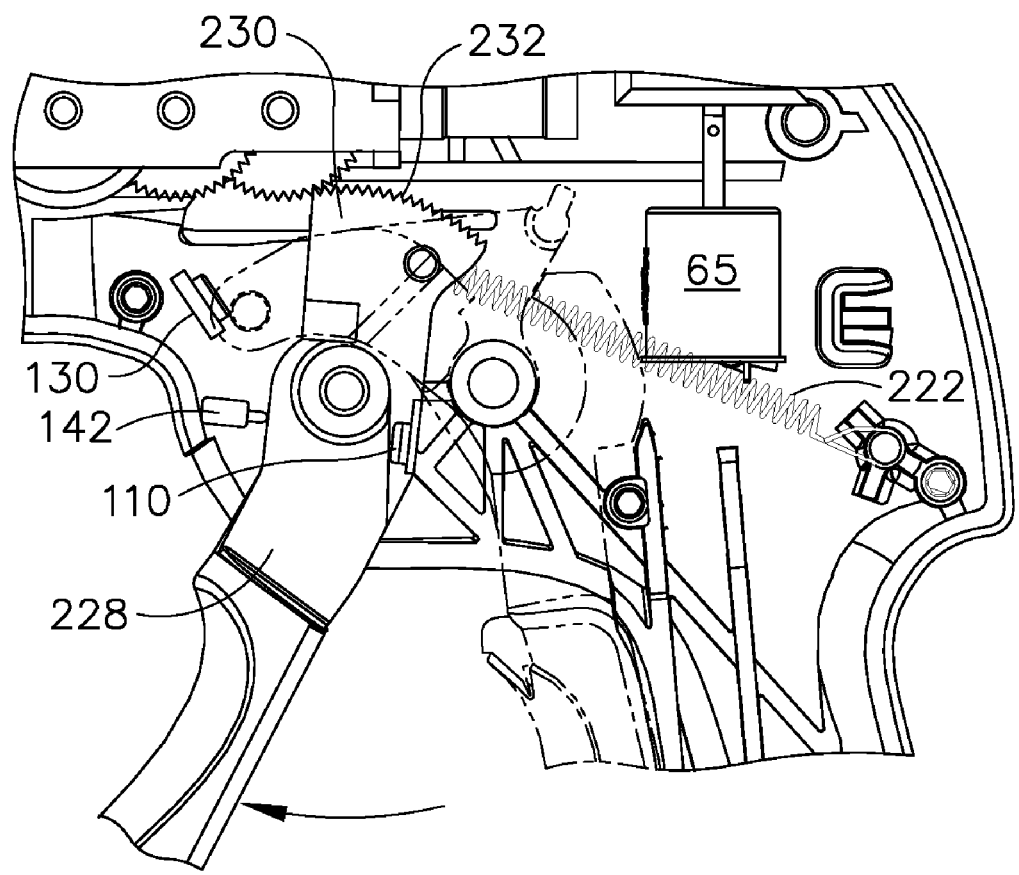

In operation, when an operator retracts the closure trigger 18 into the locked position, the firing trigger 20 is retracted slightly (through mechanisms known in the art, including U.S. Pat. No. 6,978,921 to Frederick Shelton, IV et. al and U.S. Pat. No. 6,905,057 to Jeffery S. Swayze et. al, which are incorporated herein by reference) so that the user can grasp the firing trigger 20 to initiate the cutting/stapling operation, as shown in FIGS. 32 and 33. At that point, as shown in FIG. 33, the gear portion 232 of the upper portion 230 of the firing trigger 20 moves into engagement with the first gear 210 of the gear box assembly 200. When the operator retracts the firing trigger 20, according to various embodiments, the firing trigger 20 may rotate a small amount, such as five degrees, before tripping the run motor sensor 110, as shown in FIG. 34. Activation of the sensor 110 causes the motor 65 to forward rotate at a rate proportional to the retraction force applied by the operator. The forward rotation of the motor 65 causes, as described above, the main drive shaft 48 to rotate, which causes the knife 32 in the end effector 12 to be deployed (i.e., begin traversing the channel 22). Rotation of the pinion gear 124, which is connected to the main drive shaft 48, causes the gears 210-220 in the gear box assembly 200 to rotate. Since the first gear 210 is in engagement with the gear portion 232 of the upper portion 230 of the firing trigger 20, the upper portion 232 is caused to rotate CCW, which causes the lower portion 228 to also rotate CCW.

When the knife 32 is fully deployed (i.e., at the end of the cutting stroke), the front face 242 of the upper portion 230 trips the reverse motor sensor 130, which sends a signal to the motor 65 to reverse rotational directional. This causes the main drive shaft assembly to reverse rotational direction to retract the knife 32. Reverse rotation of the main drive shaft assembly causes the gears 210-220 in the gear box assembly to reverse direction, which causes the upper portion 230 of the firing trigger 20 to rotate CW, which causes the lower portion 228 of the firing trigger 20 to rotate CW until the lower portion 228 trips or actuates the stop motor sensor 142 when the knife 32 is fully retracted, which causes the motor 65 to stop. In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particular, to the loading force experienced by the knife 32. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portion 232 of the upper portion 230 to rotate CCW, which causes the gears of the gear box assembly 200 to rotate, thereby causing the pinion gear 124 to rotate, which causes the main drive shaft assembly to rotate.

The above-described embodiments employed power-assist user feedback systems, with or without adaptive control (e.g., using a sensor 110, 130, and 142 outside of the closed loop system of the motor, gear drive train, and end effector) for a two-stroke, motorized surgical cutting and fastening instrument. That is, force applied by the user in retracting the firing trigger 20 may be added to the force applied by the motor 65 by virtue of the firing trigger 20 being geared into (either directly or indirectly) the gear drive train between the motor 65 and the main drive shaft 48. In other embodiments of the present invention, the user may be provided with tactile feedback regarding the position of the knife 32 in the end effector, but without having the firing trigger 20 geared into the gear drive train. FIGS. 37-40 illustrate a motorized surgical cutting and fastening instrument with such a tactile position feedback system.

In the illustrated embodiment of FIGS. 37-40, the firing trigger 20 may have a lower portion 228 and an upper portion 230, similar to the instrument 10 shown in FIGS. 32-36. Unlike the embodiment of FIG. 32-36, however, the upper portion 230 does not have a gear portion that mates with part of the gear drive train. Instead, the instrument includes a second motor 265 with a threaded rod 266 threaded therein. The threaded rod 266 reciprocates longitudinally in and out of the motor 265 as the motor 265 rotates, depending on the direction of rotation. The instrument 10 also includes an encoder 268 that is responsive to the rotations of the main drive shaft 48 for translating the incremental angular motion of the main drive shaft 48 (or other component of the main drive assembly) into a corresponding series of digital signals, for example. In the illustrated embodiment, the pinion gear 124 includes a proximate drive shaft 270 that connects to the encoder 268.

The instrument 10 also includes a control circuit (not shown), which may be implemented using a microcontroller or some other type of integrated circuit, that receives the digital signals from the encoder 268. Based on the signals from the encoder 268, the control circuit may calculate the stage of deployment of the knife 32 in the end effector 12. That is, the control circuit can calculate if the knife 32 is fully deployed, fully retracted, or at an intermittent stage. Based on the calculation of the stage of deployment of the end effector 12, the control circuit may send a signal to the second motor 265 to control its rotation to thereby control the reciprocating movement of the threaded rod 266.

Figure 37:
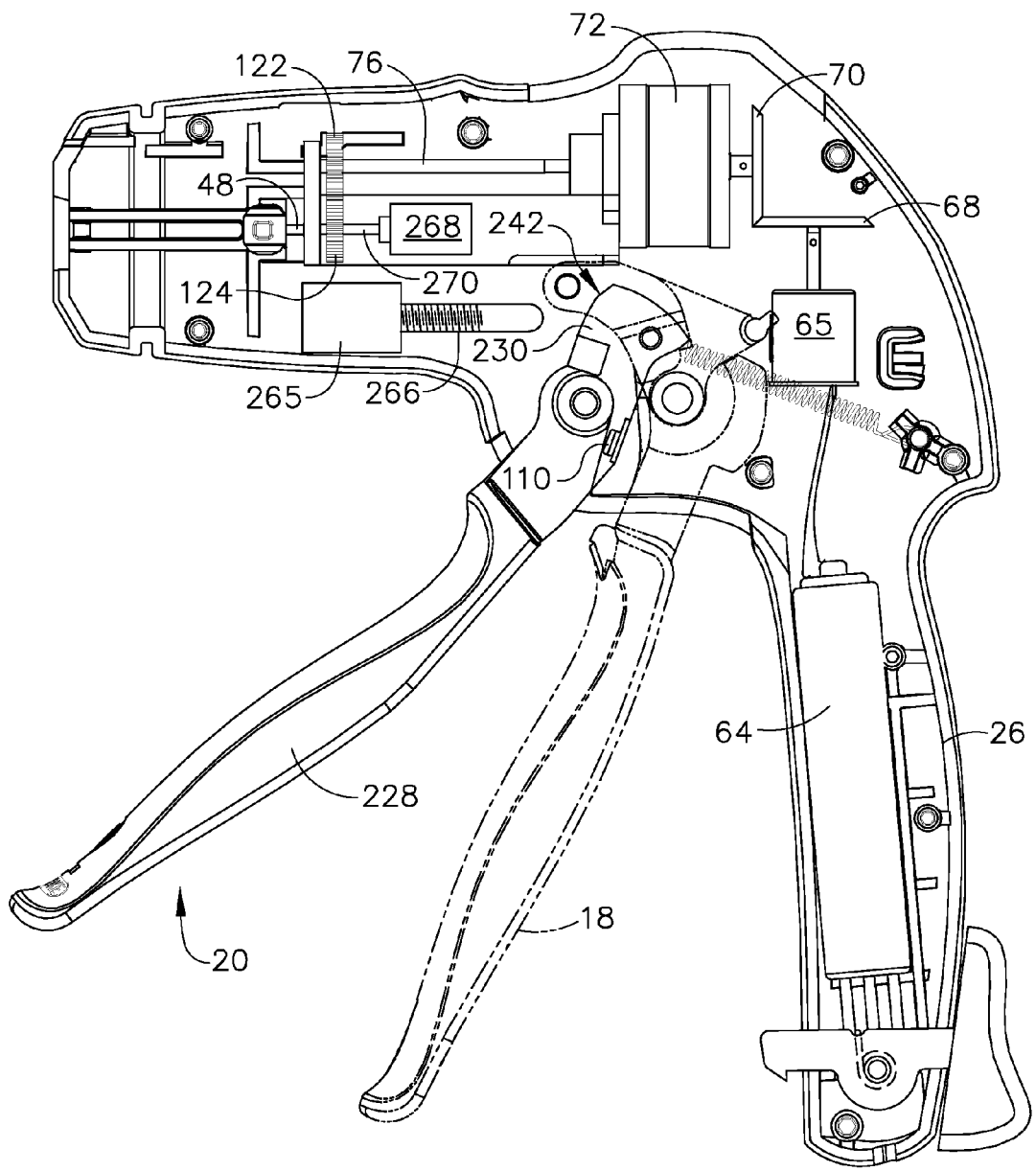
Figure 38:
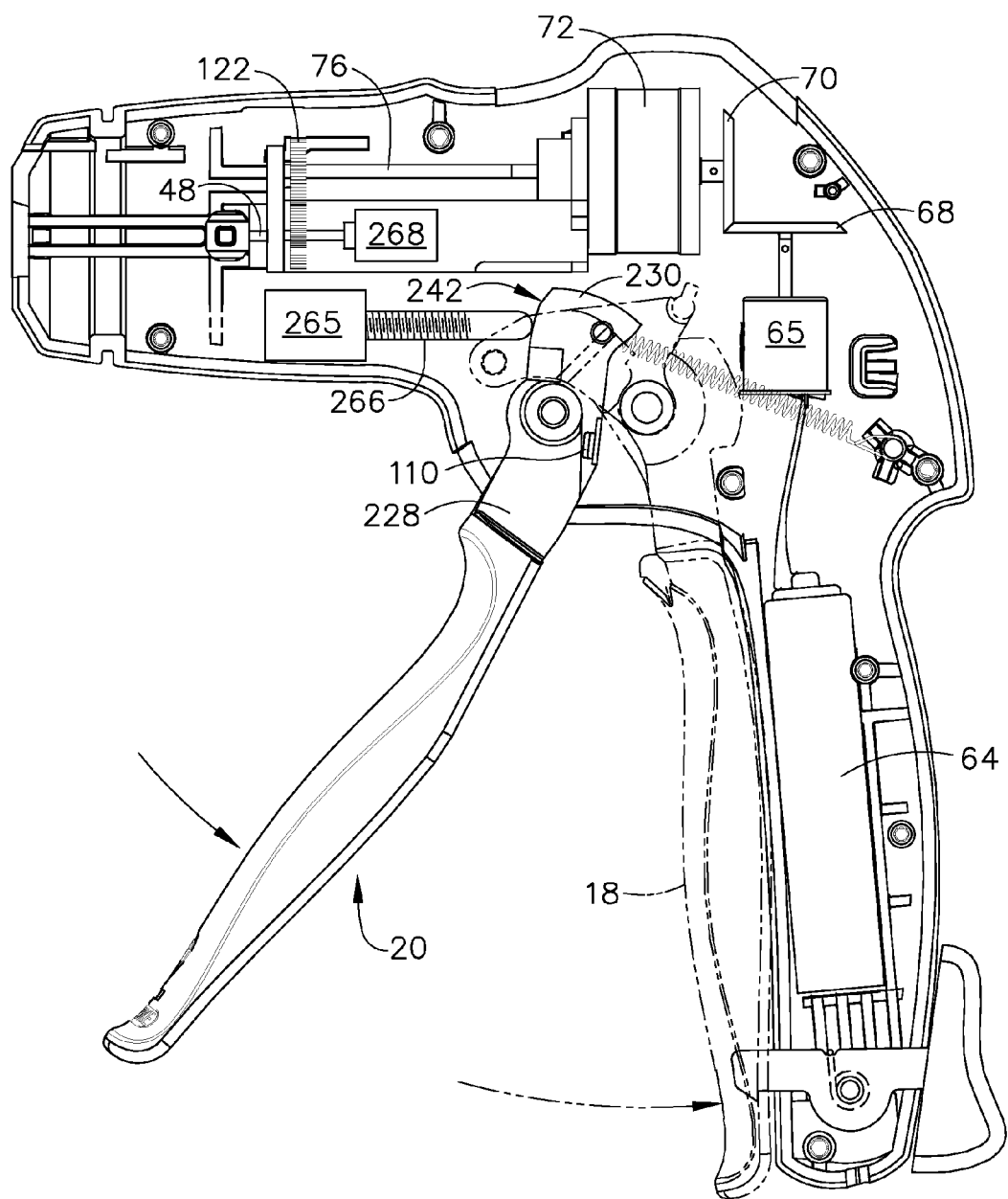
Figure 39:
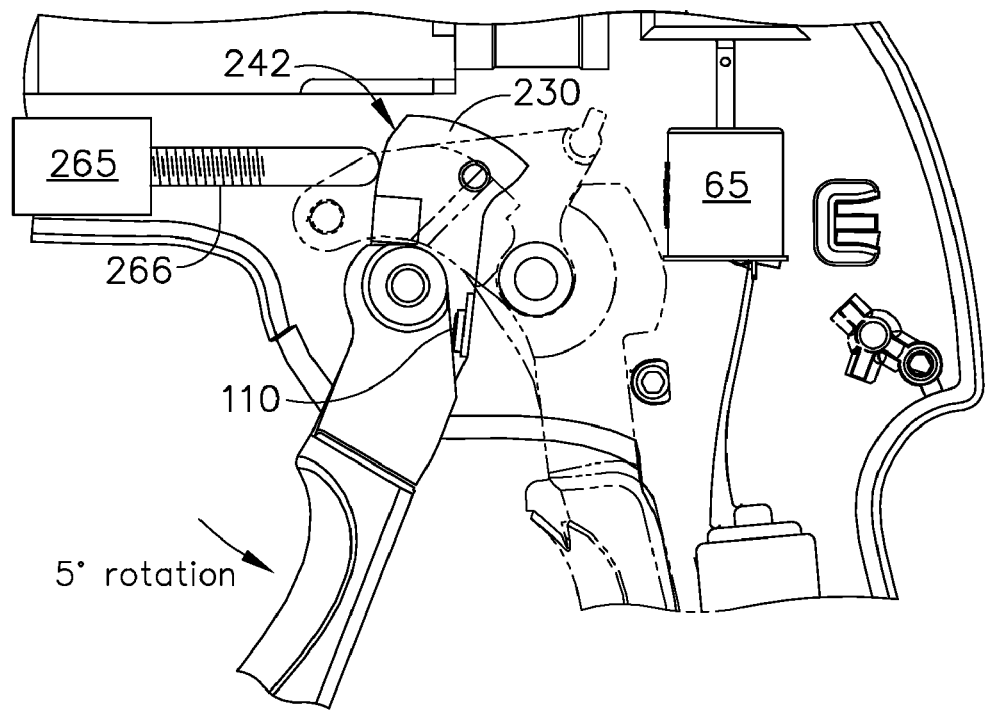
Figure 40:
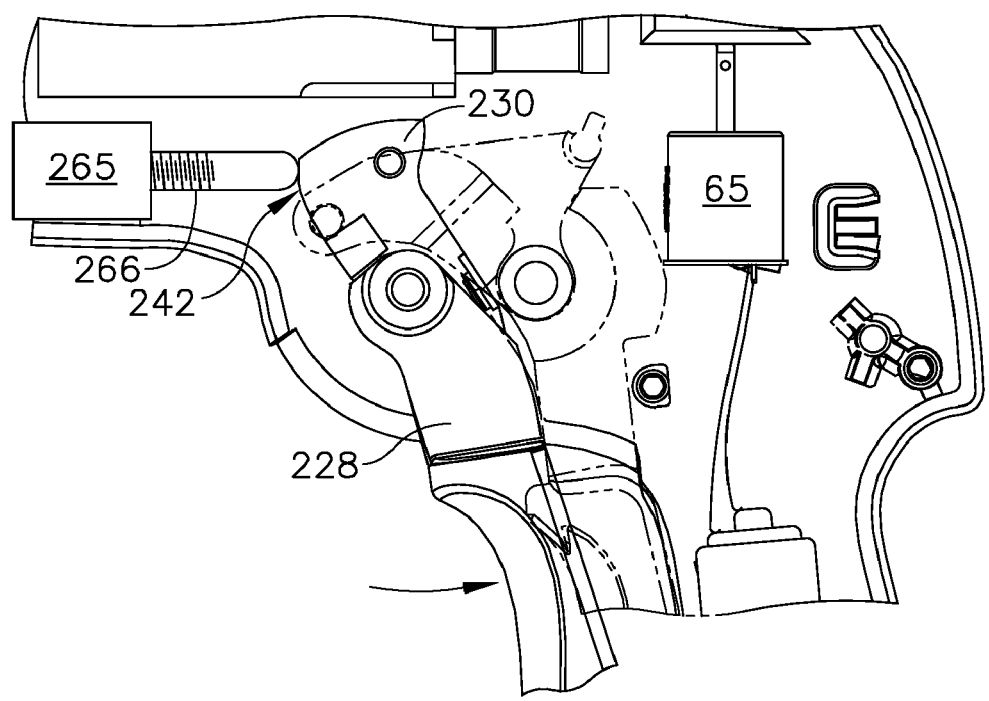

In operation, as shown in FIG. 37, when the closure trigger 18 is not locked into the clamped position, the firing trigger 20 rotated away from the pistol grip portion 26 of the handle 6 such that the front face 242 of the upper portion 230 of the firing trigger 20 is not in contact with the proximate end of the threaded rod 266. When the operator retracts the closure trigger 18 and locks it in the clamped position, the firing trigger 20 rotates slightly towards the closure trigger 20 so that the operator can grasp the firing trigger 20, as shown in FIG. 38. In this position, the front face 242 of the upper portion 230 contacts the proximate end of the threaded rod 266.

As the user then retracts the firing trigger 20, after an initial rotational amount (e.g., 5 degrees of rotation) the run motor sensor 110 may be activated such that, as explained above, the sensor 110 sends a signal to the motor 65 to cause it to rotate at a forward speed proportional to the amount of retraction force applied by the operator to the firing trigger 20. Forward rotation of the motor 65 causes the main drive shaft 48 to rotate via the gear drive train, which causes the knife 32 and sled 33 to travel down the channel 22 and sever tissue clamped in the end effector 12. The control circuit receives the output signals from the encoder 268 regarding the incremental rotations of the main drive shaft assembly and sends a signal to the second motor 265 to caused the second motor 265 to rotate, which causes the threaded rod 266 to retract into the motor 265. This allows the upper portion 230 of the firing trigger 20 to rotate CCW, which allows the lower portion 228 of the firing trigger to also rotate CCW. In that way, because the reciprocating movement of the threaded rod 266 is related to the rotations of the main drive shaft assembly, the operator of the instrument 10, by way of his/her grip on the firing trigger 20, experiences tactile feedback as to the position of the end effector 12. The retraction force applied by the operator, however, does not directly affect the drive of the main drive shaft assembly because the firing trigger 20 is not geared into the gear drive train in this embodiment.

By virtue of tracking the incremental rotations of the main drive shaft assembly via the output signals from the encoder 268, the control circuit can calculate when the knife 32 is fully deployed (i.e., fully extended). At this point, the control circuit may send a signal to the motor 65 to reverse direction to cause retraction of the knife 32. The reverse direction of the motor 65 causes the rotation of the main drive shaft assembly to reverse direction, which is also detected by the encoder 268. Based on the reverse rotation detected by the encoder 268, the control circuit sends a signal to the second motor 265 to cause it to reverse rotational direction such that the threaded rod 266 starts to extend longitudinally from the motor 265. This motion forces the upper portion 230 of the firing trigger 20 to rotate CW, which causes the lower portion 228 to rotate CW. In that way, the operator may experience a CW force from the firing trigger 20, which provides feedback to the operator as to the retraction position of the knife 32 in the end effector 12. The control circuit can determine when the knife 32 is fully retracted. At this point, the control circuit may send a signal to the motor 65 to stop rotation.

According to other embodiments, rather than having the control circuit determine the position of the knife 32, reverse motor and stop motor sensors may be used, as described above. In addition, rather than using a proportional sensor 110 to control the rotation of the motor 65, an on/off switch or sensor can be used. In such an embodiment, the operator would not be able to control the rate of rotation of the motor 65. Rather, it would rotate at a preprogrammed rate.

The various embodiments of the present invention have been described above in connection with cutting-type surgical instruments. It should be noted, however, that in other embodiments, the inventive surgical instrument disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical cutting and fastening instrument comprising:
    an end effector comprising:
        an elongate channel;
        a clamping member pivotably connected to the channel; and a moveable cutting instrument for traversing the channel to cut an object clamped in the end effector by the clamping member when the clamping member is in a clamped position;
a rotary main drive shaft assembly for actuating the cutting instrument in the end effector;
a handle comprising:
  a gear drive train connected to the main drive shaft assembly for rotating the main drive shaft assembly;
  an electric motor for actuating the gear drive train;
  a battery connected to the motor for powering the motor;
  a closure trigger for causing the clamping member to pivot to the clamped position when retracted;
  a firing trigger separate from the closure trigger for actuating the motor when the firing trigger is retracted, wherein a loading force on the firing trigger is related to a loading force experienced by the cutting instrument when the cutting instrument traverses the channel, wherein the firing trigger comprises an upper gear portion that meshes with a gear of the gear drive train;
  a sensor circuit comprising at least one sensor for (i) sensing retraction of the firing trigger, wherein, when retraction of the firing trigger is sensed, the motor is signaled to forward rotate to cause cutting of the object positioned in the end effector by the cutting instrument, (ii) detecting a condition indicative of an end of a cutting stroke by the cutting instrument in the end effector, wherein, when the condition indicative of the end of the cutting stroke is sensed, the motor is signaled to reverse rotate, and (iii) detecting a condition indicative of full retraction of the cutting instrument in the end effector, wherein, when the condition indicative of full retraction is sensed, the motor is signaled to stop rotating; and
means for articulating the end effector.

2. The surgical cutting and fastening instrument of claim 1, further comprising an articulation control for allowing an operator of the instrument to control the means for articulating.

3. The surgical cutting and fastening instrument of claim 1, wherein the means for articulating comprises a universal-joint.

4. The surgical cutting and fastening instrument of claim 1, wherein the means for articulating comprises a bevel gear assembly.

5. The surgical cutting and fastening instrument of claim 1, wherein the means for articulating comprises a torsion cable.

6. The surgical cutting and fastening instrument of claim 1, wherein:
the main drive shaft assembly comprises a proximate drive shaft and a distal drive shaft; and
the means for articulating are connected to the main drive shaft assembly between the proximate drive shaft and the distal drive shaft.

7. The surgical cutting and fastening instrument of claim 1, wherein the sensor circuit comprises:
a run motor sensor for sensing retracting of the firing trigger;
a reverse motor sensor for detecting the condition indicative of the end of the cutting stroke by the cutting instrument in the end effector; and
a stop motor sensor for detecting the condition indicative of full retraction of the cutting instrument in the end effector.

8. The surgical cutting and fastening instrument of claim 6, further comprising a mechanical closure system connected to the closure trigger and to the clamping member for causing the clamping member to pivot to the clamped position when the closure trigger is retracted.

9. The surgical cutting and fastening instrument of claim 8, wherein the mechanical closure system comprises:
a bracket connected to the closure trigger; and
a closure tube assembly having a distal end connected to the clamping member and a proximate end seated in the bracket.

10. The surgical cutting and fastening instrument of claim 6, wherein the end effector includes a staple cartridge seated in the elongate channel and the clamping member comprises an anvil.

11. The surgical cutting and fastening instrument of claim 6, further comprising a locking mechanism for locking the closure trigger when retracted.

12. The surgical cutting and fastening instrument of claim 1, wherein the end effector further comprises a helical drive screw, such that forward rotation of the helical drive screw causes the cutting instrument to undertake the cutting stroke by traveling distally along the channel, and reverse rotation of the helical drive screw causes the cutting instrument to retract by traveling proximately along the channel.

13. A surgical cutting and fastening instrument comprising:
an end effector comprising a moveable cutting instrument;
a rotary main drive shaft assembly for actuating the cutting instrument in the end effector;
a handle comprising:
  a gear drive train connected to the main drive shaft assembly for rotating the main drive shaft assembly;
  an electric motor for actuating the gear drive train;
  a battery connected to the motor for powering the motor;
  a closure trigger for causing the end effector to clamp an object positioned in the end effector when the closure trigger is retracted; and
  a firing trigger separate from the closure trigger for actuating the motor when the firing trigger is retracted, wherein a loading force on the firing trigger is related to a loading force experienced by the cutting instrument when the cutting instrument longitudinally traverses the end effector, wherein the firing trigger comprises an upper gear portion that meshes with a gear of the gear drive train;
  a sensor circuit comprising at least one sensor for (i) sensing retraction of the firing trigger, wherein, when retraction of the firing trigger is sensed, the motor is signaled to forward rotate to cause cutting of the object positioned in the end effector by the cutting instrument, (ii) detecting a condition indicative of an end of a cutting stroke by the cutting instrument in the end effector, wherein, when the condition indicative of the end of the cutting stroke is sensed, the motor is signaled to reverse rotate, and (iii) detecting a condition indicative of full retraction of the cutting instrument in the end effector, wherein, when the condition indicative of full retraction is sensed, the motor is signaled to stop rotating; and
means for articulating the end effector.

14. The surgical cutting and fastening instrument of claim 13, wherein:
the main drive shaft assembly comprises a proximate drive shaft and a distal drive shaft; and
the means for articulating are connected to the main drive shaft assembly between the proximate drive shaft and the distal drive shaft.

15. The surgical cutting and fastening instrument of claim 14, further comprising an articulation control adjacent to the handle for allowing an operator of the instrument to control the means for articulating.

16. A surgical cutting and fastening instrument comprising:
- an end effector comprising a moveable cutting instrument;
- a rotary main drive shaft assembly for actuating the cutting instrument in the end effector, wherein the main drive shaft assembly comprises means for articulating the end effector;
- a handle connecting to the main drive shaft comprising:
  - a gear drive train connected to the main drive shaft assembly for rotating the main drive shaft assembly;
  - an electric motor for actuating the gear drive train;
  - a battery connected to the motor for powering the motor;
  - a closure trigger, closeable by rotation toward a grip portion of the handle, for causing the end effector to clamp an object positioned in the end effector when the closure trigger is retracted;
  - a firing trigger separate from the closure trigger and closeable by rotation toward the grip portion of the handle, wherein the firing trigger is for actuating the motor when the firing trigger is retracted, wherein a loading force on the firing trigger is related to a loading force experienced by the cutting instrument when the cutting instrument longitudinally traverses the end effector, and wherein the firing trigger comprises an upper gear portion that meshes with a gear of the gear drive train; and
  - a sensor circuit comprising at least one sensor for (i) sensing retraction of the firing trigger, wherein, when retraction of the firing trigger is sensed, the motor is signaled to forward rotate to cause cutting of the object positioned in the end effector by the cutting instrument, (ii) detecting a condition indicative of an end of a cutting stroke by the cutting instrument in the end effector, wherein, when the condition indicative of the end of the cutting stroke is sensed, the motor is signaled to reverse rotate, and (iii) detecting a condition indicative of full retraction of the cutting instrument in the end effector, wherein, when the condition indicative of full retraction is sensed, the motor is signaled to stop rotating.

17. The surgical cutting and fastening instrument of claim 7, wherein the run motor sensor comprises a proportional switch such that the rate of rotation of the motor is proportional to the retraction force applied to the firing trigger.

18. The surgical cutting and fastening instrument of claim 13, wherein the sensor circuit comprises:
- a run motor sensor for sensing retracting of the firing trigger;
- a reverse motor sensor for detecting the condition indicative of the end of the cutting stroke by the cutting instrument in the end effector; and
- a stop motor sensor for detecting the condition indicative of full retraction of the cutting instrument in the end effector.

19. The surgical cutting and fastening instrument of claim 16, wherein the sensor circuit comprises:
- a run motor sensor for sensing retracting of the firing trigger;
- a reverse motor sensor for detecting the condition indicative of the end of the cutting stroke by the cutting instrument in the end effector; and
- a stop motor sensor for detecting the condition indicative of full retraction of the cutting instrument in the end effector.

20. A surgical cutting and fastening instrument comprising:
- an end effector comprising:
  - an elongate channel;
  - a clamping member pivotably connected to the channel; and
  - a moveable cutting instrument for traversing the channel to cut an object clamped in the end effector by the clamping member when the clamping member is in a clamped position;
- a rotary main drive shaft assembly for actuating the cutting instrument in the end effector;
- a handle comprising:
  - a gear drive train connected to the main drive shaft assembly for rotating the main drive shaft assembly, wherein the gear drive train comprises a helical drum gear and a ring threaded on the helical gear drum;
  - an electric motor for actuating the gear drive train;
  - a battery connected to the motor for powering the motor;
  - a closure trigger for causing the clamping member to pivot to the clamped position when retracted;
  - a firing trigger separate from the closure trigger for actuating the motor when the firing trigger is retracted, wherein a loading force on the firing trigger is related to a loading force experienced by the cutting instrument when the cutting instrument traverses the channel;
  - an arm connecting the firing trigger to the ring threaded on the helical gear drum;
  - a sensor circuit comprising at least one sensor for (i) sensing retraction of the firing trigger, wherein, when retraction of the firing trigger is sensed, the motor is signaled to forward rotate to cause cutting of the object positioned in the end effector by the cutting instrument, (ii) detecting a condition indicative of an end of a cutting stroke by the cutting instrument in the end effector, wherein, when the condition indicative of the end of the cutting stroke is sensed, the motor is signaled to reverse rotate, and (iii) detecting a condition indicative of full retraction of the cutting instrument in the end effector, wherein, when the condition indicative of full retraction is sensed, the motor is signaled to stop rotating; and
- means for articulating the end effector.

21. The surgical cutting and fastening instrument of claim 20, further comprising an articulation control for allowing an operator of the instrument to control the means for articulating.

22. The surgical cutting and fastening instrument of claim 20, wherein the means for articulating comprises a universal-joint.

23. The surgical cutting and fastening instrument of claim 20, wherein the means for articulating comprises a bevel gear assembly.

24. The surgical cutting and fastening instrument of claim 20, wherein the means for articulating comprises a torsion cable.

25. The surgical cutting and fastening instrument of claim 20, wherein:
- the main drive shaft assembly comprises a proximate drive shaft and a distal drive shaft; and
- the means for articulating are connected to the main drive shaft assembly between the proximate drive shaft and the distal drive shaft.

26. The surgical cutting and fastening instrument of claim 20, wherein the sensor circuit comprises:
- a run motor sensor for sensing retracting of the firing trigger;
- a reverse motor sensor for detecting the condition indicative of the end of the cutting stroke by the cutting instrument in the end effector; and
- a stop motor sensor for detecting the condition indicative of full retraction of the cutting instrument in the end effector.

27. The surgical cutting and fastening instrument of claim 26, wherein the run motor sensor comprises a proportional switch such that the rate of rotation of the motor is proportional to the retraction force applied to the firing trigger.

28. The surgical cutting and fastening instrument of claim 20, further comprising a mechanical closure system connected to the closure trigger and to the clamping member for causing the clamping member to pivot to the clamped position when the closure trigger is retracted.

29. The surgical cutting and fastening instrument of claim 28, wherein the mechanical closure system comprises:
- a bracket connected to the closure trigger; and
- a closure tube assembly having a distal end connected to the clamping member and a proximate end seated in the bracket.

30. The surgical cutting and fastening instrument of claim 20, wherein the end effector includes a staple cartridge seated in the elongate channel and the clamping member comprises an anvil.

31. The surgical cutting and fastening instrument of claim 20, further comprising a locking mechanism for locking the closure trigger when retracted.

32. The surgical cutting and fastening instrument of claim 20, wherein the end effector further comprises a helical drive screw, such that forward rotation of the helical drive screw causes the cutting instrument to undertake the cutting stroke by traveling distally along the channel, and reverse rotation of the helical drive screw causes the.

* * * * *